US008283294B2

(12) United States Patent
Kastrup et al.

(10) Patent No.: US 8,283,294 B2
(45) Date of Patent: Oct. 9, 2012

(54) METHOD FOR CLONING COGNATE ANTIBODIES

(75) Inventors: Jesper Kastrup, Stenløse (DK); Lars S. Nielsen, Nivå (DK); Per-Johan Meijer, Copenhagen (DK)

(73) Assignee: Symphogen A/S, Lyngby (DK)

( * ) Notice: Subject to any disclaimer, the term of this patent is extended or adjusted under 35 U.S.C. 154(b) by 122 days.

(21) Appl. No.: 12/074,066

(22) Filed: Feb. 29, 2008

(65) Prior Publication Data

US 2008/0227660 A1 Sep. 18, 2008

Related U.S. Application Data

(60) Provisional application No. 60/904,772, filed on Mar. 5, 2007.

(30) Foreign Application Priority Data

Mar. 1, 2007 (DK) .............................. 2007 00316

(51) Int. Cl.
C40B 40/08 (2006.01)
C40B 50/06 (2006.01)

(52) U.S. Cl. ..................... 506/17; 506/26; 424/133.1

(58) Field of Classification Search .................... 506/17, 506/26; 424/133.1
See application file for complete search history.

(56) References Cited

U.S. PATENT DOCUMENTS

| 4,683,202 | A | 7/1987 | Mullis |
| 5,698,435 | A | 12/1997 | Robinson et al. |
| 5,882,856 | A | 3/1999 | Shuber |
| 5,912,172 | A | 6/1999 | Eshhar et al. |
| 6,096,878 | A | 8/2000 | Honjo et al. |
| 6,111,166 | A | 8/2000 | van de Winkel |
| 6,258,529 | B1 | 7/2001 | Berdoz et al. |
| 6,538,124 | B1 | 3/2003 | Idusogie et al. |
| 6,849,259 | B2 | 2/2005 | Haurum et al. |
| 6,867,021 | B2 | 3/2005 | Maes et al. |
| 6,994,963 | B1 | 2/2006 | Murphy et al. |
| 7,749,697 | B2 | 7/2010 | Oleksiewicz et al. |
| 2001/0027249 | A1 | 10/2001 | Le et al. |
| 2002/0102604 | A1 | 8/2002 | Milne Edwards et al. |
| 2003/0096343 | A1 | 5/2003 | Robinson et al. |
| 2003/0104477 | A1 | 6/2003 | Buechler et al. |
| 2003/0175837 | A1 | 9/2003 | Le et al. |
| 2004/0067532 | A1 | 4/2004 | Zhu et al. |
| 2005/0180967 | A1 | 8/2005 | Haurum et al. |
| 2006/0228350 | A1 | 10/2006 | Wu et al. |
| 2006/0275766 | A1 | 12/2006 | Haurum et al. |
| 2007/0003515 | A1 | 1/2007 | Leonard et al. |
| 2007/0141048 | A1 | 6/2007 | Oleksiewicz et al. |
| 2008/0069822 | A1 | 3/2008 | Jensen et al. |
| 2008/0131882 | A1 | 6/2008 | Rasmussen et al. |
| 2008/0226630 | A1 | 9/2008 | Lantto et al. |
| 2009/0004192 | A1 | 1/2009 | Pedersen et al. |
| 2009/0017017 | A1 | 1/2009 | Rasmussen et al. |
| 2009/0111142 | A1 | 4/2009 | Nielsen et al. |
| 2009/0136498 | A1 | 5/2009 | Haurum et al. |
| 2009/0137003 | A1 | 5/2009 | Tolstrup et al. |
| 2010/0069262 | A1 | 3/2010 | Nielsen et al. |
| 2010/0310558 | A1 | 12/2010 | Oleksiewicz et al. |

FOREIGN PATENT DOCUMENTS

| FR | 2724393 | 3/1996 |
| WO | WO 92/15678 A1 | 9/1992 |
| WO | WO 93/03151 A1 | 2/1993 |
| WO | WO 93/20227 A1 | 10/1993 |
| WO | WO 94/08008 A1 | 4/1994 |
| WO | WO 95/20401 A1 | 8/1995 |
| WO | WO 96/08564 A1 | 4/1996 |
| WO | WO 98/57994 A2 | 12/1998 |
| WO | WO 99/16904 A1 | 4/1999 |
| WO | WO 99/29888 A1 | 5/1999 |
| WO | WO 01/89563 A1 | 11/2001 |
| WO | WO 01/92291 A2 | 12/2001 |
| WO | 2004/003019 | * 6/2004 |
| WO | WO 2004/061104 A2 | 7/2004 |
| WO | WO 2005/042774 A2 | 5/2005 |
| WO | WO 2006/007850 A1 | 1/2006 |
| WO | WO 2006/007853 A2 | 1/2006 |
| WO | WO 2007/003041 A1 | 1/2007 |
| WO | WO 2007/101441 A1 | 1/2007 |
| WO | WO 2007/065433 A2 | 6/2007 |

OTHER PUBLICATIONS

Rudikoff et al (Proc Natl Acad Sci USA 1982 vol. 79 p. 1979).*
Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Soderlind et al. (Gene 160:269-272 (1995).*
Soderlind et al. (Immunotechnology 4:279-285 (Mar. 1999).*
Ardavín, C., et al., "B Cell Response After MMTV Infection: Extrafollicular Plasmablasts Represent the Main Infected Population and Can Transmit Viral Infection," *J. Immunol.* 162:2538-2545, The American Association of Immunologists (1999).
Babcook, J.S., et al., "A novel strategy for generating monoclonal antibodies from single, isolated lymphocytes producing antibodies of defined specificities," *Proc. Natl. Acad. Sci. USA* 93:7843-7848, National Academy of Science (1996).
Bregenholt, S., et al., "Recombinant Human Polyclonal Antibodies: A New Class of Therapeutic Antibodies Against Viral Infections," *Curr. Pharm. Des.* 12:2007-2015, Bentham Science Publishers (Jan. 2006).
Haurum, J.S., "Recombinant polyclonal antibodies: the next generation of antibody therapeutics?," *Drug Discov. Today* 11:655-660, Elsevier Science (Jul. 2006).
Liu, A.Y., et al., "Expression of mouse::human immunoglobulin heavy-chain cDNA in lymphoid cells," *Gene* 54:33-40, Elsevier Science (1987).
Liu, M.-L., et al., "Chronic idiopathic myelofibrosis terminating in extramedullary anaplastic plasmacytoma," *Leuk. Lymphoma* 47:315-322, Taylor & Francis (Feb. 2006).

(Continued)

*Primary Examiner* — Lynn Bristol
(74) *Attorney, Agent, or Firm* — Sterne, Kessler, Goldstein & Fox P.L.L.C.

(57) ABSTRACT

The invention relates to a procedure for linking cognate pairs of $V_H$ and $V_L$ encoding sequences from a population of cells enriched in particular surface antigen markers. The linking procedure involves a multiplex molecular amplification procedure capable of linking nucleotide sequences of interest in connection with the amplification, in particular polymerase chain reaction (multiplex PCR). The method is particularly advantageous for the generation of cognate pair libraries as well as combinatorial libraries of variable region encoding sequences from immunoglobulins. The invention also relates to methods for generation of chimeric human/non-human antibodies and expression libraries generated by such methods.

36 Claims, 8 Drawing Sheets

OTHER PUBLICATIONS

Figure 1:
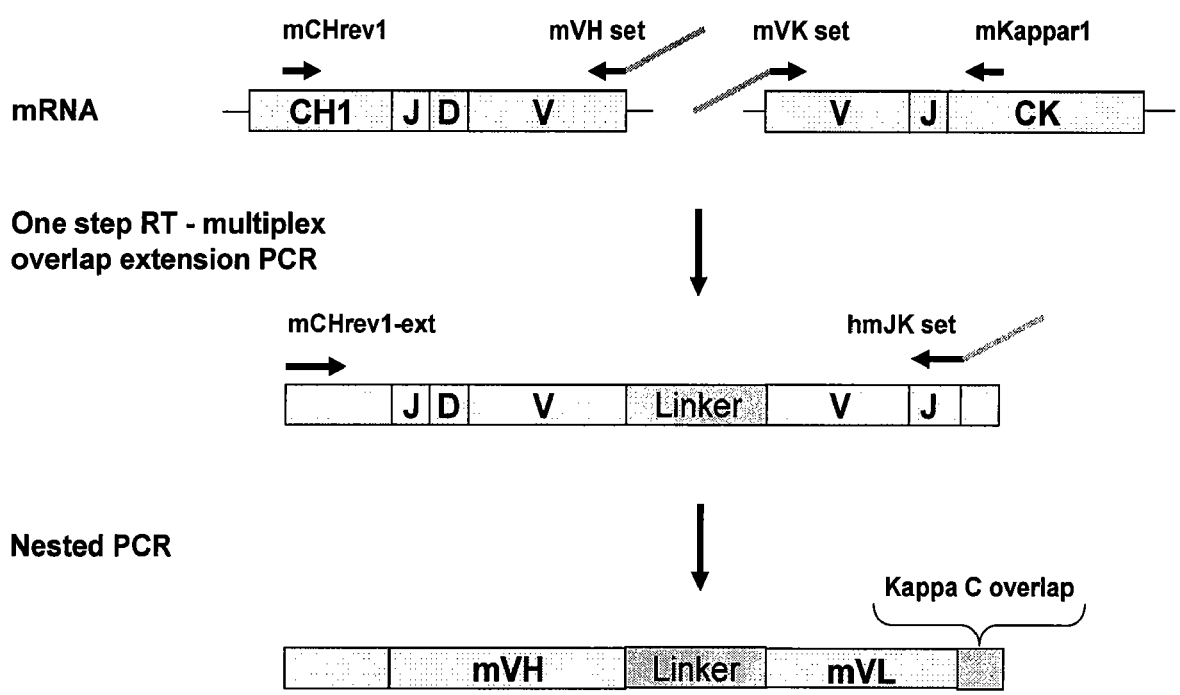

Logtenberg, T., "Antibody cocktails: next-generation biopharmaceuticals with improved potency," *Trends Biotechnol.* 25:390-394, Elsevier Science (Sep. 2007).

Meijer, P.-R., et al., "Isolation of Human Antibody Repertoires with Preservation of the Natural Heavy and Light Chain Pairing," *J. Mol. Biol.* 358:764-772, Elsevier Science (May 2006).

Orlandi, R., et al., "Cloning immunoglobulin variable domains for expression by the polymerase chain reaction," *Proc. Natl. Acad. Sci. USA* 86:3833-3837, National Academy of Science (1989).

Poulsen, T.R., et al., "Kinetic, Affinity, and Diversity Limits of Human Polyclonal Antibody Responses against Tetanus Toxoid," *J. Immunol.* 179:3841-3850, The American Association of Immunologists (Sep. 2007).

Requena, L., "Afectación cutánea específica en pacientes con mieloma múltiple. Estudio clínico-patológico, inmunohistoquímico y citogenético de 40 casos," *Actas Dermosifiliogr.* 96:424-440, Doyma (2005).

STNEasy Database, English language abstract of Requena, L., *Actas Dermosifiliogr.* 96:424-440.

Requena, L., et al., "Cutaneous Involvement in Multiple Myeloma: A Clinicopathologic, Immunohistochemical, and Cytogenetic Study of 8 Cases," *Arch Dermatol.* 139:475-486, American Medical Association (2003).

Sharon, J., et al., "Recombinant Polyclonal Antibodies for Cancer Therapy," *J. Cell. Biochem.* 96:305-313, Wiley-Liss (2005).

Tolstrup, A.B., et al., "Development of recombinant human polyclonal antibodies for the treatment of complex human diseases," *Expert Opin. Biol. Ther.* 6:905-912, Ashley Publications (Sep. 2006).

Weissenhorn, W., et al., "Chimerization of antibodies by isolation of rearranged genomic variable regions by the polymerase chain reaction," *Gene* 106:273-277, Elsevier Science (1991).

Wiberg, F.C., et al., "Production of Target-Specific Recombinant Human Polyclonal Antibodies in Mammalian Cells," *Biotechnol. Bioeng.* 94:396-405, Wiley (Jun. 2006).

Altman, J. et al., "Phenotypic Analysis of Antigen-Specific T Lymphocytes," *Science* 274:94-96, American Association for the Advancement of Science, US (1996).

Barbas, C. et al., "Assembly of combinatorial antibody libraries on phage surfaces: The gene III site," *Proc. Natl. Acad. Sci. USA* 88:7978-7982, The National Academy of Sciences, US (1991).

Burgart, L. et al., "Multiplex Polymerase Chain Reaction," *Mod. Path.* 5:320-323, U.S. and Canadian Acad. Path., US (1992).

Callan, M. et al., "Direct Visualization of Antigen-specific CD8+ T Cells during the Primary Immune Response to Epstein-Barr Virus In Vivo," *J. Exp. Med.* 187:1395-1402, The Rockefeller University Press, US (1998).

Campbell, M. et al., "Use of Family Specific Leader Region Primers for PCR Amplification of the Human Heavy Chain Variable Region Gene Repertoire," *Mol. Immunol.* 29:193-203, Pergamon Press plc, US (1992).

Chapal, N. et al., "Human Anti-Thyroid Peroxidase Single-Chain Fragment Variable of Ig Isolated from a Combinatorial Library Assembled In-Cell: Insights into the In Vivo Situation," *J Immunol* 164(8): 4162-9, American Association of Immunologists, US (Apr. 2000).

Chapal, N. et al., "In-Cell Assembly of scFv from Human Thyroid-Infiltrating B Cells," *BioTechniques* 23:518-524, Eaton Publishing Company, UK (1997).

Chin, J. et al., "Production of neutralizing human monoclonal antibody directed to tetanus toxin in CHO cell," *Biologicals* 31:45-53, Elsevier Science Ltd., UK (Mar. 2003).

Compton, J., "Nucleic acid sequence-based amplification," *Nature* 350:91-92, Nature Publishing Group, UK (1991).

Coronella, J. et al., "Amplification of IgG VH and VL (Fab) from single human plasma cells and B cells," *Nucleic Acids Res.* 28:e85, Oxford University Press, UK (2000).

Database Biotechno, Accession No. 1999:29089942, Abstract for Akatsuka, Y., et al., "Rapid screening of T-cell receptor (TCR) variable gene usage by multiplex PCR: Application for assessment of clonal composition," *Tissue Antigens* 53:122-134, Blackwell Publishing, Inc., UK (1999).

Database Biotechno, Accession No. 1999:29223369, Abstract for Tanabe, R., et al., "Expression of myosin heavy chain isoforms in porcine muscles determined by multiplex PCR," *Journal of Food Science* 64:222-225, Institute of Food Technologists, US (1999).

Database Biotechno, Accession No. 1999:29445017, Abstract for Cheng, L., et al., "Expression in normal human tissues of five nucleotide excision repair genes measured simultaneously by multiplex reverse transcription-polymerase chain reaction," *Cancer Epidemiology Biomarkers and Prevention* 8:801-807, American Association for Cancer Research, US (1999).

de Haard, H. et al., "A Large Non-immunized Human Fab Fragment Phage Library That Permits Rapid Isolation and Kinetic Analysis of High Affinity Antibodies," *J. Biol. Chem.* 274:18218-18230, The American Society for Biochemistry and Molecular Biology, Inc., US (1999).

de Wildt, R. et al., "Antibody arrays for high-throughput screening of antibody-antigen interactions," *Nat. Biotechnol.* 18:989-994, Nature America Inc., US (2000).

Den W. et al., "A bidirectional phage display vector for the selection and mass transfer of polyclonal antibody libraries," *J. Immunol. Meth.* 222:45-57, Elsevier Science B.V., UK (1999).

Embleton, M. et al., "In-cell PCR from mRNA: amplifying and linking the rearranged immunoglobulin heavy and light chain V-genes within single cells," *Nucleic Acids Res.* 20:3831-3837, Oxford University Press, UK (1992).

Fitzgerald, K., "In vitro display technologies—new tools for drug discovery," *Drug Discovery Today* 5:253-258, Elsevier Science Ltd., UK (2000).

Gherardi, E. and Milstein, C., "Original and artificial antibodies," *Nature* 357:201-202, Nature Publishing Group, UK (1992).

Guatelli, J. et al., "Isothermal, in vitro amplification of nucleic acids by a multienzyme reaction modeled after retroviral replication," *Proc. Natl. Acad. Sci. USA* 87:1874-1878, The National Academy of Sciences, US (1990).

Harris, E. et al., "Typing of Dengue Viruses in Clinical Specimens and Mosquitoes by Single-Tube Multiplex Reverse Transcriptase PCR," *J Clin Microbiol.* 36(9): 2634-9, American Society for Microbiology, US (Sep. 1998).

Henegariu, O. et al., "Multiplex PCR: Critical Parameters and Step-by-Step Protocol," *BioTechniques* 23:504-511, Eaton Publishing Company, US (1997).

Horton, R. et al., "Engineering hybrid genes without the use of restriction enzymes: gene splicing by overlap extension," *Gene* 77:61-68, Elsevier Science Publishers B.V., UK (1989).

Kang, A. et al., "Linkage of recognition and replication functions by assembling combinatorial antibody Fab libraries along phage surfaces," *Proc. Natl. Acad. Sci. USA* 88:4363-4366, The National Academy of Sciences, US (1991).

Kuroiwa, Y. et al., "Cloned transchromosomic calves producing human immunoglobulin," *Nat. Biotechnol.* 20:889-894, Nature Publishing Group, UK (2002).

Kurokawa, M. et al., "Paired cloning of the T cell receptor α and β genes from a single T cell without the establishment of a T cell clone," *Clin. Exp. Immunol.* 123:340-345, Blackwell Sci. Ltd., UK (2001).

Lakew, M. et al., "Combined immunomagnetic cell sorting and ELISPOT assay for the phenotypic characterization of specific antibody-forming cells," *J. Immunol. Meth.* 203:193-198, Elsevier Science B.V., UK (1997).

Lang, A. et al., "Polyclonal Preparations of Anti-Tetanus Toxoid Antibodies Derived from a Combinatorial Library Confer Protection," *Biotechnology* 13(7): 683-5, Nature Pub. Co., US (Jul. 1995).

Liu, A. et al., "Sequencing heavy- and light-chain variable genes of single B-hybridoma cells by total enzymatic amplification," *Proc. Natl. Acad. Sci. USA* 89:7610-7614, The National Academy of Sciences, US (1992).

Markoulatos, P. et al., "Multiplex Polymerase Chain Reaction: A Practical Approach," *J. Clin. Lab. Anal.* 16:47-51, Wiley-Liss, Inc., US (2002).

Marks, J., "Human Monoclonal Antibodies from V-Gene Repertoires Expressed on Bacteriophage," in *Antibody Engineering, 2nd Ed.*, Borrebaeck, C., ed., Oxford University Press, New York, pp. 53-88 (1995).

Marks, J. et al., "By-passing Immunization," *J. Mol. Biol.* 222:581-597, Academic Press Limited, UK (1991).

Mullinax, R. et al., "Expression of a Heterodimeric Fab Antibody Protein in One Cloning Step," *BioTechniques* 12:864-869, Eaton Publishing, US (1992).

Nielson, H. et al., "Identification of prokaryotic and eukaryotic signal peptides and prediction of their cleavage sites," *Protein Eng.* 10:1-6, Oxford University Press, UK (1997).

Novak, E. et al., "MHC class II tetramers identify peptide-specific human CD4+ T cells proliferating in response to influenza A antigen," *J. Clin. Invest.* 104:R63-R67, American Society for Clinical Investigation, US (1999).

Ørum, H. et al., "Efficient method for constructing comprehensive murine Fab antibody libraries displayed on phage," *Nuc. Acids Res.* 21:4491-4498, Oxford University Press, UK (1993).

Poddar, S., "Influenza virus types and subtypes detection by single step single tube multiplex reverse transcription-polymerase chain reaction (RT-PCR) and agarose gel electrophoresis" *J Virol Methods* 99: 63-70, Elsevier Science B.V., UK (2002).

Ray, P. et al., "Single cell multiplex PCR amplification of five dystrophin gene exons combined with gender determination," *Molecular Human Repro* 7(5): 489-494, Oxford University Press, UK (2001).

Thirion, S. et al., "Mono- and bispecific single-chain antibody fragments for cancer therapy," *Eur. J. Cancer Preven.* 5:507-511, Rapid Science Publishers, UK (1996).

Traggiai, E. et al., "An efficient method to make human monoclonal antibodies from memory B cells: potent neutralization of SARS coronavirus," *Nat. Med.* 10:871-875, Nature Publishing Company, UK (Aug. 2004).

Walker, G. et al., "Strand displacement amplification—an isothermal, in vitro DNA amplification technique," *Nucleic Acids Res.* 20:1691-1696, Oxford University Press, UK (1992).

Wang, X. and Stollar, B., "Human immunoglobulin variable region gene analysis by single cell RT-PCR," *J. Immunol. Meth.* 244:217-225, Elsevier Science B.V., UK (2000).

Willcox, B. et al., "Production of soluble αβ T-cell receptor heterodimers suitable for biophysical analysis of ligand binding," *Protein Sci.* 8:2418-2423, Cambridge University Press, UK (1999).

Wrammert, J. et al., "Rapid cloning of high-affinity human monoclonal antibodies against influenza virus," *Nature* 453:667-71, Nature Publishing Group, UK (2008).

Wu, D. and Wallace, R., "The Ligation Amplification Reaction (LAR)-Amplification of Specific DNA Sequences Using Sequential Rounds of Template-Dependent Ligation," *Genomics* 4:560-569, Academic Press, Inc., UK (1989).

Xiaocong, Y. et al., "Neutralizing antibodies derived from the B cells of 1918 influenza pandemic survivors," *Nature* 455:532-6, Nature Publishing Group, UK (2008).

International Search Report for International Application No. PCT/DK2008/050048, European Patent Office, Netherlands, mailed on Sep. 1, 7 pages.

Office Action mailed Jul. 8, 2008, in U.S. Appl. No. 10/572,431, Oleksiewicz, M. et al., 35 U.S.C. § 371(c) date of Mar. 20, 2006.

Office Action mailed Apr. 17, 2009, in U.S. Appl. No. 10/572,431, Oleksiewicz, M. et al., 35 U.S.C. § 371(c) date of Mar. 20, 2006.

Office Action mailed Nov. 24, 2009, in U.S. Appl. No. 10/572,431, Oleksiewicz, M. et al., 35 U.S.C. § 371(c) date of Mar. 20, 2006.

Tung et al., "Phenotypically distinct B cell development pathways map to the three B cell lineages in the mouse," *Proc. Natl. Acad. Sci. USA* 103(16):6293-98, National Academy of Sciences (2006).

Caroll, S., et al., "ACSD labelling and magnetic cell separation: a rapid method of separating antibody secreting cells from non-secreting cells," *Journal of Immunological Methods* 296: 171-178, Elsevier (2008).

Horst, A., et al., "Detection and characterization of plasma cells in peripheral blood: correlation of IgE+ plasma cell frequency with IgE serum titre," *Clinical and Experimental Immunology* 130: 370-378, Blackwell Publishing Ltd. (2002).

Manz, R. et al., "Lifetime of plasma cells in the bone marrow," *Nature* 338: 133-134, Macmillan Publishers Ltd. (1997).

Manz, R. et al., "Analysis and sorting of live cells according to secreted molecules, relocated to a cell-surface affinity matrix," *Proc. Natl. Acad. Sci. USA* 92: 1921-1925, National Academy of Sciences, United States (1995).

Office Action mailed Sep. 28, 2011, in U.S. Appl. No. 12/549,921, Lars Soegaard Nielsen, et al. filed Aug. 28, 2009.

Office Action mailed Mar. 25, 2011, in U.S. Appl. No. 12/549,921, Lars Soegaard Nielsen, et al., filed Aug. 28, 2009.

Bell, J. and Gray, D., "Antigen-Capturing Cells Can Masquerade as Memory B Cells," *Journal of Experimental Medicine* 197(10):1233-1244, Rockefeller University Press, United States (2003).

Gulley, M.L., et al., "Identication of a Murine Pan-T Cell Antigen Which is Also Expressed During the Terminal Phases of B Cell Differentiation," *Journal of Immunology* 140(11):3751-3757, The American Association of Immunologists, United States (1988).

Honjo, T., et al., eds., *Immunoglobulin Genes*, pp. 7-8, Academic Press, London, England (1989).

Hoyer, B.F., et al., "Short-Lived Plasmablasts and Long-Lived Plasma Cells Contribute to Chronic Humoral Autoimmunity in NZB/W Mice," *Journal of Experimental Medicine* 199(11):1577-1584, Rockefeller University Press, United States (2004).

Kallies, A., et al., "Plasma Cell Onotogeny Defined by Quantitative Changes in Blimp-1 expressions," *Journal of Experimental Medicine* 200(8):967-977, Rockefeller University Press, United States (2004).

Ledbetter, J.A., et al., "CD45 regulates signal transduction and lymphocyte activation by specific association with receptor molecules on T or B cells," *PNAS* 85:8628-8632, National Academy of Sciences, United States (1988).

Lu, L-S., et al., "Identification of a germ-line pro-B cell subset that distinguishes the fetal/neonatal from the adult B cell development pathway," *PNAS* 99(5):3007-3012, National Academy of Sciences, United States (2002).

Neurath, M.F., et al., "BSAP: a key regulator of B-cell development and differentiation," *Immunology Today* 16(12):564-569, Elsevier Science Ltd., England (1995).

Shimoda, M., et al., "Role of MHC Class II Memory B Cells in Post-Germinal Center B Cell Homeostasis and Memory Response," *Journal of Immunology* 176:2122-2133, American Association of Immunologists, Inc., United States (2006).

Soro, P.G., et al., "Differential Involvement of the Transcription Factor Blimp-1 in T Cell-Independent and-Dependent B Cell Differentiation to Plasma Cells," *Journal of Immunology* 163:611-617, American Association of Immunologists, United States (1999).

Tsung, J.W. and Herzenberg, L.A., "Unraveling B-1 progenitors," *Current Opinion in Immunology* 19:150-155, Elsevier Ltd., United States (2007).

Wells, S.M., et al., "CD43 (S7) Expression Identifies Peripheral B Cell Subsets," *Journal of Immunology* 153:5503-5515, American Association of Immunologists, United States (1994).

Xiang, Z., et al., "FcγRIIb controls bone marrow plasma cell persistence and apoptosis," *Nature Immunology* 8(4):419-429, Nature Publishing Group, England (2007).

Xu, S. and Lam, K-P., "Delayed Cellular Maturation and Decreased Immunoglobulin κ Light Chain Production In Immature B Lymphocytes Lacking B Cell Linker Protein," *Journal of Experimental Medicine* 196(2):197-206, Rockefeller University Press, United States (2002).

Notice of Opposition to European Patent No. EP 2121920, European Patent Office, Netherlands, mailed Jun. 4, 2012.

\* cited by examiner

| Tube: MHCII/B220 | | | |
|---|---|---|---|
| Population | #Events | %Parent | %Total |
| All Events | 30,000 | | 100.0 |
| P1 | 5,909 | 19.7 | 19.7 |
| Live | 24,091 | 80.3 | 80.3 |
| P2 | 1,257 | 5.2 | 4.2 |
| P3 | 609 | 48.4 | 2.0 |
| P4 | 361 | 59.3 | 1.2 |

METHOD FOR CLONING COGNATE ANTIBODIES

This applications claims the benefit of the filing date of U.S. Provisional Appl. No. 60/904,772, filed Mar. 5, 2007, and Danish Appl. No. PA 2007 00316, filed Mar. 1, 2007, both of which are incorporated by reference in their entirety.

BACKGROUND OF THE INVENTION

1. Field of the Invention

The present invention relates to a procedure for linking cognate pairs of $V_H$ and $V_L$ encoding sequences from a population of cells enriched in particular surface antigen markers. The linking procedure involves a multiplex molecular amplification procedure capable of linking nucleotide sequences of interest in connection with the amplification, in particular polymerase chain reaction (multiplex PCR). The method is particularly advantageous for the generation of cognate pair libraries as well as combinatorial libraries of variable region encoding sequences from immunoglobulin. The invention also relates to methods for generation of chimeric human/non-human antibodies and expression libraries generated by such methods.

2. Background Art

WO 2005/042774 (Symphogen) discloses a method for linking nucleotide sequences of interest in particular cognate pairs of $V_H$ and $V_L$ encoding sequences using a multiplex molecular procedure. The sequences of interest are preferably amplified and linked from isolated single cells following limited dilution or other cell separation techniques. The reference discloses various ways of enriching a lymphocyte containing cell population to obtain a population of plasma cells that are particularly suitable for the multiplex molecular amplification procedure.

BRIEF SUMMARY OF THE INVENTION

The present invention focuses on methods for generating libraries of immunoglobulin encoding sequences from non-human animals and methods for generating in a few steps adapted for high throughput cloning and screening, libraries of vectors coding for chimeric antibodies comprising human constant regions and non-human variable regions.

In a first aspect the invention relates to a method of producing a library of cognate pairs comprising linked variable region encoding sequences, said method comprising:
a) providing a lymphocyte-comprising cell fraction from a donor;
b) obtaining a population of isolated single cells, comprising distributing cells from said cell fraction individually into a plurality of vessels, wherein at least a subpopulation of the cells express CD43 and CD138 antigen or MHCII and B220 antigen; and c) amplifying and effecting linkage of the variable region encoding sequences contained in said population of isolated single cells by amplifying, in a multiplex molecular amplification procedure, nucleotide sequences of interest using a template derived from an isolated single cell or a population of isogenic cells; and effecting linkage of the nucleotide sequences of interest amplified.

This method provides a library of cognate pair antibodies or antibody fragments.

In another aspect the invention relates to a method of linking a plurality non-contiguous nucleotide sequences of interest randomly said method comprising:

a) amplifying, in a multiplex molecular amplification procedure, nucleotide sequences of interest using a template derived from a population of genetically diverse cells;
b) wherein the genetically diverse cells are derived from a lymphocyte-comprising cell fraction, from a donor;
c) wherein at least a subpopulation of the cells express CD43 and CD138 antigen or MHCII and B220 antigen; and
d) effecting linkage of the nucleotide sequences of interest amplified in step a).

This method provides a combinatorial library of randomly combined heavy and light chain variable domains.

Experimental evidence provided in the present application establish that cell populations isolated from mouse splenocytes and being positive for the listed surface antigens provide a good starting material for cloning of antibody encoding sequences using a multiplex molecular amplification method. The methods of the invention can easily be applied to other species expressing the orthologs of CD43 and CD138 or MHCII and B220, in particular the methods can be applied to other rodent such as rat.

The method provides several advantages over the alternative, viz generation of hybridoma. When preparing hybridoma from an immunised mouse, the established cell lines will encode a repertoire of different antibody isotypes. The hybridoma cell lines will subsequently have to be screened for both function (e.g. binding to a specific antigen, efficacy in neutralising a pathogen) and for the antibody isotype. Thus it requires a two step screening procedure to select a hybridoma with a particular antibody isotype and with a particular effect in a functional assay. Finally, in order to generate a producer cell line, the antibody secreted by the selected hybridoma will need to be cloned and sequenced before it can be transferred to a producer cell line.

Using the method of the present invention, the antibody isotype is determined by the primers used for the multiplex molecular amplification, and therefore this will not need to be determined. The antibody isotype may be also be determined (and can be changed) by the subsequent linking or splicing of constant domain(s) to cloned variable sequences. Furthermore, the method of the invention provides a library of polynucleotides that can be easily sequenced and/or inserted into vectors, such as expression, transfer, display or shuttle vectors, so that once a particular antibody has been selected, it is already cloned, its sequence is already known and it can be transferred easily to an appropriate expression vector for production of antibody.

It is expected that the cells sorted according to the provided protocol provide a source of high affinity antibodies, potentially with affinities in the picomolar range. Monoclonal antibodies from hybridoma do not possess affinities in the picomolar range, and will need to be synthetically affinity matured to reach these affinities.

According to one embodiment these methods further comprise assessing prior to multiplex molecular amplification that the population of lymphocyte-comprising cells comprises cells express CD43 and CD138 antigen or MHCII and B220 antigen, preferably CD43 and CD138. Also the methods may include enriching said lymphocyte-comprising cell fraction for a lymphocyte population expressing CD43 and CD138 antigen or MHCII and B220 prior to multiplex molecular amplification.

Preferably the methods further comprise isolating from said lymphocyte-comprising population cells expressing CD43 and CD138 antigen or MHCII and B220 antigen prior to multiplex molecular amplification. In a preferred embodiment the isolated cells or subpopulation of cells are CD138 High/CD43 High or CD138 Intermediate/CD43 High relative to the lymphocyte-comprising cell fraction. More preferably the isolated cells or subpopulation of cells are CD138 High/CD43 High relative to the lymphocyte-comprising cell fraction.

Enrichment or isolation preferably comprises an automated sorting procedure, such as MACS or FACS.

In a further aspect the invention relates to a method for generating a vector encoding a chimeric antibody with human constant regions and non-human variable regions, said method comprising:

a) providing a lymphocyte-comprising cell fraction from a non-human animal;
b) obtaining a population of isolated single cells, comprising distributing cells from said cell fraction individually into a plurality of vessels;
c) amplifying and effecting linkage of the variable region encoding nucleic acids contained in said population of isolated single cells by amplifying, in a multiplex molecular amplification procedure, said nucleic acids using a template derived from an isolated single cell or a population of isogenic cells; and effecting linkage of the amplified nucleic acids encoding variable regions of heavy and light chains;
d) effecting linkage of the amplified variable regions to human constant regions; and
e) inserting the obtained nucleic acid into a vector.

Preferably the non-human animal is a mouse. To the extent that the methods of the invention are applied to mouse cells, the methods are named: Mouse-Symplex™ or mSymplex™.

By this aspect of the invention there is provided a novel method for generation of libraries of chimeric human/non-human antibodies. This is made possible by combining the multiplex molecular amplification and subsequent cloning into a vector backbone with ligation and/or splicing of human heavy and light chain constant domains. Traditionally, in a method for generating chimeric human/non-human antibodies, the chimerisation has been the last step after hybridoma have been established and screened and the encoded antibody has been cloned. Chimerisation may affect the binding specificity and/or affinity of an antibody, and thus there is a risk that a good monoclonal mouse antibody loses its efficacy when it is chimerised into a human/mouse antibody.

By the provision of a method that directly generates an antibody of chimeric antibodies, the screening can be carried out on products that do not need to be modified further prior to preclinical and clinical development.

The constant human regions can be provided in a molecular amplification step or they can be provided as part of a vector-backbone, into which the variable regions are cloned following molecular amplification. In a preferred embodiment the method comprises a further amplification step, wherein a polynucleotide encoding a human constant light chain or a fragment thereof with an overlap capable of providing linkage to the variable light chain, is added to the PCR mixture together with a primer set capable of amplification of a construct comprising in order: a murine VH chain, a linker, a murine VL chain, and a human constant light chain.

In another embodiment the method comprises a further amplification step, wherein a polynucleotide encoding human constant heavy chain or a fragment thereof with an overlap capable of providing linkage to the variable heavy chain, is added to the PCR mixture together with a primer set capable of amplification of a construct comprising in order: a human constant heavy chain, a murine VH chain, a linker, and a murine VL chain.

Consequently there is also provided a library of vectors encoding chimeric antibodies each antibody member consisting of non-human immunoglobulin variable region encoding sequences, and human immunoglobulin heavy and light chain constant regions.

Preferably, the vectors are expression vectors enabling the expression of the antibody members of the library for subsequent screening. More preferably the expression vector is for mammalian expression.

The vectors of the library may be obtained by a method of the invention.

In one embodiment the light chain constant region is a kappa constant region.

The non-human sequences may be from rat, sheep, goat, rabbit, guinea-pig or other suitable animal for which immunisation protocols have been described, for which sequence information is available to allow the design of suitable primers, and for which suitable cell sorting techniques enable sorting of plasma cells for single cell mulitiplex molecular amplification to link cognate pairs of variable region sequences. In one embodiment, the non-human sequences are of non-human primate origin, such as cynomolgus monkey, Rhesus monkey, chimpanzee, or macaque. Preferably the non-human sequences are rodent, such as murine or rat. In another embodiment the non-human sequences are rabbit sequences.

Preferably the variable regions of the antibodies are cognate pairs.

In another aspect the invention relates to a sub-library which codes for antibodies exhibiting desired binding specificities directed against a particular target, selected from a library according to the invention.

BRIEF DESCRIPTION OF THE DRAWINGS/FIGURES

FIG. 1. Murine—mSymplex™ PCR: Multiplex overlap extension RT-PCR for the amplification and cognate linkage of heavy and light chain antibody genes from a single cell. Exemplary primer mixes used for the RT-PCR and the nested PCR are described in detail in Table 2 and Table 3 (or Table 5).

Figure 2:
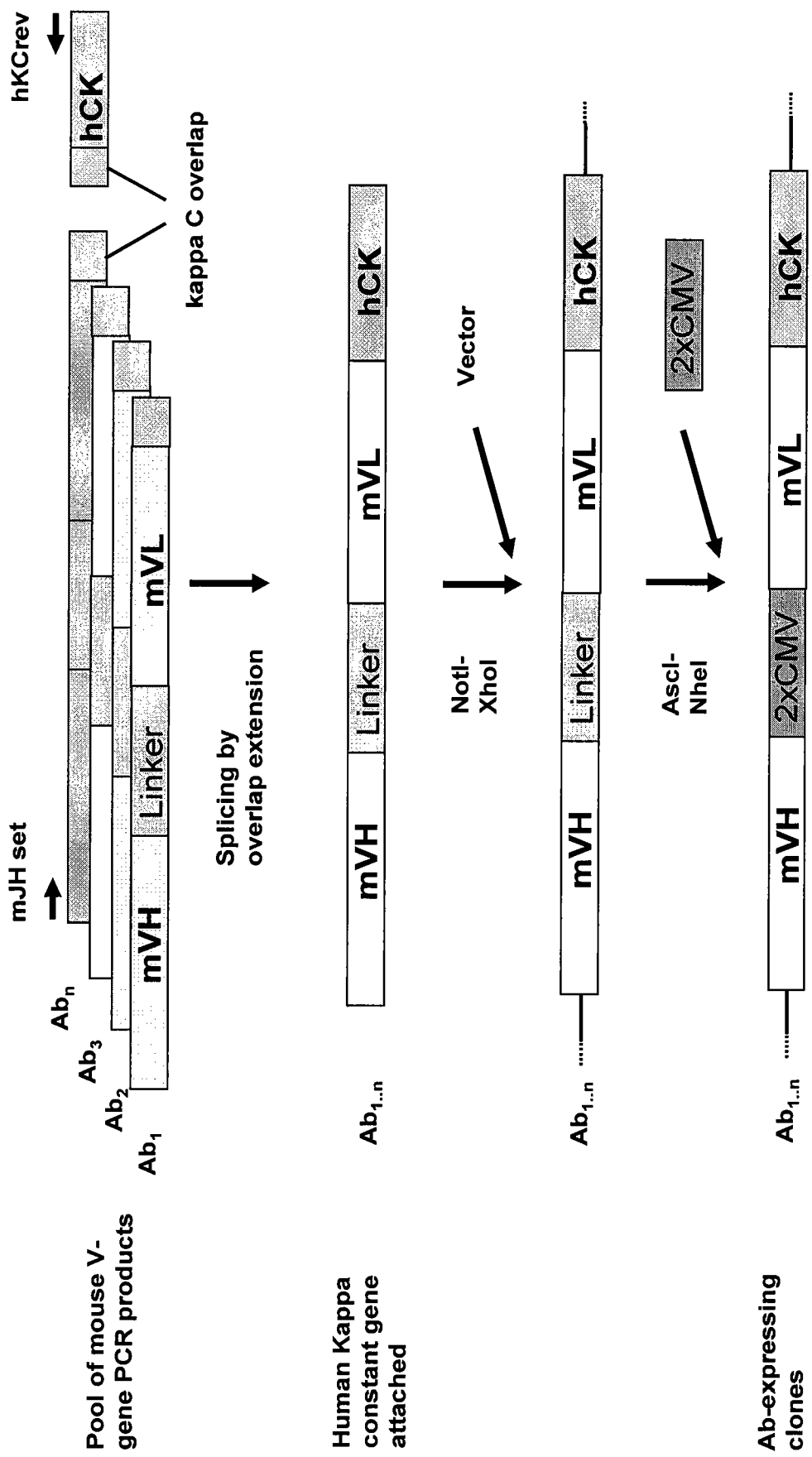

FIG. 2. Murine repertoire cloning: a pool of mSymplex™ PCR products encoding VH/VL gene pairs from single plasma cells were spliced to the gene encoding human kappa constant light chain by splicing by overlap extension. The pool of genes, encoding complete human-mouse chimeric antibodies, was inserted in an expression vector followed by an insertion of a bi-directional promoter cassette (2×CMV). The primer mixes used for the human kappa splicing are described in detail in Table 6.

Figure 3A:
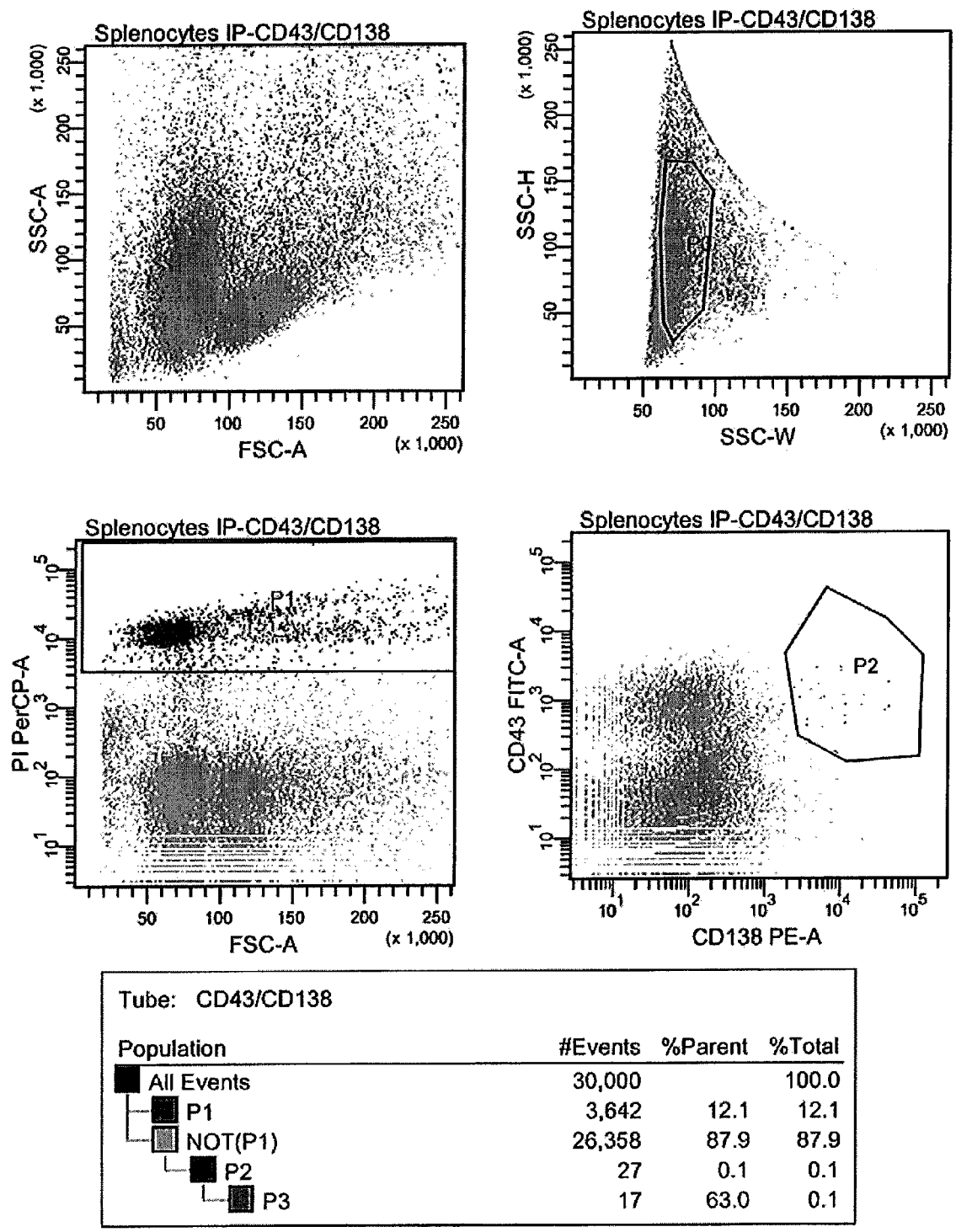
Figure 3B:
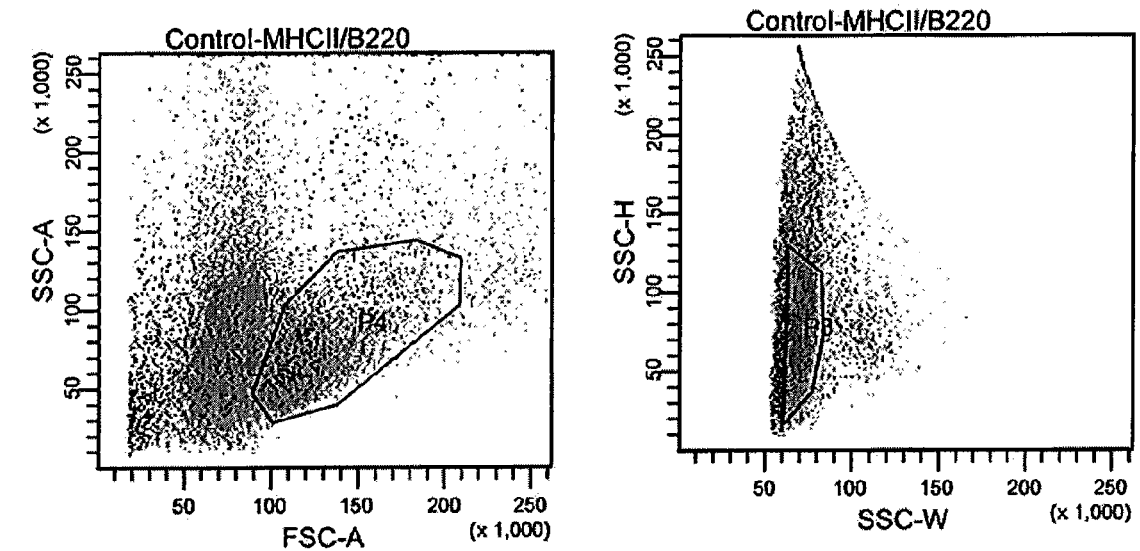
Figure 3B:
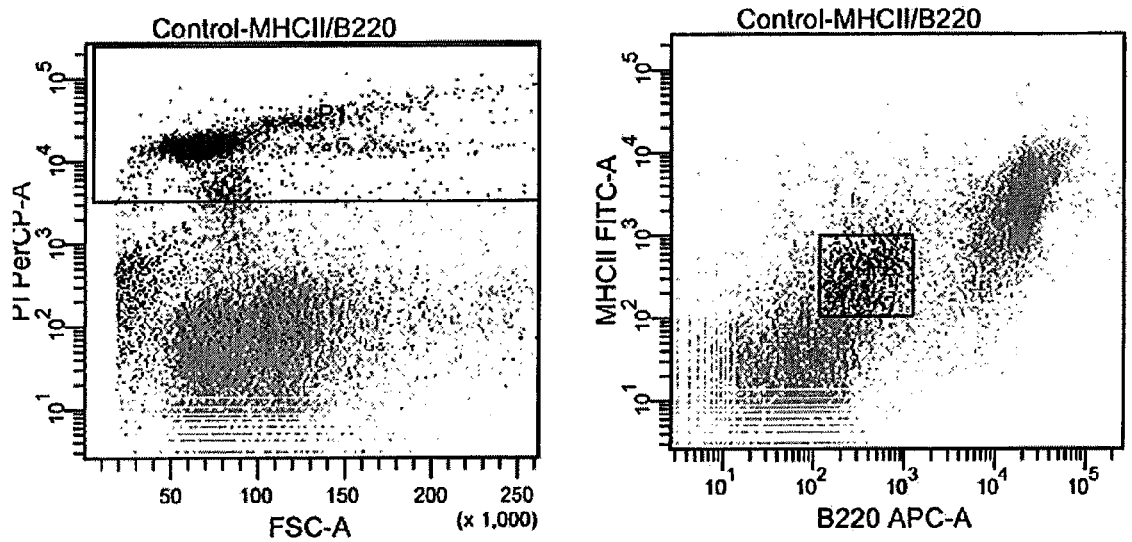

FIG. 3. Sorting of mouse splenocytes. (A) For isolating plasma cells defined as CD43 high, CD138 high, PI (propidium iodide) positive or dead cells were excluded in the bottom left panel (Not P1). Then plasma cells were gated as CD43 high, CD138 high in bottom right panel (P2). Finally, doublets were excluded in the SSC-H, SSC-W plot top right panel (P3). Cells positive for all three gates were sorted into ELISPOT plates. (B) For isolating plasma blasts defined as MHCII intermediate, B220intermediate, PI (propidium iodide) positive or dead cells were excluded in the bottom left panel (Not P1). Then plasma blasts were gated as MHCII intermediate, B220intermediate, bottom right panel (P2). Doublets were excluded in the SSC-H, SSC-W plot top right panel (P3), and finally cells were gated for size in top left panel (P4). Cells positive for all four gates were sorted into ELISPOT plates.

Figure 4:
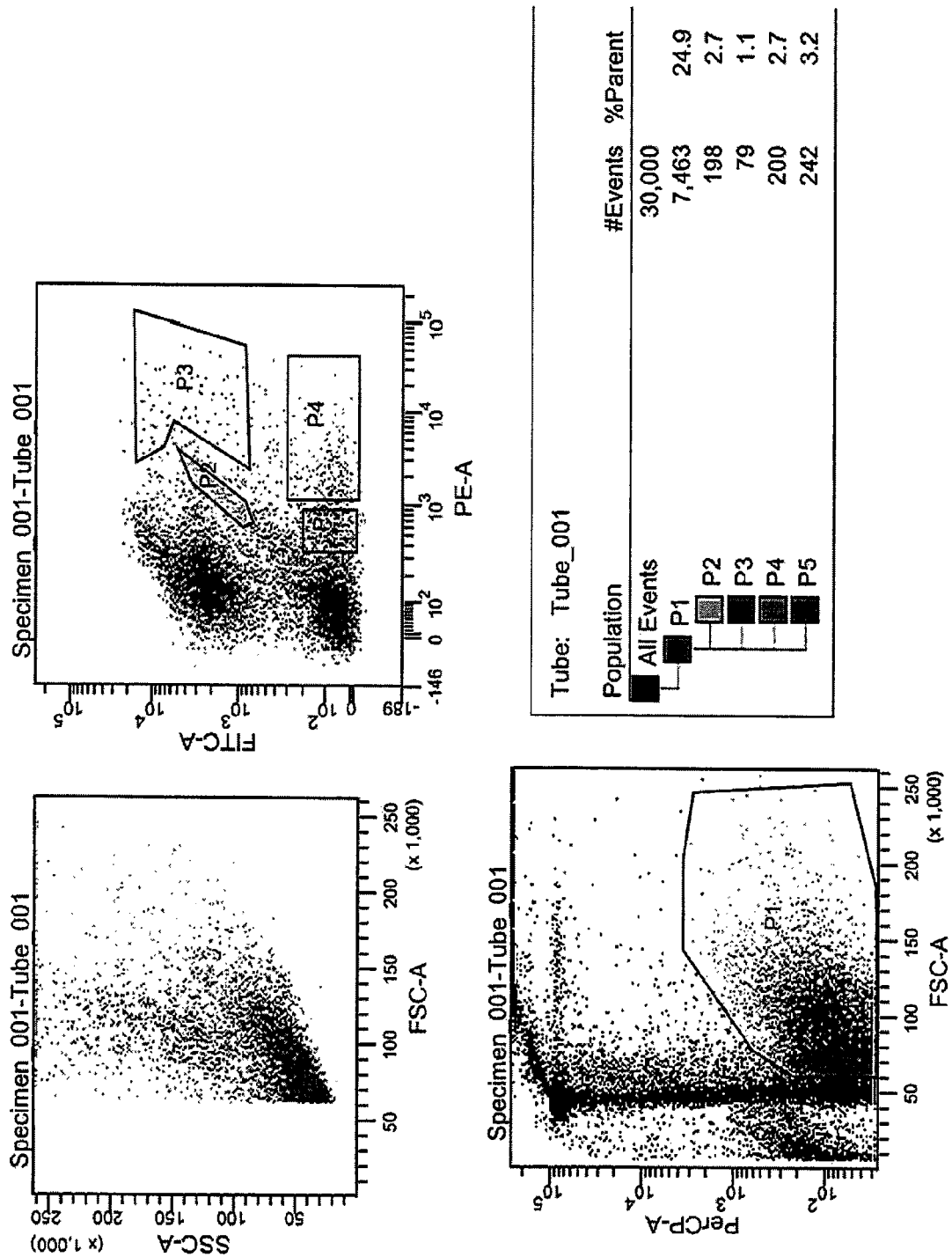

FIG. 4. Sorting of mouse splenocytes. Firstly, PI positive or dead cells were excluded in the bottom left panel (P1). In the top right dot plot, CD138 PE and CD43 FITC are depicted.

Four gates were set on different phenotypic cell populations: P2 is CD138 intermediate, CD43 high. P3 is CD138 high, CD43 high. P4 is CD138 high, Cd43 neg. P5 is CD138 intermediate, CD43 low. 10,000 cells positive for P1 and each of the four gates were sorted into test tubes and frozen for evaluation by symplex.

Figure 5:
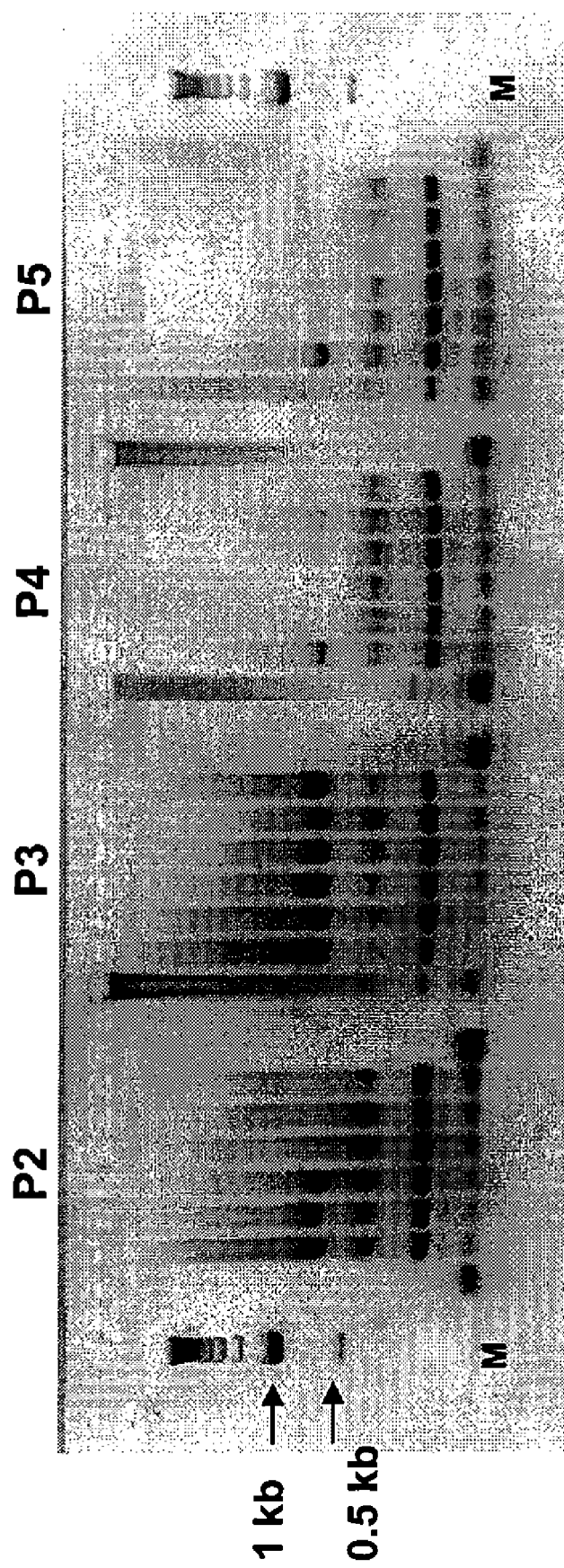

FIG. 5. Gel electrophoresis of PCR products from Symplex PCR titration of cellular lysate from the 4 sorted fractions. P2, P3, P4 and P5 are the gates sorted according to FIG. 4. M are molecular weight markers.

Figure 6:
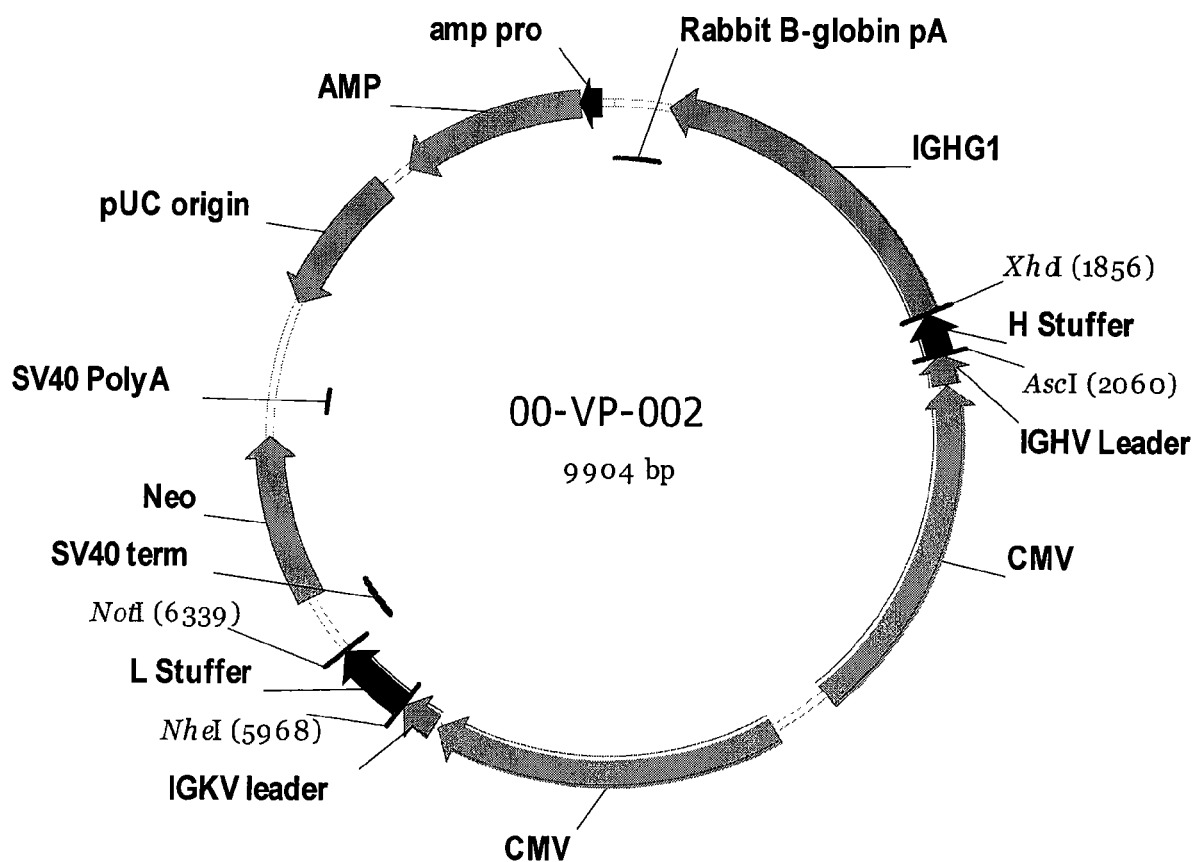

FIG. 6. A schematic representation of the mammalian full-length antibody expression vector 00-VP-002. Amp and Amp pro, ampicillin resistance gene and its promoter; pUC origin, pUC origin of replication; CMV, mammalian promoter driving the expression of the light chain and the heavy chain; IGHV Leader, genomic human heavy chain leader; H stuffer, insert that is exchanged for the heavy chain variable region encoding sequence; IGHG1, sequence encoding for genomic immunoglobulin isotype G1 heavy chain constant region (sequence is shown in Appendix 1); Rabbit B-globin A, rabbit beta-globin polyA sequence; IGKV Leader, murine kappa leader; L Stuffer, insert that is exchanged for the light chain encoding sequence; SV40 term, simian virus 40terminator sequence; FRT, Flp recognition target site; Neo, neomycin resistance gene; SV40 poly A, simian virus 40 poly A signal sequence.

Figure 7:
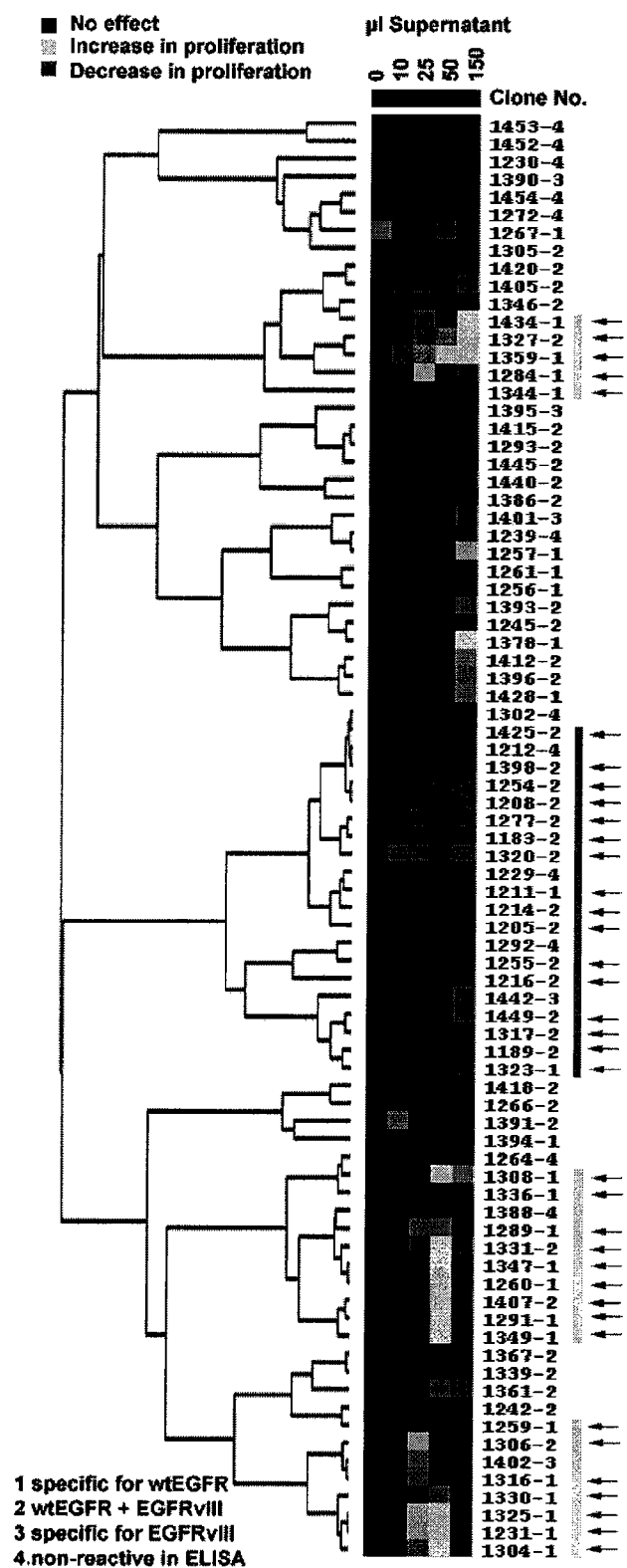

FIG. 7. Analysis of a repertoire of chimeric anti-hEGFR antibodies.

Cluster analysis of the absorbance difference at 450-620 nm. Supernatants are clustered by reactivity as indicated by the number (1 to 4) following the clone no. Dark grey indicate a decrease in the number of metabolically active cells, whereas light grey indicate an increase in the number of metabolically active cells. Black indicates supernatants with no effect on the number of metabolically active cells.

DETAILED DESCRIPTION OF THE INVENTION

The present invention sets out to provide further possibilities for using the amplification and linkage method disclosed in WO 2005/042774 for providing collections of antibody vectors from non-human animals. These improvements enable the cloning of human/non-human chimeric antibody encoding sequences with cognate pairs of variable regions to be fitted to a high-throughput format. This is basically achieved by providing a new starting material for the amplification and linkage processes and by providing methods for generation of libraries of chimeric human/non-human antibodies with cognate pairs of variable regions.

One aspect of the invention is a method of linking heavy and light chain variable sequences comprising amplifying, in a multiplex molecular amplification procedure, the relevant nucleotide sequences using a template derived from an isolated single cell, a population of isogenic cells or a population of genetically diverse cells and effecting a subsequent linkage of the amplified sequences.

Definitions

The term "cognate pair" describes an original pair of non-contiguous nucleic acids of interest that are contained within or derived from a single cell. In preferred embodiments, a cognate pair comprises two variable region encoding sequences which together encode for a binding protein variable domain and which gene sequences are derived from the same cell. Thus, when expressed either as a complete binding protein or as a stable fragment thereof, they preserve the binding affinity and specificity of the binding protein originally expressed from this cell. A cognate pair can for example be comprised of an antibody variable heavy chain encoding sequence associated with a variable light chain encoding sequence from the same cell, or a T cell receptor a chain encoding sequence associated with a β chain encoding sequence from the same cell. A library of cognate pairs is a collection of such cognate pairs.

The term "hot-start polymerase" describes polymerases that are inactive or have very low activity at temperatures used for reverse transcription. Such polymerases need to be activated by high temperatures (90 to 95° C.) to become functional. This is for example an advantage in single-step RT-PCR procedures, since this prohibits interference of the polymerase with the reverse transcriptase reaction.

The term "isogenic population of cells" describes a population of genetically identical cells. In particular, an isogenic population of cells derived by clonal expansion of an isolated single cell is of interest in the present invention.

The term "isolated single cell" describes a cell that has been physically separated from a population of cells corresponding to "a single cell in a single vessel". When distributing a population of cells individually among a plurality of vessels, a population of isolated single cells is obtained. As specified in the section entitled "Template sources" the proportion of vessels with a single cell is not necessarily a 100% in order to call it a population of single cells.

Terms derived from "link" or "linkage" in relation to amplification describes the association of the amplified nucleic acid sequences encoding the nucleic acid sequences of interest into a single segment. In relation to cognate pairs a segment comprises nucleic acid sequences encoding a variable domain, e.g. an antibody heavy chain variable region associated with an antibody light chain variable region encoding sequence, derived from the same cell. The linkage can either be achieved simultaneously with the amplification or as an immediate step following the amplification. There are no requirements to the form or functionality of the segment, it may be linear, circular, single stranded or double stranded. Nor is the linkage necessarily permanent, one of the nucleic acid sequences of interest may be isolated from the segment if desired, one of the variable region encoding sequence may for example be isolated from a cognate pair segment. However, as long as the original variable regions constituting the cognate pair are not scrambled with other variable regions, they are still considered a cognate pair, although not linked together into a single segment. The linkage is preferably a nucleotide phosphodiester linkage. However, linkage can also be obtained by different chemical cross linking procedures.

The term "multiplex molecular amplification" describes the simultaneous amplification of two or more target sequences in the same reaction. Suitable amplification methods include the polymerase chain reaction (PCR) (U.S. Pat. No. 4,683,202), ligase chain reaction (LCR), (Wu and Wallace, 1989, Genomics 4, 560-9), strand displacement amplification (SDA) technique (Walker et al., 1992, Nucl. Acids Res. 20, 1691-6), self-sustained sequence replication (Guatelli et al., 1990, Proc. Nat. Acad. Sci. U.S.A., 87, 1874-8) and nucleic acid based sequence amplification (NASBA) (Compton J., 1991, Nature 350, 91-2). The latter two amplification methods involve isothermal reactions based on isothermal transcription, which produce both single stranded RNA (ssRNA) and double stranded DNA (dsDNA).

The term "multiplex PCR" describes a variant of PCR in which two or more target sequences are amplified simultaneously, by including more than one set of primers in the same reaction, e.g. one primer set adapted for amplification of the heavy chain variable region and one primer set adapted for amplification of the kappa chain variable region in the same PCR reaction. Additionally or alternatively a primer set adapted for amplification of the lambda chain variable region may be combined with these primer sets.

The term "multiplex RT-PCR" describes a multiplex PCR reaction, which is preceded by a reverse transcription (RT) step. The multiplex RT-PCR, can either be performed as a two-step process with a separate RT step prior to the multiplex PCR, or as a single-step process where all components for both RT and multiplex PCR are combined in a single tube.

The terms "multiplex overlap-extension PCR" and "multiplex overlap-extension RT-PCR" implies that the multiplex PCR or multiplex RT-PCR is performed utilizing a multiplex overlap-extension primer mix to amplify the target sequences, thereby enabling simultaneous amplification and linkage of the target sequences.

The term "a plurality of vessels" describes any object (or collection of objects) which enables the physical separation of a single cell from a population of cells. This may be tubes, multiwell plates (e.g. 96-well, 384-well, microtiter plates or other multiwell plates), arrays, microarrays, microchips, gels, or a gel matrix. Preferably the object is applicable for PCR amplification.

The term "polyclonal protein" or "polyclonality" as used herein, refers to a protein composition comprising different, but homologous protein molecules, preferably selected from the immunoglobulin superfamily. Thus, each protein molecule is homologous to the other molecules of the composition, but also contains one or more stretches of variable polypeptide sequence, which is/are characterized by differences in the amino acid sequence between the individual members of the polyclonal protein. Known examples of such polyclonal proteins include antibody or immunoglobulin molecules, T cell receptors and B cell receptors. A polyclonal protein may consist of a defined subset of protein molecules, which has been defined by a common feature such as the shared binding activity towards a desired target, e.g. a polyclonal antibody exhibiting binding specificity towards a desired target antigen.

The term "a population of genetically diverse cells" as used herein, refers to a cell population where the individual cells in the population differ among each other on the genomic level. Such a population of genetically diverse cell is for example a population of cells derived from a donor, or a fraction of such cells, e.g. a B lymphocyte or a T lymphocyte containing cell fraction.

The term "primer set" is used interchangeably with the term "primer pair" and describes two or more primers which together are capable of priming the amplification of a nucleotide sequence of interest (i.e., one member of a cognate pair). A primer set of the present invention may be designed to prime a family of nucleotide sequences containing variable region encoding sequences. Examples of different families are antibody kappa light chains, lambda light chains, heavy chain variable regions, and α, β, γ, or δ cell receptor variable regions. A primer set for the amplification of a family of nucleotide sequences containing variable region encoding sequences often constitutes a plurality of primers where several primers can be degenerate primers.

The term "sequence identity" is expressed as a percentage which indicates the degree of identity between to nucleic acid sequences over the length of the shortest of the two sequences. It can be calculated as $(N_{ref} - N_{dif}) \times 100\% / N_{ref}$, wherein $N_{ref}$ is the number of residues in the shorter of the sequences, and wherein $N_{dif}$ is the total number of non-identical residues in an $N_{ref}$ long optimally aligned match between the two sequences. Hence, the DNA sequence AGTCAGTC (Seq. no. 32) will have a sequence identity of 0.75% with the sequence TAATCAATCGG (Seq. no. 33) ($N_{dif}=2$ and $N_{ref}=8$) (underlining shows the optimal alignment, and bold indicates the two non-identical residues out of 8).

The terms "randomly" or "random" with respect to linkage refers to linkage of nucleotide sequences which are not derived from the same cell but are linked transversely among a population of genetically diverse cells. If the nucleotide sequences of interest are variable region encoding sequences, this will result in a combinatorial library of linked sequences. If, on the other hand, the nucleotide sequences of interest encode for a non-diverse heteromeric protein the randomly linked sequences will appear similar to sequences linked from a single cell.

The term "template derived from an isolated single cell," with regard to reverse transcription, relates to the nucleic acids within such an isolated cell. The nucleic acids can for example be in the form of RNA, mRNA, DNA or genomic DNA. The nucleic acids can either be isolated from the cell or still be with the remaining contents of the cell, where the cell is in an intact form or a lysed form.

The term "CD43" refers to a mouse surface antigen known under numerous synonyms including 3E8 antigen, A630014B01Rik, B cell differentiation antigen LP-3, Cd43, CD43 antigen, Galgp, Leucocyte sialoglycoprotein, leukosialin, Leukosialin precursor, Ly48, Ly-48, Sialophorin, as well as to orthologous surface markers from other animals.

The term "CD138" refers to a mouse surface antigen known under numerous synonyms including Syndecan-1, AA408134, AA409076, CD138, syn-1, Synd, Synd1, SYND1, Synd-1, Syndecan-1 precursor as well as to orthologous surface markers from other animals.

The term "MHCII" refers to a mouse surface antigen known under numerous synonyms including CD74 antigen, CLIP, DHLAG, H-2 class II histocompatibility antigen gamma chain, HLADG, HLA-DR-GAMMA, Ia antigen-associated invariant chain, Ia-GAMMA, Ii, MHC class II-associated invariant chain as well as to orthologous surface markers from other animals.

The term "B220" refers a mouse surface antigen known under numerous synonyms including B220, Cd45, CD45, CD45 antigen, CD45R, L-CA, Leukocyte common antigen precursor, loc, Ly-5, Lymphocyte common antigen Ly-5, Lyt-4, T200 as well as to orthologous surface markers from other animals.

DETAILED DESCRIPTION OF THE INVENTION

The Amplification and Linkage Process

One feature of the present invention reduces the number of tubes necessary to amplify the nucleotide sequences of interest, utilizing a variant of PCR in which two or more target sequences are amplified simultaneously in the same tube, by including more than one set of primers, for example all the primers necessary to amplify variable region encoding sequences, in the same reaction. Generally this approach is known as multiplex polymerase chain reaction (multiplex PCR).

A further feature of the present invention is that two or more target sequences amplified by multiplex PCR are linked in close proximity to the amplification process. In particular cognate pairs of variable region encoding sequences are linked by this process.

One embodiment of the present invention exploits that a multiplex primer mix can be designed to work in an overlap-extension PCR procedure, resulting in a simultaneous amplification and linkage of nucleotide sequences of interest. This multiplex overlap-extension PCR technique serves to reduce the number of reactions necessary to isolate and link nucleotide sequences of interest, in particular cognate pairs of linked variable regions.

Other embodiments of the present invention apply linkage by ligation or by recombination as an alternative to linkage by multiplex overlap-extension PCR. In these procedures, the linkage is not performed simultaneously with the multiplex PCR amplification, but as an immediate step following the amplification. However, linkage can still be performed in the same tube as the multiplex PCR was performed in.

A multiplex overlap-extension PCR requires the presence of two or more primer sets (a multiplex primer mix), where at least one primer of each set is equipped with an overlap-extension tail. The overlap-extension tails enable the linkage of the products generated by each of the primer sets during amplification. Such a primer mix is called a multiplex overlap-extension primer mix. The multiplex overlap-extension PCR, differ from conventional overlap-extension PCR in that the sequences to be linked are generated simultaneously in the same tube, thereby providing immediate linkage of the target sequences during amplification, without any intermediate purification.

A further feature of the present invention is a reverse transcription (RT) step preceding the multiplex PCR or multiplex overlap-extension PCR amplification, utilizing a template derived from an isolated single cell or a population of isogenic cells.

A further feature of the present invention is the use of nucleotide sequences derived from an isolated single cell or a population of isogenic cells as template for the multiplex PCR amplification. Preferably, RNA from a single cell is reverse transcribed into cDNA prior to the multiplex PCR. For the amplification of some nucleic acid sequences of interest genomic DNA may be used as an alternative to mRNA. By using isolated single cells or a population of isogenic cells derived by clonal expansion of an isolated single cell as template source, it is possible to avoid scrambling of nucleotide sequences encoding a heteromeric protein of interest, with nucleotide sequences derived from different cells within a population of cells. This is of importance if one wishes to obtain the original composition of the sequences of interest. Especially for the generation of a cognate pair of variable region encoding sequences, the use of an isolated single cell or a population of isogenic cells as template source is an important feature.

Additionally, the present invention facilitates the generation of libraries of linked nucleic acid sequences of interest, in particular combinatorial libraries and libraries of cognate pairs of variable regions. Further, the present invention utilizes nucleic acids derived from single cells, preferably in the form of RNA that does not need to be isolated from the remaining cell contents before it can be utilized as template.

One embodiment of the present invention encompasses the linkage of a plurality of non-contiguous nucleotide sequences of interest. The method comprises amplifying, in a multiplex PCR or multiplex RT-PCR amplification procedure, nucleotide sequences of interest using a template derived from an isolated single cell or a population of isogenic cells and effecting linkage of the amplified nucleotide sequences of interest. Further, the method comprises an optional step of performing an additional amplification of the linked products.

A further embodiment of the present invention encompasses a method of producing a library of cognate pairs comprising linked variable region encoding sequences. The method comprises providing a lymphocyte-containing cell fraction from a donor, which is optionally enriched for a particular lymphocyte population from said cell fraction, or wherein a particular lymphocyte population has been isolated from said cell fraction. Further, a population of isolated single cells is obtained by distributing cells from the lymphocyte-containing cell fraction, or the enriched cell fraction, individually among a plurality of vessels. Multiplex molecular amplification (multiplex RT-PCR amplification) of the variable region encoding sequences contained in the population of isolated single cells is performed and linkage of pairs of variable region encoding sequences is effected, wherein an individual pair of variable region sequences is derived from a single cell, within the population of isolated single cell. Further, the technique comprises two optional steps: in the first step the individual isolated single cell in the population of single cells is expanded to a population of isogenic cells prior to performing multiplex RT-PCR amplification. Thereby obtaining a plurality of vessels with a diverse population of isogenic cells (one population of isogenic cells in one vessel). The second optional step encompasses performing an additional amplification of the linked variable region encoding sequences.

In preferred embodiments of the present invention, an individual member of said library of cognate pairs comprised of an immunoglobulin light chain variable region encoding sequence is associated with an immunoglobulin heavy chain variable region encoding sequence, originating from the same cell or of sequences encoding a T cell receptor binding domain, constituted of an alpha chain variable region associated with a beta chain variable region or a gamma chain variable region associated with a delta chain variable region, where the associated variable regions originate from the same cell.

The multiplex RT-PCR amplification of the present invention can be performed either as a two-step process, where reverse transcription (RT) is performed separate from the multiplex PCR amplification (or alternative multiplex molecular amplification), or as a single-step process, where the RT and multiplex PCR amplification steps are performed with the same primers in one tube.

The reverse transcription (RT) is performed with an enzyme containing reverse transcriptase activity resulting in the generation of cDNA from total RNA, mRNA or target specific RNA from an isolated single cell. Primers which can be utilized for the reverse transcription are for example oligo-dT primers, random hexamers, random decamers, other random primers, or primers that are specific for the nucleotide sequences of interest.

The two-step multiplex RT-PCR amplification procedure, allows for the cDNA generated in the RT step, to be distributed to more than one vessel permitting for the storage of a template fraction before proceeding with the amplification. Additionally, the distribution of cDNA to more than one tube, allows for the performance of more than one multiplex PCR amplification of nucleic acid derived from the same template. Although, this results in an increased number of separate reactions, it opens for the possibility to decrease the complexity of the multiplex primer mix if this should be desired. This two-step approach can for example be applied to amplify and link heavy chain variable region and kappa light chain variable region encoding sequences in one tube and heavy chain variable region and lambda light chain variable region encoding sequences in a different tube utilizing the same template. A single cell usually only expresses one of the light chains. However, it will often be easier to perform the reactions simultaneously instead of awaiting the result of one of the reactions before performing the other. Further, the amplification of both kappa and lambda serves as an internal negative control, since it would be expected that only kappa or lambda amplify from a single cell.

In the single-step multiplex RT-PCR procedure, reverse transcription and multiplex PCR amplification is carried out in the same vessel. All the components necessary to perform both the reverse transcription and the multiplex PCR in a single step are initially added into the vessels and the reaction is performed. Generally, there is no need to add additional components once the reaction has been started. The advantage of single-step multiplex RT-PCR amplification is that it reduces the number of steps necessary to generate the linked nucleotide sequences of the present invention even further. This is particularly useful when performing multiplex RT-PCR on an array of single cells, where the same reaction needs to be carried out in a plurality of vessels. Single-step multiplex RT-PCR is performed by utilizing the reverse primers present in the multiplex primer mix needed for the multiplex PCR amplification as primers for the reverse transcription as well. Generally, the composition needed for the single-step multiplex RT-PCR comprises a nucleic acid template, an enzyme with reverse transcriptase activity, an enzyme with DNA polymerase activity, deoxynucleoside triphosphate mix (dNTP mix comprising dATP, dCTP, dGTP and dTTP) and a multiplex primer mix. The nucleic acid template is preferably total RNA or mRNA derived from an isolated single cell either in a purified form, as a lysate of the cell or still within the intact cell. Generally, the exact composition of the reaction mixture requires some optimization for each multiplex primer mixture to be used with the present invention. This applies both for the two-step and the single-step multiplex RT-PCR procedures.

For some single-step multiplex RT-PCR reactions it may be an advantage to add additional components during the reaction. For example, addition of the polymerase following the RT step. Other components could for example be a dNTP mixture or a multiplex primer mix possibly with a different primer composition. This can then be considered as a one-tube multiplex RT-PCR, which generally has the same advantages as the single-step multiplex RT-PCR, since it also limits the number of tubes necessary to obtain the desired linked products.

The nucleotide sequences of interest, amplified by the multiplex RT-PCR, can be linked to one another by several methods, such as multiplex overlap-extension RT-PCR, ligation or recombination, using different multiplex primer mixes. Preferably the multiplex RT-PCR amplification and linkage process is a single step or a two step process. However, the linkage process may also be performed as a multi step process, using for example a stuffer fragment to link the nucleic acid sequences of interest, either with PCR, ligation or recombination. Such a stuffer fragment may contain cis-elements, promoter elements or a relevant coding sequence or recognition sequence. In a preferred embodiment the linkage process is performed in the same vessel as the multiplex RT-PCR amplification.

In one embodiment of the present invention the linkage of a plurality of non-contiguous nucleotide sequences of interest is performed in association with the multiplex PCR amplification, utilizing a multiplex overlap-extension primer mix. This results in the combined amplification and linkage of the target sequences. Generally, the composition needed for the multiplex overlap-extension PCR comprises, a nucleic acid template, an enzyme with DNA polymerase activity, deoxynucleoside triphosphate mix (dNTP mix comprising dATP, dCTP, dGTP and dTTP) and a multiplex overlap-extension primer mix.

In a particular embodiment of the present invention, the linkage of a plurality of non-contiguous nucleotide sequences of interest is performed by multiplex overlap-extension RT-PCR using a template derived from an isolated single cell or a population of isogenic cells. Further, the method comprises an optional step of performing an additional molecular amplification of linked products. Preferably, the multiplex overlap-extension RT-PCR is performed as a single-step/one-tube reaction.

A multiplex overlap-extension primer mix of the present invention comprises at least two primer sets capable of priming the amplification and linkage of at least two variable region encoding sequences, for example, amplification and linkage of sequences from immunoglobulin heavy chain variable region families with kappa or lambda light chain variable region families, or amplification and linkage of sequences from T cell receptor families α, β, γ, or δ.

In another embodiment of the present invention the plurality of nucleotide sequences of interest, amplified by multiplex RT-PCR, are linked by ligation. To achieve this, the multiplex primer mix used for the multiplex RT-PCR, is designed such that the amplified target sequences can be cleaved with appropriate restriction enzymes, and covalent linkage by DNA ligation can be performed (the primer design is described in the section "Primer Mixtures and Design"). Following multiplex RT-PCR amplification with such a multiplex primer mix, the restriction enzymes needed to form compatible ends of the target sequences, are added to the mixture together with the ligase. No purification of the PCR products is needed prior to this step, although purification may be performed. The reaction temperature for the combined restriction cleavage and ligation is approximately between 0 and 40° C. However, if the polymerase from the multiplex PCR reaction is still present in the mixture, an incubation temperature below room temperature is preferred, most preferred are temperatures between 4 and 16° C.

In yet another embodiment of the present invention, the plurality of nucleotide sequences of interest, amplified by multiplex RT-PCR, are linked by recombination. In this approach, the target sequences amplified can be joined using identical recombination sites. Linkage is then performed by adding the recombinases facilitating recombination. Some suitable recombinase systems are Flp recombinase with a variety of FRT sites, Cre recombinase with a variety of lox sites, integrase ΦC31 which carries out recombination between the attP site and the attB site, the β-recombinase-six system as well as the Gin-gix system. Linkage by recombination has been exemplified for two nucleotide sequences ($V_H$ linked with $V_L$) (Chapal, N. et al. 1997 BioTechniques 23, 518-524).

In a preferred embodiment of the present invention, the nucleotide sequences of interest comprise variable region encoding sequences and the linkage generates a cognate pair of variable region encoding sequences. Such a cognate pair may comprise one or more constant region encoding sequences in addition to the variable regions. Preferably the constant regions are of human origin and the variable region cognate pair is of different origin, such as mouse, rat, or rabbit.

In an even more preferred embodiment of the present invention, the nucleotide sequences of interest comprise immunoglobulin variable region encoding sequences and the linkage generates a cognate pair of light chain variable region and heavy chain variable region encoding sequences. Such a cognate pair may comprise one or more constant region encoding sequences in addition to the variable regions. Further, such a cognate pair may be isolated from template derived from cells of the B-lymphocyte lineage enriched from a lymphocyte-containing cell fraction, such as whole blood, mononuclear cells or white blood cells.

In another embodiment of the present invention, the nucleotide sequences of interest comprise TcR variable region encoding sequences and the linkage generates a cognate pair of α chain variable region and β chain variable region encoding sequences or γ chain variable region and δ chain variable region encoding sequences. Such a cognate pair may comprise one or more constant region encoding sequences in addition to the variable regions. Further, such a cognate pair may be isolated from template derived from cells of the T-lymphocyte lineage enriched from a lymphocyte-containing cell fraction, such as whole blood, mononuclear cells or white blood cells.

Another aspect of the present invention, is to utilize the multiplex RT-PCR with a population of genetically diverse cells as template source. The majority of heteromeric protein encoding sequences do not vary from cell to cell as is the case with variable region encoding sequences from binding proteins. Thus, when utilizing the present invention for the cloning of such non-variable heteromeric protein encoding sequences there is no need to perform an initial isolation of single cells.

In this embodiment of the present invention, a plurality of non-contiguous nucleotide sequences of interest are linked randomly by a method comprising, performing multiplex RT-PCR amplification of nucleotide sequences of interest using a template derived from a population of genetically diverse cells and effecting linkage of the amplified nucleotide sequences of interest. Further, the method comprises an optional step of performing an additional amplification of the linked products. As with the single cell approach the linkage can either be performed utilizing a multiplex overlap-extension primer mix for the amplification or alternatively by ligation or recombination. Preferably the template derived from the population of cells is not strictly contained within the cells. The population of cells may for example be lysed.

Application of the process of random linkage on a population of cells expressing variant binding proteins, allows for a simplified generation of combinatorial libraries of variable region encoding sequences. Preferably, the population of cells constitutes cells that express variable region binding proteins, such as B lymphocytes, T lymphocytes, hybridoma cells, plasma cells, plasmablasts, or a mixture of these cells.

The population of cells in the above mentioned embodiment can for example be permeabilized or lysed, without additional purification, or the template nucleic acids can be isolated from the cells by standard procedures. The single-step multiplex RT-PCR procedure is preferred. However, the two-step procedure may also be used in the embodiment.

An efficient way to increase the specificity, sensitivity, and yield of the multiplex RT-PCR-linkage process, is by performing an additional molecular amplification of the linked nucleotide sequences obtained from the multiplex RT-PCR followed by linkage by ligation or recombination or linkage using the multiplex overlap-extension RT-PCR. This additional amplification is preferably performed with PCR amplification, utilizing a primer mix adapted for amplifying the linked nucleic acid sequences of interest. The primer mix utilized may be the outer primers of the multiplex primer mix or multiplex overlap-extension primer mix, meaning the primers which anneal to the outermost 5' end and 3' end of the sense strand of the linked variable region encoding sequences, thereby enabling the amplification of the entire linked product. The outer primers can also be described as the primers of the multiplex overlap-extension primer mixture that do not contain overlap extension tails. Alternatively, a nested or semi-nested primer set can be used for the additional amplification of the linked nucleotide sequences. Such a nested PCR especially serves to increase the specificity of the method as well as to increase the amount of linked product. For the present invention, semi-nested PCR (as described in the section entitled Primer Mixtures and Design) is considered to function as well as the nested PCR. Thus, it is desired although not necessary for the present invention to perform an additional PCR amplification of the linked products from the multiplex overlap-extension RT-PCR or of the products linked by ligation or recombination, preferably using nested PCR or semi-nested PCR.

The additional amplification can either be performed directly using a fraction or the entire multiplex overlap-extension RT-PCR reaction product or ligation product or recombination product, or a fraction of any one of these products or using partially purified linked products from any one of these reactions, e.g. by performing an agarose gel electrophoresis of the linked products, and excising the fragment corresponding to the expected size of the linked variable region encoding sequences. For products linked by multiplex overlap-extension RT-PCR, the additional amplification is preferably performed directly on a fraction from the multiplex overlap-extension RT-PCR reaction, since this would assist linkage of the individual target sequences that were not linked in the first reaction.

Sequences of Interest

The nucleotide sequences of interest of the present invention can be selected from sequences that encode different subunits or domains, which when expressed, forms a protein or part of a protein. Such proteins that are composed of at least two non-identical subunits are known as heteromeric proteins. Heteromeric proteins are common in all kinds of species. Some of the classes to which such proteins belong are for example enzymes, inhibitors, structural proteins, toxins, channel proteins, G-proteins, receptor proteins, immunoglobulin superfamily proteins, transportation proteins etc. The nucleotide sequences encoding such heteromeric proteins are non-contiguous, meaning for example that they originate from different genes, or different mRNA molecules. However, non-contiguous as used in the present invention may also mean nucleotide sequences encoding domains of the same protein, where the domains are separated by nucleotide sequences which are not of interest.

In one embodiment of the present invention the nucleotide sequences of interest contain variable region encoding sequences from the immunoglobulin superfamily, such as immunoglobulins (antibodies), B cell receptors and T cell receptors (TcR's). Especially variable region encoding sequences from immunoglobulins are of interest. Such variable region encoding sequences comprise full-length antibodies as well as Fab's, Fv's, scFv's and combinations of fragments of the variable region encoding sequences, e.g. complementarity determining regions (CDR's), joining genes or V-genes or combinations of these. Generally the present invention can be applied with any combinations of variable region encoding sequences and fragments thereof. The present application enables the linkage of only the variable domains of the heavy and light chains generating Fv or scFv encoding sequences. Or the linkage of the entire light chain with the heavy chain variable region+constant region domain $C_{H1}$+parts of the hinge region, generating Fab, Fab' or $F(ab)_2$. Further, it is possible to add any region of the heavy chain constant region domains to the variable heavy chain, thereby generating full-length antibody encoding sequences or truncated antibody encoding sequences. In one aspect of the invention the non-human variable sequences are linked to human constant regions to generate full chimeric human/non-human antibodies, preferably chimeric antibodies with human constant regions.

In a further embodiment of the present invention variable region encoding sequences comprise one type of immunoglobulin light chain (kappa or lambda) encoding sequence and one immunoglobulin heavy chain variable region encoding sequence. This is achieved by selecting primers amplifying only one isotype of light and heavy chain. The isotype can also be determined by linking or splicing human constant regions from one or more particular isotypes of heavy and light chain.

Variable region encoding sequences derived from T cell receptors (TcR's) are also of interest. Such TcR encoding sequences comprise encoding sequences for full-length alpha and beta chains or gamma and delta chains as well as soluble TcR's or only the variable domains of these chains or single chain fusion proteins thereof (e.g. single chain αβ or single chain γδ).

Template Sources

One feature of the present invention is the ability to link nucleotide sequences derived from an isolated single cell, a population of isogenic cells, or a genetically diverse population of cells which have not been separated into single vessels.

A preferred feature of the present invention is the use of isolated single cells or a population of isogenic cells as template source, since scrambling of the nucleic acid sequences of interest, in particular variable region encoding sequences is avoided. This is of importance if one wishes to obtain an original pair of for example variable region encoding sequences.

Another preferred feature of the present invention, is obtaining a single cell or population of single cells from a cell fraction comprising lymphocytes, such as B lymphocytes, T lymphocytes, plasma cells and/or various developmental stages of these cell lineages. Other populations of cells that express binding proteins from the immunoglobulin superfamily might also be used to obtain single cells. Cell lines such as hybridoma cells, cell lines of B lymphocyte or T lymphocyte lineage or virus immortalized cell lines or donor derived cells participating in the immune response are also applicable in the present invention. Donor derived lymphocyte-containing cell fractions may be obtained from natural tissue or fluid which is rich in such cells, e.g. blood, bone marrow, lymph nodes, spleen tissue, tonsil tissue or from infiltrations in and around tumors or inflammatory tissue infiltrations. Preferably, in the case of non-human animals, spleen tissue or bone marrow is used. Donors can either be naïve or hyperimmune with respect to a desired target. For the isolation of antigen binding proteins with binding specificities toward a desired target, hyperimmune donors are preferred. Such hyperimmune donors can either be donors immunized with the target, or fragments of the target, or it can be convalescent patients, or non-healthy individuals which are running a natural immune response towards the target e.g. autoimmune patients, cancer patients, patients with infectious diseases e.g. HIV patients, Hepetitis A, B or C patients, SARS patients etc., or patients with chronic diseases. However, in a particularly preferred embodiment, the donor is a non-human animal that has been immunised with a human self-antigen, such as a human protein implicated in cancer, such as EGFR.

For use in the present invention, cell donors may be of the same species as the species to be treated with the products obtainable from the linked nucleotide sequences of the present invention. Preferably, a cell donor is a domestic animal, a pet, a human. A special feature of the present invention is that it enables the generation of chimeric human/non-human antibody libraries for generation of chimeric antibodies for use in human therapy. Such an approach is preferred when the antibodies are directed against so-called self-antigens, i.e. human antigens.

The donor may also be a transgenic animal, in particular a transgenic mouse. Transgenic animals carrying human immunoglobulin loci are described in U.S. Pat. No. 6,111,166 and Kuroiwa, Y. et al. Nature Biotechnology; 2002; 20: 889-893. Such transgenic animals are capable of producing human immunoglobulins. Thus, fully human antibodies against a specific target can be raised by usual immunization techniques of such transgenic animals. This allows for generation of libraries encoding for binding proteins with specificities towards more difficult targets such as human antigens to which no or limited natural human antibody response exist. Such transgenic animals can likewise be developed to produce human T cell receptors.

In a further embodiment of the present invention, the lymphocyte-containing cell fraction is constituted of whole blood, bone marrow, mononuclear cells, or white blood cells obtained from a donor. Mononuclear cells can be isolated from blood, bone marrow, lymph nodes, spleen, infiltrations around cancer cells and inflammatory infiltrations. Mononuclear cells can be isolated by density centrifugation techniques, e.g. Ficoll gradients. If the mononuclear cells are isolated from samples composed of tissue, the tissue is disintegrated before the gradient centrifugation is performed. Disintegration can be performed, for example, by mechanical methods such as grinding, electroporation and/or by chemical methods such as enzymatic treatments. The isolation of white blood cells can be performed directly from donors using leukopheresis. Raw preparations of for example bone marrow or tissue, which contain lymphocytes, can also be used in the present invention. Such preparations will need to be disintegrated, for example as described above, in order to facilitate single cell distribution.

A further feature of the present invention is enrichment of the lymphocyte-containing cell fraction e.g. whole blood, mononuclear cells, white blood cells or bone marrow, with respect to a particular lymphocyte population, such as cells from the B lymphocyte or T lymphocyte lineage. Enrichment of B lymphocytes can for example be performed, using magnetic bead cell sorting (MACS) or fluorescence activated cell sorting (FACS) taking advantage of lineage-specific cell surface marker proteins such as CD19 or other B cell lineage-specific markers such as B220. Enrichment of T lymphocytes can for example be performed, utilizing a cell surface marker such as CD3 or other T cell lineage-specific markers.

A preferred feature of the present invention is to sort the enriched B lymphocytes further in order to acquire plasma cells, before distributing the cells individually among a plurality of vessels. Isolation of plasma cells is generally performed by MACS sorting or FACS sorting, utilizing surface markers such as CD19. Other plasma cell-specific surface markers or combinations thereof can be utilized as well, for example CD138, CD43, CD19, MHC-II, the exact choice of marker depends on the plasma cell source, e.g. spleen, tonsils, blood or bone marrow. Of course, the exact choice of surface markers also depends on the species, from which the cells are isolated.

In one aspect of the invention, the markers used for sorting and/or selection of cells are CD43 and CD138 or MHCII and B220 or orthologs. Preferably, the combination of markers is CD43 and CD138, and preferably the selected cells have an intermediate or high expression of these markers relatively to the lymphocytec-comprising cell population from which they are selected or isolated. More preferably the level of expression of CD43 and CD138 is high relatively to the lymphocyte-comprising cell population from which they are selected or isolated.

Plasma cells can also be obtained from a non-enriched lymphocyte-containing cell population obtained from any of these sources. The plasma cells isolated from blood are sometimes called early plasma cells or plasmablasts. In the present invention these cells are also termed plasma cells. Plasma cells are desired for the isolation of cognate pairs of immunoglobulin encoding sequences because a higher frequency of these cells produces antigen-specific antibodies that reflect the acquired immunity toward the desired antigen and most of the cells have undergone somatic hypermutation and therefore encode for high-affinity antibodies. Further, the mRNA levels in plasma cells are elevated compared to the remaining B lymphocyte population, thus the reverse transcription procedure is more efficient when using single plasma cells. As an alternative to plasma cell isolation, memory B cells may be isolated from a lymphocyte containing cell fraction utilizing a cell surface marker such as CD27 and IgG.

An alternative feature of the present invention, is selecting the enriched B lymphocytes for antigen specificity before distributing the cells among a plurality of vessels. Isolation of antigen-specific B lymphocytes is performed by contacting the enriched B lymphocytes with the desired antigen or antigens enabling binding of antigen to surface exposed immunoglobulin, followed by isolation of binders. This can be done, for example, by biotinylation of the desired antigen or antigens followed by suitable cell sorting techniques. Plasma cells as well as B lymphocytes, non-enriched mononuclear cells, white blood cells, whole blood, bone marrow or tissue preparations can be subjected to isolation with respect to antigen specificity if this is desired.

Another feature of the present invention, is to sort enriched T lymphocytes (e.g. CD3 positive cells) using surface markers such as e.g. CD27 to obtain a fraction of memory T cells. T lymphocytes can also be selected for MHC-antigen specificity using MHC-peptide complexes (e.g. Callan, M. F. et al. 1998. J. Exp. Med. 187, 1395-1402; Novak, E. J. et al. 1999. J. Clin. Invest 104, R63-R67).

As an alternative to sorting cells expressing certain surface markers, i.e. a positive selection, it is conceivable that cells NOT expressing the markers are depleted from the composition of cells, leaving the cells behind that actually express the markers.

A further feature of the present invention is immortalization of any of the isolated cell fractions described in the above (e.g. B lymphocytes, plasma cells, memory cells or T lymphocytes). Immortalization may for example be performed with Epstein-Barr virus (Traggiai, E., et al., 2004. Nat Med 10, 871-875) prior to cell distribution. Alternatively, isolated single cells may be immortalized and expanded prior to reverse transcription. Traggiai et al., Nat. Med. 2004 August; 10(8):871-5.

A further feature of the present invention, is the distribution of a population of desired cells (e.g. hybridoma cells, cell lines of B lymphocyte or T lymphocyte lineage, whole blood cells, bone marrow cells, mononuclear cells, white blood cells, B lymphocytes, plasma cells, antigen-specific B lymphocytes, memory B cells, T lymphocytes, peptide/MHC-specific T lymphocytes, or memory T cells) individually, into a plurality of vessels, in order to obtain a population of isolated single cells. This isolation of single cells refers to the physical separation of cells from a population of cells in such a way that a single vessel contains a single cell, or a micro array, chip or gelmatrix is loaded in a manner that produce single cells. The cells may be distributed directly into multitudes of vessels such as arrays of single vessels by limiting dilution. The single vessels utilized in the present invention are preferably those applicable in PCR (e.g. PCR tubes and 96 well or 384 well PCR plates or larger arrays of vessels). However other vessels may also be used. When distributing single cells into a large number of single vessels (e.g. 384 well plates), a population of single cells is obtained. Such a distribution may be performed, for example, by dispensing a volume into a single vessel that on average encompasses a cell concentration of one, 0.5 or 0.3 cell, thereby obtaining vessels that on average contain a single cell or less. Since distribution of cells by limiting dilution is a statistical event, a fraction of the vessels will be empty, a major fraction will contain a single cell, and a minor fraction will contain two or more cells. Where two or more cells are present in a vessel some scrambling of the variable region encoding sequences may occur among the cells present in the vessel. However, since it is a minor event it will not affect the overall utility of the present invention. Additionally, combinations of variable region encoding sequences which do not posses the desired binding affinity and specificity will most likely not be selected and hence eliminated during a screening process. Therefore, minor events of scrambling will not significantly affect the final library of the present invention.

There are alternatives to cell distribution by limiting dilution using, for example, cell sorters such as FACS machines or robots that can be programmed to accurately dispense single cells into single vessels. These alternatives are preferable, since they are less laborious and are more efficient in uniformly obtaining a distribution of single cells into single vessels.

The enrichment, sorting and isolation procedures described in the above, are performed such that the majority of the cells are kept intact. Rupture of cells during enrichment and sorting might result in scrambling of the variable region encoding sequences. However, this is not expected to be a problem since the frequency of rupture is expected to be low. Washing and possible RNAse treatment of the cells prior to distribution into single vessels will remove any RNA that has leaked during the process.

Further, when considering the above descriptions of how to distribute cells in order to obtain a population of single cells in a population of single vessels, it is not to be interpreted as an absolutely required feature that every vessel must contain a single cell. Rather, it indicates that a majority of the vessels contain single cells, e.g. the number of vessels with two or more cells is below 25% of the total amount of cells distributed, or even better it is below 10%.

A further feature of the present invention is the performance of a reverse transcription using template derived from cells distributed individually among a plurality of vessels.

For the purpose of reverse transcription (RT), in accordance with the present invention, the nucleic acids within a single cell that is to serve as template source for the RT, are considered to be derived from a single cell although they have not necessarily been separated from the remaining contents of that single cell.

When the final distribution of the single cells to their single vessels has been performed, the single cells may be expanded in order to obtain a population of isogenic cells prior to reverse transcription. This process yields more mRNA to be used as template, which might be important if a rare target is to be amplified and linked. However, the cells should remain genetically identical with respect to the target gene during the expansion. The isolated cells or the population of isogenic cells can either be kept intact or lysed, as long as the template for the reverse transcription is not degraded. Preferentially, the cells are lysed in order to ease the following reverse transcription and PCR amplification.

In a different embodiment of the present invention, the disclosed multiplex overlap-extension RT-PCR method or multiplex RT-PCR followed by linkage by ligation or recombination may also be utilized on template derived from a genetically diverse population of cells which have not been separated into single vessels, but all remain together as a pool of cells. This method may be used for the generation of combinatorial libraries. Such an approach will not require the distribution of single cells. However, the cells which may be used in this approach are the same as those described for the single cell approach, for example a population (pool) of sorted B lymphocytes or T lymphocytes. When performing the single-step multiplex overlap-extension RT-PCR or single-step multiplex RT-PCR followed by linkage by ligation or recombination on such a population of cells, it is preferable to lyse the cells prior to the reaction and if desired total RNA or mRNA may be isolated from the lysate.

The sensitivity of the single-step multiplex overlap-extension RT-PCR of the present invention enables the use of a very low amount of template, e.g. an amount of template corresponding to the lysate of a single cell.

Primer Mixtures and Design

The primer mixtures of the present invention comprise at least four primers that form primer sets two by two, which are capable of amplifying at least two different target sequences of interest. Mixtures of two or more of such primer sets constitute a multiplex primer mix. Preferably, a multiplex mix comprise at least 3, 4, 5, 6, 7, 8, 9, 10, 11, 12, 13, 14, 15, 16, 17, 18, 19 or 20, 30, 40, 50, 60, 70, 80, 90 100, 110, 120, 130, 140 or 150 primer sets (primer pairs). In particular for the amplification of variable region encoding sequences, may an individual primer set within the multiplex primer mix constitute several more than two primers. Preferably, an individual primer set comprises at least 3, 4, 5, 6, 7, 8, 9, 10, 11, 12, 13, 14, 15, 20, 25, 30, 35, 45, 50, 60, 70, 80, 90, 100, 110, 120, 130, 140, 150, 160, 170, 180, 190, 200, 220, 240, 260, 280 or 300 primers. Preferably the total number of primers in a multiplex primer mix is at least 5, 6, 7, 8, 9, 10, 11, 12, 13, 14, 15, 20, 25, 30, 35, 45, 50, 60, 70, 80, 90, 100, 125, 150 or 200 and at the most 225, 250, 275, 300, 325, 350, 375 or 400 primers.

All the primers of the present invention comprise a gene-specific region, and preferably all primers are additionally equipped with a primer tail at the 5' end of the primer, i.e. 5' non-coding sequences which is fused to the 3' end of the gene-specific primer part. Such a primer tail is approximately from 6 to 50 nucleotides long, but it may also be longer if desired. Upon amplification the primer tails are added to the target sequences.

Primer tails of the present invention are for example, cloning tails and linkage tails such as, tails adapted for linkage by ligation, tails adapted for linkage by recombination or overlap-extension tails.

Cloning tails may be from 6 to 20 nucleotides long or longer and comprise restriction sites and/or recombination sites, which are useful for the insertion of the linked product into an appropriate vector.

To enable linkage by ligation, the primer sets of the multiplex primer mix are designed such that one part (forward or reverse primer(s)) of the first primer set is equipped with a linkage-tail containing a restriction site that upon cleavage will be compatible with a restriction site located in the linkage tail of one part of the second primer set. For linkage of more than two target sequences, the second part of the second primer set is equipped with a restriction site that upon cleavage will be compatible with a restriction site located in one part of the third primer set. This second restriction site located in the second primer set should be non-compatible with that of the first primer set. A considerable number of target sequences can be linked by designing primer sets this way. Restriction sites with a low frequency or no occurrence, in the target sequences should be chosen. Further, it is preferable that compatible restriction sites are not identical, such that the site of ligation becomes cleavage-resistant for the particular restriction enzymes used. This will drive the reaction towards linkage of target sequence one with target sequence two, since linkage between identical target sequences will be cleavable by the restriction enzymes. Suitable pairs of restriction sites are for example, SpeI with XbaI (alternatively NheI or AvrII can substitute one or both of these), NcoI with BspHI, EcoRI with MfeI or PstI with NsiI. For linkage, SpeI can for example be located in target sequence one, XbaI can be located in target sequence two, NcoI can be located at the other end of target sequence two and BspHI in target sequence three and so forth. To simplify the process further, it is an advantage if the restriction enzymes function in the same buffer.

To enable linkage by recombination the primer sets of the multiplex primer mix can for example be designed as exemplified in the article by Chapal (1997 BioTechniques 23, 518-524), which is hereby incorporated by reference.

To enable the linkage of the nucleotide sequences of interest in the same step as the multiplex PCR amplification, tails adapted for overlap-extension PCR are added to at least one primer of each primer set of the multiplex primer mix, thereby generating a multiplex overlap-extension primer mixture.

The overlap-extension tails are typically longer, ranging from 8 to 75 nucleotides in length and may contain restriction sites or recombination sites which allow for subsequent insertion of regulatory elements such as promoters, ribosomal binding sites, termination sequences, or linker sequences such as in a scFv. The overlap-extension tail may also contain a stop codon if that is desired. Generally there are three types of overlap-extension tails, as illustrated in FIG. 1 of WO 2005/042774. In type I the overlap-extension tails of two primer sets solely overlap with each other. Not necessarily all of the nucleotides of two overlap-extension tails are complementary to each other. In one aspect of the present invention the complementary nucleotides represent between 60 to 85% of the overlap-extension tail. In type II overlap-extension tails, 4 to 6 of the 5' nucleotides are complementary to the gene-specific region of the adjacent target sequence. In type III overlap-extension tails, the entire overlap is complementary to the adjacent target sequence. The type I and II overlap-extension tails are preferred when regulatory elements and the like are later to be inserted between the linked target sequences. Type II overlap-extension tails are preferred if the target sequences are to be linked by a defined linker as seen with scFv. Type III overlap-extension tails are preferred if the target sequences are to be linked in-frame to each other.

Design of overlap-extension tails is dependent on sequence features such as length, relative GC content (GC %), presence of restriction sites, palindromes, melting temperature, the gene-specific part to which they are coupled etc. The length of the overlap-extension tails should be between 8 and 75 nucleotides long, preferably they are from 15 to 40 nucleotides long. Even more preferred they are from 22 to 28 nucleotides long. The use of very long overlap-extension tails (50 to 75 nucleotides) could favor the linkage of the products produced by each primer set. However, the proportion between the length of the overlap-extension tail and the gene-specific region probably will need to be adjusted when using very long overlap-extension tails. The GC % preference is dependent on the length of the overlap-extension tail. Since shorter tails have a shorter area where they are complementary they need a higher GC % to strengthen the interaction than longer tails. Other principles of primer design should likewise be observed, e.g. primer dimerization and hairpin formation should be minimized. Neither shall they engage in false priming. Further, it is known that Taq DNA polymerase often adds an adenosine (A) at the 3' end of the newly synthesized DNA strand, and this can be accommodated for in overlap-extension tail design by enabling overlap-extension tails to accommodate 3' non-template A addition.

The choice of primers that carry the linkage tail, e.g. the overlap-extension tail, tail adapted for linkage by ligation or tail adapted for linkage by recombination, defines the order and direction of linkage of the target sequences. It is not essential to the invention whether it is the forward primer(s) or reverse primer(s) of a primer set or possibly both forward and reverse primers that are equipped with the linkage tail. However, some consideration should be given to this anyway since the order and direction of the target sequences in the final product might be of relevance e.g. for the insertion of regulatory elements such as promoters and termination sequences or for the in-frame linkage of the individual target sequences.

For the linkage of two nucleotide sequences of interest the linkage tail may be added either to the reverse primer(s) or forward primer(s) of each primer set used for the PCR amplification of each target sequence.

The present invention exemplifies addition of overlap-extension tails and tails adapted for linkage by ligation, to the mVH and mVK forward primers of each set. This results in a linking direction of the products that is 5' to 5' (head-to-head and bi-directional). However, linkage tails might as well be added to the reverse primer(s) of each set. This results in a linking direction of the product that is 3' to 3' (tail-to-tail and bi-directional). A third option is adding the linkage tails to the reverse primer(s) of the first primer set and the forward primer(s) of the second primer set or visa versa. This results in a 3' to 5' orientation (head-to-tail and uni-directional).

When linking more than two nucleotide sequences of interest some of the primer sets need to have linkage tails on both the forward and reverse primers, such that one tail is complementary to a tail of the preceding primer set and the other tail is complementary to one of the primers of the subsequent primer set. This principle holds for all the primer sets that amplify target sequences that are to be linked between two other target sequences.

The design of the gene-specific primer part generally should observe known primer design rules such as minimizing primer dimerization, hairpin formation and non-specific annealing. Further, multiple G or C nucleotides as the 3' bases are to be avoided when possible. The melting temperature (Tm) of the gene-specific regions in a primer set should preferably be equal to each other plus/minus 5° C. In the present invention Tm values between 45° C. and 75° C. are desirable and Tm values of about 60° C. are optimal for most applications. Advantageously, the initial primer design can be aided by computer programs developed for this task. However, primer designs generally need laboratory testing and routine optimization. This may be done, for example, by analyzing size, restriction fragment length polymorphism (RFLP) and sequencing of the amplification products obtained using the primer sets. The use of degenerate positions within primers is a useful approach when amplifying sequences with variable regions or when searching for new family members belonging to a specified class of proteins. The numbers of degenerate positions may also require optimization.

One feature of the present invention, are primer mixes composed of at least two primer sets that are able to prime amplification and promote linkage of at least two nucleotide sequences of interest. The primer mixes of the present invention are capable of priming the amplification of at least two subunits or domains from heteromeric proteins, e.g. belonging to the class of enzymes, inhibitors, structural proteins, toxins, channel proteins, G-proteins, receptor proteins, immunoglobulin superfamily proteins, transportation proteins etc, preferably immunoglobulins.

A further feature of the present invention is a multiplex overlap-extension primer mix comprising primer sets wherein at least one primer set member of each primer set comprises an overlap-extension tail capable of hybridizing to the overlap-extension tail of a primer set member of a second primer set.

The overlap-extension tails enables the immediate linkage of the nucleotides of interest during the multiplex overlap-extension PCR amplification by equipping each individual product arising from the primer sets with a tail that is complementary to an adjoining product. This however does not mean that the linkage necessarily occur during this first PCR amplification. Depending on the reaction setup, the majority of the actual linkage may be performed during an additional amplification with the outer primers of the first PCR amplification (multiplex PCR amplification).

A further feature of the present invention, is a primer set designed to amplify a family of nucleotide sequences containing variable region encoding sequences. Examples of such families are kappa light chains (e.g. VK1-19 in mice), lambda light chains (e.g. VL1-8 in mice) and variable heavy chains (e.g. VH1-15 in mice) from immunoglobulins, and α, β, γ or δ TcR variable regions. A primer set for the amplification of a family of nucleotide sequences containing variable region encoding sequences often comprise a plurality of primers where several primers can be degenerate primers. Amplification of families of immunoglobulin light chain variable region encoding sequences is for example performed using a primer set comprised of a plurality of primers complementary to the 5' end of the variable region of the kappa chain (mVK primer(s)) or the kappa leader sequence and/or the lambda chain or the lambda leader sequence (forward primers) together with constant region kappa (mKappa1 primer(s)) and/or lambda primers (reverse primers) or a plurality of such primers. Alternatively, light chain joining region primers may be used as reverse primers instead of the constant region primers. Alternatively, forward primers annealing in the UTR region preceding the leader sequence of the variable light chain may be used. Equally, families of immunoglobulin heavy chain variable region encoding sequences can be amplified with one primer set utilizing various primer combinations. For example, a plurality of primers complementary to the 5' end of the heavy chain variable region (mVH primer(s)) or the leader sequence of this region (forward primers) together with a plurality of heavy chain joining region primers or heavy chain constant region primer(s) (reverse primers). The mCH primer may be isotype-specific and in principle any mCH primer can be utilized, also one that would result in a full-length heavy chain. Preferably a mCH primer is used that does not amplify the full length heavy chain to enable addition of a human heavy chain constant region. Alternatively, forward primers annealing in the UTR region preceding the leader sequence of the variable heavy chain may be used.

The use of forward primers annealing in the leader sequence instead of the 5' end of the variable region is particularly useful if cross-hybridization due to high degree of sequence similarity is observed for the variable region primers. Mutations due to cross-hybridization using leader-primers will be eliminated from the final protein because leader sequences are cleaved off during protein processing within the cell.

One feature of the present invention is primers which anneal in the 3' end of the leader encoding sequence preceding a variable region encoding sequence, and their use for amplification of variable region encoding sequences.

In one embodiment of the present invention, the multiplex overlap-extension primer mix utilized for the multiplex overlap-extension PCR and possibly for the reverse transcription step as well comprises:

a) at least one mKappa1 or hmJK primer complementary to the sense strand of an immunoglobulin light chain region encoding sequence;

b) at least one mVK primer complementary to the antisense strand of an immunoglobulin light chain variable region encoding sequence or light chain variable region leader sequence, and capable of forming a primer set with the primer(s) in step a);

a) at least one mCHrev1, mHCrev1-ext, or mJH primer complementary to the sense strand of an immunoglobulin heavy chain domain encoding sequence; and b) at least one mVH primer complementary to the antisense strand of an immunoglobulin heavy chain variable region encoding sequence or heavy chain variable region leader sequence, and capable of forming a primer set with the primer(s) in step c)

In one embodiment of the present invention the light chain primer are adapted for amplifying both kappa and lambda light chain variable region encoding sequences.

In a further embodiment of the present invention, the immunoglobulin mVK primers carry linkage tails, preferably in the form of complementary overlap-extension tails. This generates variable region encoding sequences that are linked in a head-to-head fashion. For the linkage of variable region encoding sequences in a head-to-tail fashion, either the mKappa1 and mVH primers contain linkage tails or the mVK and mCHrev1 primers contain linkage tails, preferably in the form of complementary overlap-extension tails. For the linkage of variable region encoding sequences in a tail-to-tail fashion, mCH and mKappa1 primers contain linkage tails, preferably in the form of complementary overlap-extension tails.

Preferentially, the multiplex primer mixes, including multiplex overlap-extension primer mixes, of the present invention comprise two primer sets. Thus, a multiplex primer mix comprises at least four different primers. In a further aspect of the present invention a multiplex primer mix comprises more than four different primers. A multiplex primer mix of the present invention is used for the amplification of target sequences in a single vessel. For example kappa, lambda and heavy chain variable regions may be amplified in the same vessel.

The present invention also encompasses primers for an additional PCR amplification of the linked products obtained by multiplex RT-PCR followed by linkage by ligation or recombination or by multiplex overlap-extension RT-PCR. This additional PCR amplification can be performed using a primer mix adapted for amplifying the linked target sequences. Such a primer mix may comprise the outer primers of the multiplex primer mix or multiplex overlap-extension primer mix, meaning the primers that anneal to the outermost 5' end and 3' end of the sense strand of the linked nucleotide sequences, thereby selectively enabling the amplification of the entire linked product. This process generally serves to increase the amount of linked product obtained from the multiplex RT-PCR followed by linkage by ligation or recombination or from the multiplex overlap-extension RT-PCR.

Alternatively, a primer set which is nested compared to the outer primers used in the primary multiplex RT-PCR or multiplex overlap-extension RT-PCR reaction can be used for the additional amplification of the linked nucleotide sequences. In the present invention such a primer set is termed a nested primer set. The design of nested primers generally observes the same design rules as for the gene-specific primers previously described, except that they prime partly or totally 3' to the annealing position of the outer primers used in the multiplex RT-PCR or multiplex overlap-extension RT-PCR. The product resulting from a nested PCR may therefore be shorter than the linked product obtained by the multiplex RT-PCR followed by linkage by ligation or recombination or by multiplex overlap-extension RT-PCR. In addition to increasing the amount of linked product, the nested PCR further serves to increase the overall specificity, especially of the multiplex overlap-extension RT-PCR technology. However, it should be noted that not all multiplex primer mixes/multiplex overlap-extension primer mixes that have been described previously are suitable for combination with a nested primer set when performing the additional amplification. In such cases the outer primers of the multiplex primer mix/multiplex overlap-extension primer mix can be used for the additional amplification or a semi-nested PCR can be applied as described later.

In one embodiment of the present invention, a mixture of $J_L$ and $J_H$ primers is used as nested primers for the additional amplification of the linked immunoglobulin variable region encoding sequences.

Nested primer sets of the present invention can also be comprised of a reverse (or forward) outer primer(s) from the first multiplex primer mix/multiplex overlap-extension primer mix and a second nested primer that prime 3' to the annealing position of the forward (or reverse) outer primer(s) of the first multiplex primer mix/multiplex overlap-extension primer mix. The use of such a primer set for an additional PCR amplification is generally known as a semi-nested PCR. Semi-nested PCR can for example be applied if it is difficult to design a nested primer in one specific region e.g. for the variable region sequences, because such a primer would have to anneal in the complementarity determining regions (CDRs). Further, semi-nested PCR can be used when it is desirable to keep one end of the linked sequences intact e.g. for cloning purposes.

Optimization of Multiplex Overlap-Extension PCR

The parameters of the multiplex overlap-extension PCR step of both the two-step and the single-step procedure can be optimized on several parameters (see, for example, Henegariu, O. et al. 1997. BioTechniques 23, 504-511; Markoulatos, P. et a/2002. J. Clin. Lab. Anal. 16, 47-51). Generally the same optimization parameters apply for multiplex RT-PCR, although the ratio between outer and inner primers is less important for such a reaction.

a. Primer Concentration

The concentration of the primers carrying the overlap-extension tail (for example the $V_H$ and $V_L$ primers) is preferably lower than the concentration of the outer primers without overlap-extension tail (for example $J_H$ and kappa primers).

If one of the target sequences amplifies with a lower efficiency than the others, for example, as a result of a higher GC %, it may be possible to equalize the amplification efficacy. This may be done by using a higher concentration of the primer set which mediates amplification with low efficiency, or lowering the concentration of the other primers. For example, sequences encoding for heavy chain variable regions tend to have a higher GC % and hence lower amplification efficiency than light chain variable regions. This points towards using $V_L$ primers at a lower concentration than the $V_H$ primers.

Further, when using a large number of primers the total primer concentration might be an issue. The upper limit is determined experimentally by titration experiments. For the "AmpliTaq Gold" PCR system from Applied Biosystems the upper limit was found to be 1.1 µM total oligonucleotide concentration, for other systems it may however be as high as 2.4 µM. Such an upper limit of total oligonucleotide concentration influences the maximal concentration of individual primers. If the individual primer concentration is too low it is likely to cause a poor PCR sensitivity.

The quality of the oligonucleotide primers have also been found to be important for the multiplex overlap-extension PCR. HPLC-purified oligonucleotides, have produced the best results.

b. PCR Cycling Conditions:

Preferentially the cycling conditions are as follows:

| | | | |
|---|---|---|---|
| Denaturation: | 10-30 s | 94° C. | |
| Annealing: Tm | 30-60 s | 50-70° C. | Approximately 5° C. below of primers. |
| Extension: | 1 min × EPL | 65-72° C. | EPL is Expected Product Length in kb. |
| Cycle number: | 30-80 | | |
| Final extension: | 10 min | 65-72° C. | |

For the single-step multiplex overlap-extension RT-PCR the following steps were built into the cycling program prior to the amplification cycling outlined above:

| | | | |
|---|---|---|---|
| Reverse transcription: | 30 min | 42-60° C. | These conditions are also used where separate transcription is performed. |
| Polymerase activation: | 10-15 min | 95° C. | Hot-start polymerases are favorable in single-step RT-PCR. Activation according to manufacturer. |

It is possible to optimize all these parameters. Especially the annealing temperature is important. Thus, initially all the individual primer sets that are to constitute the final primer mix should be tested separately in order to identify optimal annealing temperature and time, as well as elongation and denaturing times. This will give a good idea about the window within which these parameters can be optimized for the multiplex overlap-extension primer mix.

Problems with poor PCR sensitivity, for example due to low primer concentration or template concentration can be overcome by using a high number of thermal cycles. A high number of thermal circles constitute between 35 and 80 cycles, preferably around 40 cycles.

Further, longer extension times can improve the multiplex overlap-extension PCR process. Long extension times constitute 1.5-5 min×EPL compared to the normal 1 min extension.

c. Use of Adjuvants

Multiplex PCR reactions can be significantly improved by using a PCR additive, such as DMSO, glycerol, formamide, or betaine, which relax DNA, thus making template denaturation easier.

d. dNTP and $MgCl_2$

Deoxynucleoside triphosphate (dNTP) quality and concentration is important for the multiplex overlap-extension PCR. The best dNTP concentration is between 200 and 400 µM of each dNTP (dATP, dCTP, dGTP and dTTP), above which the amplification is rapidly inhibited. Lower dNTP concentrations (100 µM of each dNTP) suffice to achieve PCR amplification. dNTP stocks are sensitive to thawing/freezing cycles. After three to five such cycles, multiplex PCR often do not work well. To avoid such problems, small aliquots of dNTP can be made and kept frozen at −20° C.

Optimization of $Mg^{2+}$ concentration is critical since most DNA polymerases are magnesium-dependent enzymes. In addition to the DNA polymerase, the template DNA primers and dNTP's bind $Mg^{2+}$. Therefore, the optimal Mg concentration will depend on the dNTP concentration, template DNA, and sample buffer composition. If primers and/or template DNA buffers contain chelators such as EDTA or EGTA, the apparent Mg2+ optimum may be altered. Excessive Mg2+ concentration stabilizes the DNA double strand and prevents complete denaturation of DNA, which reduces yield. Excessive $Mg^{2+}$ can also stabilize spurious annealing of primer to incorrect template sites, thereby decreasing specificity. On the other hand, an inadequate $Mg^{2+}$ concentration reduces the amount of product.

A good balance between dNTP and $MgCl_2$ is approximately 200 to 400 µM dNTP (of each) to 1.5 to 3 mM $MgCl_2$.

e. PCR Buffer Concentration

Generally KCl based buffers suffice for multiplex overlap-extension PCR; however, buffers based on other components such as $(NH_4)_2SO_4$, $MgSO_4$, Tris-HCl, or combinations thereof may also be optimized to function with the multiplex overlap-extension PCR. Primer pairs involved in the amplification of longer products work better at lower salt concentrations (e.g. 20 to 50 mM KCl), whereas primer pairs involved in the amplification of short products work better at higher salt concentrations (e.g. 80 to 100 mM KCl). Raising the buffer concentration to 2× instead of 1× may improve the efficiency of the multiplex reaction.

f. DNA Polymerase

The present invention is exemplified with Taq polymerase. Alternatively, other types of heat-resistant DNA polymerases including, for example, Pfu, Phusion, Pwo, Tgo, Tth, Vent, Deep-vent may be used. Polymerases without or with 3' to 5'exonuclease activity may either be used alone or in combination with each other.

Vectors and Libraries

The linkage of nucleotide sequences of interest according to the present invention produces a nucleotide segment comprising the linked nucleotide sequences coding for variable regions of immunoglobulins. Further, libraries of such linked nucleic acid sequences are produced by the methods of the present invention, in particular libraries of non-human variable region encoding sequences liked or spliced to human constant region (heavy and light chain) sequences.

One feature of the present invention is the insertion of a segment containing linked nucleotide sequences of interest or a library of linked nucleotide sequences of interest, generated by a method of the present invention, into suitable vectors. The libraries may be combinatorial libraries or more preferably libraries of cognate pairs of variable region encoding sequences. The restriction sites generated by the outer primers, nested primers or semi-nested primers are preferably designed to match appropriate restriction sites of the vector of choice. The linked nucleic acid sequences of interest can also be inserted into vectors by recombination, if one of the semi-nested, nested primers or outer primers were equipped with a suitable recombination site and the vector of choice contains one as well.

Basically there are no limitations to the vectors that can be used as carriers of the products generated by one of the multiplex RT-PCR-linkage methods of the present invention. Vectors of choice may be those suitable for amplification and expression in cells including, for example, bacteria, yeast, other fungi, insect cells, plant cells, or mammalian cells. Such vectors may be used to facilitate further cloning steps, shuttling between vector systems, display of the product inserted into the vector, expression of the inserted product and/or integrate into the genome of a host cell.

Cloning and shuttle vectors are preferably bacterial vectors. However, the other types of vectors may also be applied in cloning and shuttle procedures.

Display vectors can for example be phage vectors or phagemid vectors originating from the class of fd, M13, or f1 filamentous bacteriophages. Such vectors are capable of facilitating the display of a protein including, for example, a binding protein or a fragment thereof, on the surface of a filamentous bacteriophage. Display vectors suitable for display on ribosomes, DNA, yeast cells or mammalian cells are also known in the art. These comprise for example viral vectors or vectors encoding for chimeric proteins.

Expression vectors exist for all the mentioned species and the one to be chosen completely depend on the protein to be expressed. Some expression vectors are additionally capable of integrating into the genome of a host cell either by random integration, or by site-specific integration, utilizing appropriate recombination sites. Expression vectors may be designed to provide additional encoding sequences that, when the linked product is inserted in-frame to these sequences, enable the expression of a larger protein, e.g. a full-length monoclonal antibody, when introduced into an appropriate host cell. This in-frame insertion may also facilitate the expression of chimeric proteins that facilitate the display on the surface of a filamentous bacteriophage or cell. In a bacteriophage display system, the linked nucleotide sequences of interest may be inserted in-frame to a sequence encoding a coat protein such as pIII or pVIII (Barbas, C. F. et al. 1991. Proc. Natl. Acad. Sci. USA 88, 7978-7982; Kang, A. S. et al. 1991. Proc. Natl. Acad. Sci. USA 88, 4363-4366).

In one embodiment of the present invention, the individual segments of linked nucleotide sequences of interest is comprised of an immunoglobulin heavy chain variable region encoding sequence associated with a light chain variable region encoding sequence from one species, inserted into a vector that contains sequence(s) encoding one or more human immunoglobulin constant domains, preferably both human light and heavy chain constant regions. The insertion is engineered such that the linked heavy chain variable region and/or light chain variable region encoding sequences are inserted in-frame to the constant region encoding sequences. Such an insertion can for example generate a Fab or F(ab')$_2$ expression vector, a full-length antibody expression vector or an expression vector encoding a fragment of a full-length antibody. Preferentially such a vector is an expression vector suitable for expression (e.g. E. coli, phagemid, or mammalian vectors) and the constant region heavy chain encoding sequences are chosen from the human immunoglobulin classes IgG1, IgG2, IgG3, IgG4, IgM, IgA1, IgA2, IgD, or IgE, thereby enabling the expression of a Fab or full-length recombinant antibody. In addition to the constant heavy chain encoding sequences the vector may also contain a constant light chain encoding sequence chosen from human lambda or kappa chains. This is preferred in the generation of chimeric antibodies as the linked nucleotide sequences in these cases only encode the immunoglobulin variable region encoding sequences (Fv's) from the non-human species.

In an alternative embodiment, the human constant region(s) is/are spliced or linked to the non-human variable regions in a step of the molecular amplification procedure, by adding to the vessels a human constant region providing an overlap with the non-human sequence and appropriate primers assuring the amplification of both variable and constant region(s) in frame. In this way the human constant kappa or lampda chain may be added and/or a human constant heavy chain may be added. By using this procedure there is no need for providing a restriction site within the coding sequence, which is an advantage In another embodiment of the present invention, the individual segments of the linked nucleotide sequences is comprised of a TcR α chain variable region encoding sequence associated with a β chain variable region encoding sequence or a γ chain variable region encoding sequence associated with a δ chain variable region encoding sequence. Preferably, these linked sequences are inserted into a vector that contains sequences encoding one or more TcR constant domains. The insertion is engineered such that the inserted linked variable region encoding sequences are in-frame to the corresponding TcR constant region encoding sequences. In a further embodiment, such a vector is a chimeric expression vector comprising sequences that encode a leucine zipper in-frame to the TcR constant regions. It has been shown that such constructs increase stability of soluble TcR's (Willcox, B. E. et al. 1999. Protein Sci 8, 2418-2423).

Libraries of cognate pairs of the present invention may be introduced into vectors by two different approaches. In the first approach, the single cognate pairs are inserted individually into a suitable vector. This library of vectors may then either be kept separate or be pooled. In the second approach, all the cognate pairs are pooled prior to vector insertion, followed by in-mass insertion into suitable vectors generating a pooled library of vectors. Such a library of vectors comprises a large diversity of pairs of variable region encoding sequences.

One aspect of the present invention is a library of antibodies with cognate pairs of linked variable region encoding sequences. Preferably the individual antibodies of the library comprise an immunoglobulin light chain variable region encoding sequence associated with a heavy chain variable region encoding sequence from one species and human constant regions.

Another preferred library of cognate pairs comprise linked TcR region encoding sequences, where each individual TcR region encoding sequences comprise an alpha chain variable region encoding sequence associated with a beta chain variable region encoding sequence and/or a TcR gamma chain variable region encoding sequence associated with a delta chain variable region encoding sequence.

An embodiment of the present invention is a sub-library of cognate pairs of linked variable region encoding sequences which encode for desired binding specificities directed against a particular target. Preferably these cognate pairs comprise linked immunoglobulin light chain variable region and heavy chain variable region encoding sequences, TcR alpha chain variable region and beta chain variable region encoding sequences and/or TcR gamma chain variable region and delta chain variable region encoding sequences.

A further embodiment is a sub-library selected from a parent library of cognate pairs of variable region encoding sequences as described throughout the invention.

A preferred embodiment of the present invention is a library or sub-library encoding cognate pairs of full-length chimeric immunoglobulins selected from human immunoglobulin classes IgA1, IgA2, IgD, IgE, IgG1, IgG2, IgG3, IgG4, or IgM.

Another preferred feature of the present invention is a library or sub-library encoding for soluble and stable cognate pairs of TcR5.

A feature of the present invention is the diversity of said libraries, which are comprised of at least 5, 10, 20, 50, 100, 1000, $10^4$, $10^5$ or $10^6$ different cognate pair antibodies.

In a further embodiment of the present invention, said libraries of cognate pairs of linked variable region encoding sequences are obtainable by a method comprising the steps described herein. This library is also termed the parent library.

Screening and Selection

The parent library of pairs of linked variable region encoding sequences isolated from a donor, utilizing one of the methods of the present invention, is expected to represent a diversity of binding proteins of which some will be irrelevant, i.e. not binding to a desired target, in particular for combinatorial libraries. Therefore, the present invention encompasses enrichment and screening, for a sub-library encoding a subset of diversities of binding specificities directed against a particular target.

For libraries of cognate pairs the diversity of the library is expected to represent the diversity present in the donor material, with only a minor number of randomly linked variable regions. Thus, an enrichment step may not be necessary prior to the screening for target-specific binding affinities in a library composed of cognate pairs.

In a further embodiment of the present invention, the method of generating a library of pairs of linked variable region encoding sequences, further comprises creating a sub-library by selecting a subset of pairs of linked variable region sequences that encode binding proteins with a desired target specificity. Such a selection of linked variable region encoding sequences, is also termed a library of target-specific cognate pairs.

In a preferred embodiment of the present invention, the library of target-specific cognate pairs of variable region encoding sequences is transferred to an expression vector. The expression vector may be a mammalian expression vector, a yeast expression vector, a fungus expression vector, a plant expression vector, a bacterial expression vector depending on the type of cell used for screening. Preferably the expression vector is mammalian.

Immunological assays are generally suitable for the selection of target-specific immunoglobulin variable region encoding sequences. Such assays are well know in the art and constitute for example FMAT, FLISA, ELISPOT, ELISA, membrane assays (e.g. Western blots), arrays on filters, or FACS. The assays can either be performed in a direct manner, utilizing the polypeptides produced from the immunoglobulin variable region encoding sequences. Alternatively, the immunoassays can be performed in combination with or following enrichment methods such as phage display, ribosome display, bacterial surface display, yeast display, eukaryotic virus display, RNA display or covalent display (reviewed in FitzGerald, K., 2000. Drug Discov. Today 5, 253-258). Both cognate Fab expression libraries and cognate full-length antibody expression libraries can be subjected to screening, thereby generating a sub-library of positive clones. Such screening assays and enrichment procedures are also suitable for Fv or scFv fragments or combinatorial libraries of linked variable regions.

In addition to immunological screening, a special feature of the invention is that it enables the use of various types of functional screening to select antibody secreting clones with desired properties. Such screening assays include but are not limited to proliferation assays, virus inactivation assays, cell killing assays, etc. Preferably the functional assays can be carried out in high-throughput format using supernatants from cells transfected with expression vectors of the invention.

In a preferred embodiment of the present invention, the selection of a sub-library of target-specific cognate pairs or combinatorial pairs of variable region encoding sequences is performed by using a high-throughput screening assay. High-throughput screening assays could be, but are not restricted to, ELISA assays performed with semi-automated or fully automated equipment. It could also be a membrane assay in which bacteria are robotically picked and gridded onto an appropriate membrane on top of agar plates generating arrays of colonies expressing antigen-binding molecules. The molecules are secreted through the membrane onto a second underlying antigen-coated membrane which can be developed separately and used to identify clones that secrete antigen binding molecules towards the desired target (de Wildt, R. M., et al. 2000. Nat. Biotechnol. 18, 989-994).

When a sub-library of cognate pairs or combinatorial pairs of antigen-binding clones has been selected by an appropriate technology it is possible to perform an additional analysis by DNA sequencing of the linked immunoglobulin light chain variable region and heavy chain variable region encoding sequences. First of all such a DNA sequencing will provide information about the library diversity such as germline origin, family distribution and maturation within the CDR regions. Such an analysis will enable the selection of clones which represent a broad diversity, and leaving out repeated clones. Secondly, DNA sequencing will reveal mutations introduced during the isolation process.

When analyzing variable region encoding sequences there are three types of mutations to consider when assessing whether a mutation is acceptable: i) The most frequent type of mutations result from cross-priming, where a V gene primer due to sequence similarities primes a germline sequence to which it is not totally homologous. The changes introduced are mainly substitutions of naturally occurring codons at one particular position. Due to the high degree of sequence homology between V-gene sequences. Some of these changes may be significant, sometimes with no natural counterpart. Such changes could potentially affect the immunogenicity of the variable region by creating new epitopes. Such changes can easily be identified and subsequently repaired using standard molecular biological techniques or the clones can be excluded from the library; ii) Errors created by the Taq DNA polymerase are most easily identified in the constant region encoding sequences and can easily be eliminated. However, Taq induced mutations will of course also be present in the variable region encoding sequences where they are indistinguishable from the naturally occurring somatic mutations, which are also the result of random mutations in the variable region encoding sequences. Considering that the mutations are non-systematic and only affect particular pairs in distinct ways, it appears reasonable to disregard such changes.

In a further embodiment of the present invention, the sub-library of target-specific and possibly sequence analysed pairs of linked immunoglobulin light chain variable region and heavy chain variable region encoding sequences are transferred to a mammalian expression vector. Such a transfer can be performed into any of the vectors described in the previous section, enabling the expression of a full-length recombinant antibody. If the screening is performed with a mammalian cognate full-length antibody expression library such a transfer may not be needed.

In another embodiment of the present invention, the parent library is generated from a lymphocyte-containing cell fraction which is enriched for T lymphocytes. The pairs of linked variable region encoding sequences constituting the parent library, may be selected for encoding a subset of pairs of linked variable region sequences, composed of alpha and beta and/or gamma and delta chains that encode binding proteins with a desired target specificity, generating a sub-library of cognate pairs or combinatorial pairs. Antigen-specific T cell receptors can subsequently be identified from a pool of transfected cells using standard methodology such as staining with tetrameric MHC-peptide complexes (e.g., Callan, M. F. et al. 1998. J. Exp. Med. 187, 1395-1402; Novak, E. J. et al. 1999. J. Clin. Invest 104, R63-R67), by measuring cellular responses in the form of IL-2 release or by more sophisticated means such as yeast or retroviral display techniques.

Host Cells and Expression

The libraries of the present invention can be transferred to vectors suitable for expression and production of proteins encoded from the linked nucleic acid sequences of interest, in particular variable region containing binding proteins or fragments thereof. Such vectors are described in the Vectors and Libraries section, and provide for the expression of for example full-length antibodies, Fab fragments, Fv fragments, scFv, membrane bound or soluble TcRs or TcR fragments of a species of choice.

One feature of the present invention is the introduction into a host cell of a library or a sub-library of vectors of cognate pairs of linked variable region encoding sequences or a single clone encoding a cognate pair of linked variable region encoding sequences, for amplification and/or expression. Host cells can be chosen from bacteria, yeast, other fungi, insect cells, plant cells, or mammalian cells. For expression purposes mammalian cells, such as Chinese hamster ovary (CHO) cells, COS cells, BHK cells, myeloma cells (e.g., Sp2/0 cells, NSO), NIH 3T3, fibroblast or immortalized human cells such as HeLa cells, HEK 293 cells, or PER.C6 are preferred.

The introduction of vectors into host cells may be accomplished by a number of transformation or transfection methods known to those skilled in the art, including calcium phosphate precipitation, electroporation, microinjection, liposome fusion, RBC ghost fusion, protoplast fusion, viral infection and the like. The production of monoclonal full-length antibodies, Fab fragments, Fv fragments and scFv fragments is well known.

The production of recombinant polyclonal antibodies to be used for treatment is a quite new area. A recombinant polyclonal manufacturing technology has been described in PCT application WO 2004/061104. In brief, this technology involves the generation of a collection of cells, suitable as a manufacturing cell line. The following description of the technique is made for a library of cognate pairs, it is however just as applicable for a combinatorial library. The individual cells in the collection of cells are capable of expressing a distinct member of the recombinant polyclonal binding protein for example from a library of cognate pairs. In order to ensure that the individual cells express a single cognate pair and not several cognate pairs of the polyclonal binding protein, the nucleic acid sequences encoding the cognate pairs are introduced into a single site-specific site in the genome of each individual cell. This is an important feature of the collection of cells, since this prevent scrambling of the heavy and light chains expressed from each cell, but also because it generates cells that are virtually identical to one another, except for the small differences in the variable regions of the individual cognate pairs. This trait will enable an unbiased growth of the collection of cells over the period of time necessary for the production. To ensure single site-specific integration, a host cell line with only one integration site should be used, these are commercially available e.g. Invitrogen's CHO Flp-In cells containing a single FRT site. Appropriate vectors for this cell line contain a corresponding FRT site and are introduced into the genome using the Flp recombinase. There are several other known recombinases e.g. Cre, beta-recombinase, Gin, Pin, PinB, PinD, R/RS, lambda integrase, or phage ΦC31 integrase that can be used in combination with their corresponding recombination sites. Further, appropriate vectors contain a selection marker that enables the selection of site-specific integrants.

The generation of a polyclonal manufacturing cell line and the production of a recombinant polyclonal protein from such a cell line can be obtained by several different transfection and manufacturing strategies.

One way, is to use a library of vectors mixed together into a single composition, for the transfection of a host cell line with a single integration site per cell. This method is termed bulk transfection or transfection in bulk. Generally, the vector and host cell design previously described will ensure that a polyclonal cell line capable of unbiased growth will be obtained upon appropriate selection. A frozen stock of the polyclonal cell line will be generated before initiation of the recombinant polyclonal protein manufacturing.

Another way, is to use a library of vectors split into fractions, containing approximately 5 to 50 individual vectors of the library in a composition, for transfection. Preferably, a fraction of the library constitutes 10 to 20 individual vectors. Each composition is then transfected into an aliquot of host cells. This method is termed semi-bulk transfection. The number of aliquots transfected will depend on the size of the library and the number of individual vectors in each fraction. If the library for example constitutes 100 distinct cognate pairs, which are split into fractions containing 20 distinct members in a composition, 5 aliquots of host cells would need to be transfected with a library composition constituting a distinct fraction of the original library. The aliquots of host cells are selected for site-specific integration. Preferably, the distinct aliquots are selected separately. However, they can also be pooled before selection. The aliquots can be analyzed for their clonal diversity and only those with sufficient diversity will be used to generate a polyclonal cognate pair library stock. To obtain the desired polyclonal cell line for manufacturing, the aliquots can be mixed before generating the freezing stock, immediately after they have been retrieved from the stock or after a short proliferation and adaptation time. Optionally, the aliquots of cells are kept separate throughout production, and the polyclonal protein composition is assembled by combining the products of each aliquot rather than the aliquots of cells before production.

A third way, is a high throughput method in which host cells are transfected separately using the individual vectors constituting the library of cognate pairs. This method is termed individual transfection. The individually transfected host cells are preferably selected for site specific integration separately. The individual cell clones generated upon selection may be analyzed with respect to proliferation time and preferably, those with similar growth rates are used to generate a polyclonal cognate pair library stock. The individual cell clones can be mixed to obtain the desired polyclonal cell line before generating the stock, immediately after they have been retrieved from the stock, or after a short proliferation and adaptation time. This approach may eliminate any possible residual sequence bias during transfection, integration and selection. Alternatively the individually transfected host cells are mixed before selection is performed, this will enable control of sequence bias due to transfection.

A shared feature in the manufacturing strategies outlined in the above is that all the individual cognate pairs constituting the recombinant polyclonal protein can be produced in one, or a limited number of bioreactors. The only difference is the stage at which one chooses to generate the collection of cells that constitutes the polyclonal manufacturing cell line.

One embodiment of the present invention, is a population of host cells comprising a cognate library or sub-library of linked pairs of variable region encoding sequences.

In a further embodiment, a population of host cells comprises a library obtained from a population of isolated single cells constituting lymphocytes, utilizing the multiplex RT-PCR amplification followed by linkage by ligation or recombination or the multiplex overlap-extension RT-PCR technology of the present invention, to link the cognate pairs.

Another embodiment of the present invention, is a population of host cells comprising a combinatorial library or sub-library of linked pairs of variable region encoding sequences.

A population of host cells according to the present invention, will encompass a diverse population of cells corresponding to the diversity of the library the cells have been transformed/transfected with. Preferably, each cell of the population of cells only constitutes one cognate pair of the entire library of cognate pairs, and no individual member of the library of cognate pairs exceeds more than 50%, more preferred 25%, or most preferred 10%, of the total number of individual members expressed from the population of host cells.

In a preferred embodiment of the present invention, the population of host cells is mammalian cells.

A population of host cells as described in the above can be utilized for the expression of a recombinant polyclonal binding protein, since individual cells of the population constitute variable region encoding sequences of different diversity.

One embodiment of the present invention, is a recombinant polyclonal protein expressed from a population of host cells comprising a library of vectors encoding diverse cognate pairs of linked variable region encoding sequences, where such a library is obtainable by the method of the present invention. Typically, a recombinant polyclonal protein of the present invention is comprised of at least 2, 5, 10, 20, 50, 100, 1000, $10^4$, $10^5$ or $10^6$ proteins composed of different cognate pairs.

A preferred embodiment of the present invention, is a recombinant polyclonal immunoglobulin expressed from a population of host cells comprising a library of vectors encoding diverse cognate pairs of heavy chain variable region and light chain variable region encoding sequences.

Another preferred embodiment of the present invention, is a recombinant polyclonal TcR expressed from a population of host cells comprising a library of vectors encoding diverse cognate pairs of TcR alpha chain variable region linked with beta chain variable region encoding sequences and/or TcR gamma chain variable region linked with delta chain variable region encoding sequences.

Another embodiment of the present invention is a host cell suitable for production of a monoclonal protein. In particular a monoclonal antibody comprised of a cognate pair of a light chain variable region with a heavy chain variable region or a monoclonal TcR comprised of a cognate pair of an alpha variable region with a beta variable region or a delta variable region with a gamma variable region. Preferably such a monoclonal production cell line is not a hybridoma cell line.

Such a monoclonal antibody or TcR can be generated by adding the following steps to the method of linking a plurality of non-contiguous nucleotide sequences of interest a) inserting said linked nucleic acid sequences into a vector; b) introducing said vector into a host cell; c) cultivating said host cells under conditions suitable for expression; and d) obtaining the protein product expressed from the vector inserted into said host cell. Preferably, the vector introduced into the host cell encodes an individual cognate pair of variable region encoding sequences.

Applications of the Invention

One of the major applications of the present invention is the linkage of cognate pairs of variable region encoding sequences, especially immunoglobulin heavy and light chain variable region encoding sequences or TcR alpha and beta chain or gamma and delta chain variable region encoding sequences, by a high-throughput method for the generation of libraries of cognate pairs. In addition to the generation of cognate pair libraries, the multiplex RT-PCR followed by linkage by ligation or recombination or the multiplex overlap-extension RT-PCR techniques of the present invention may be utilized in the generation of combinatorial libraries of chimeric human/non-human antibodies by performing the technique on a population of genetically diverse cells, cell lysates from such a population of cells, or on RNA purified from such a population of cells. The libraries, sub-libraries, or single clones from one of these libraries facilitate the expression of polyclonal or monoclonal proteins. Especially monoclonal or polyclonal antibodies may be obtained from the libraries of the present invention.

The use of recombinant monoclonal antibodies in diagnostics, treatment, and prophylaxis is well known. Recombinant monoclonal and polyclonal antibodies generated by the present invention will have the same applications as antibody products generated by existing technologies. In particular, a pharmaceutical composition comprising a polyclonal recombinant immunoglobulin as active ingredient, combined with at least one pharmaceutically acceptable excipient, can be produced by means of the present invention. More preferred are pharmaceutical compositions where the polyclonal recombinant immunoglobulin is comprised of cognate pairs of variable region encoding sequences. Such pharmaceutical compositions of polyclonal recombinant immunoglobulins can be used as medicaments. The polyclonal recombinant immunoglobulin of the composition can be specific for or reactive against a predetermined disease target, and the composition can thus be used for the treatment, amelioration or prevention of diseases such as cancer, infections, inflammatory diseases, allergy, asthma and other respiratory diseases, autoimmune diseases, immunological malfunctions, cardiovascular diseases, diseases in the central nervous system, metabolic and endocrine diseases, transplant rejection, or undesired pregnancy, in a mammal such as a human, a domestic animal, or a pet.

EXAMPLES

Example 1

Balb/c mice were immunised subcutaneously with 50 µg Tetanus toxoid (TT) in complete Freund's adjuvant. Mice were boosted on day 14 with 50 µg TT in Freund's incomplete adjuvant. After additional 30 days, the mice were boosted with 50 µg TT in Freund's incomplete adjuvant. Three days after the last boost, the mice were sacrificed and the spleen taken out and transferred to a tube containing 30 ml of RPMI 1640 w/10% FCS at 4° C. The tissue was transferred to a 74 µm cell strainer (Corning, 136350-3479) in a 10 cm dish. With the back of a syringe plunger, the spleens were macerated through the filter. The filter was rinsed 10 ml RPMI 1640, 10% FCS solution. The filter was removed and the dish filled with 20 ml cold RPMI 1640, 10% FCS. Cells were transferred to 50 ml tube and centrifuge at 300×g at 2-8° C. for 5 minutes. Cells were re-suspended in 5-10 ml 4° C. RPMI 1640 w/1% FCS and filtered through a 50 µm syringe filter (Becton Dickinson, 340603). Cells were pelleted and re-suspended in FCS; 10% DMSO to obtain a cell density at $2 \times 10^7$ cells/ampoule and frozen.

Frozen vial with splenocytes in single cell suspension from Balb/c mice immunized with Tetanus toxoid, were thawed at 37° C. and transferred to 15 ml tube with ice still present. 10 ml ice-cold RPMI, 10% FCS was drop-wise added to the tube while swirling. After one wash in 10 ml FACS PBS, 5 ml PBS, 2% FCS was added before filtering the cells through 50 µm Filcon (Becton Dickinson cat no 340603). Cells were pelleted and resuspended in 1 ml PBS, 2% FCS (final volume) and subsequently stained with either anti CD43 FITC diluted 1:100 (BD cat no 553270) and anti CD138 PE diluted 1:40 (BD cat no 553714) in 1 ml PBS, 2% FCS or with anti B220 APC (BD cat no 553092) diluted 1:40 and anti MHCII FITC (BD cat no 553547) diluted 1:200. Cells were incubated at 4° C. for 20 min in the dark. Finally, cells were washed 2 times with 2 ml PBS, 2% FCS and added up to 15 ml PBS, 2% FCS (foetal calf serum). Just before sorting, PI was added at 1:100, and cells were sorted in an event count of app. 1000-2000 cells/sec. Gatings for both stainings are depicted in FIG. 3.

FIG. 3A: PI positive (dead) cells were excluded in the bottom left panel (P1). Then plasma cells were gated as CD43 high, CD138 high in bottom right panel (P2). Finally, doublets were excluded in the SSC-H, SSC-W plot top right panel (P3). Cells positive for all three gates were sorted into ELISPOT plates according to table 1.
ELISPOT:

Nitrocellulose-bottomed 96 well plates (HA plates, Millipore, Bedford, Mass.) were pre-wet with PBS (also the blocking wells) before being coated with 100 µl 25 µg/ml tetanus toxoid (TT) or sheep anti-murine IgG (Jackson Immuno Research, cat no 515-005-062) in PBS. The same volume of PBS was present in the control wells. The plate was left at 4° C. The day after, wells were washed three times in PBS before being blocked with 200 µl RPMI+2% skim milk powder and left at 4° C. The plate was moved to the incubator (37° C., 5% $CO_2$, 100% humidity) 1 h before addition of cells. 100 µl cells in complete RPMI were added to TT-, anti-IgG coated wells and blocked-only-wells. Medium without cells was included as control. The plate was moved to an incubator (37° C., 5% $CO_2$, 100% humidity). The day after, the plate was washed six times to remove the cells, 3× in buffer: PBS+0.01% Tween20 and 3× in PBS. Subsequently, the wells were added HRP-conjugated goat anti-mouse IgG (Caltag M30007) diluted 1:3000 in RPMI+2% Skim milk powder (100 µl/well). After 2 hrs incubation 37° C., wells were washed three times in PBS+0.01% tween 20 followed by three times with only PBS. Spots were then developed with 100 µl chromogenic substrate consisting of 0.015% $H_2O_2$ and 0.3 mg/ml of 3-amino-9-ethylcarbazole in 0.1M sodium acetate, pH 5.1. The color development was stopped by washing with tap water after 5 nm.

Judging the results in table 1, Plasma cells (PC; CD43 high, CD138 high, Gate P3 in FIG. 3A) specific for TT are present at approximately 2%, whereas TT specific plasma blasts (PB; B220 and MHCII positive, Gate P4 in FIG. 3B) are present at approximately 4‰. This illustrates the superiority of the PC to PB in production of specific antibodies after TT immunization.

TABLE 1

|  |  | Number of spots (number of sorted cells) | | |
| --- | --- | --- | --- | --- |
| Coat: PBS | PC | 0 (1,001) | ND | ND |
|  | PB | 0 (13,976) | 0 (1500) | 0 (150) |
| Coat: TT | PC | 22 (1,002) | 2 (250) | 0 (50) |
|  | PB | 54 (13,257) | 0 (1500) | 0 (150) |
| Coat: α-IgG | PC | 55 (1,000) | 6 (250) | 1 (50) |
|  | PB | 48 (5000) | 8 (1500) | 0 (150) |

Example 2

A Frozen Vial of Splenocytes was Stained as Described in Example 1

Four different phenotypes were four-way sorted. The sorting gates are depicted in FIG. 4. Firstly, PI positive or dead cells were excluded in the bottom left panel (P1). P2 is CD138 intermediate, CD43 high. P3 is CD138 high, CD43 high. P4 is CD138 high, Cd43 neg. P5 is CD138 intermediate, CD43 low. 10,000 cells positive for P1 and each of the four gates were sorted into test tubes and frozen for evaluation by mouse Symplex.

Fractions P2, P3, P4 and P5 were bulk sorted into tubes each containing 10,000 cells. The tubes were centrifuged and resuspended in Dulbecco's modified Eagle's medium containing 2 U/µl RNase inhibitor (RNasin, Promoga cat. no. N2511) to a concentration of 250 cells/µl, 10 µl per tube and frozen at −80° C.

A mouse Symplex amplification was performed on a dilution series of each of the 4 sets of sorted lymfocytes to compare the content of IgG-kappa antibody mRNA. The basic principles of the reactions are:
- First is performed an RT reaction where heavy and light chain are primed by specific constant region primers
- Secondly is performed a multiplex reaction using VH and VK 5' region primers covering all variable regions and equipped with complementary overhangs facilitating the formation of overlap bands. 3' primers are located in the constant region of heavy and light chain
- Last is performed a nested reaction amplifying only conjugated VH and VK using JH and JK primers
- The final reaction product consists of VH and VK conjugated 5' end to 5' end and connected with a linker. The size should be approximately 700 bp For the combined multiplex RT-PCR reaction was used the set of primers shown in table 2 and employing the Qiagen OneStep RT-PCR kit essentially according to the manufacturers instructions. Frozen cells were thawed on ice, resuspended and centrifuged. In each dilution series was used cell lysate corresponding to 100, 32, 10, 3.2, 1, 0.32, 0.1 and 0 cells. Total reaction volumes were 20 μl. Cycling conditions were:

55° C., 30 min.
95° C., 15 min.

94° C., 30 sec.  } 35 cycles
60° C., 30 sec.

72° C., 5 min.
72° C., 10 min.

The nested reaction was performed with the set of primers shown in table 3 using FastStart polymerase (Roche) and supplied reagents essentially according to the manufacturers instructions. 1 μl of the RT-PCR reaction product was used per nested reaction in a total volume of 20 μl. Reaction conditions were:

95° C., 30 sec.  } 35 cycles
60° C., 30 sec.

72° C., 90 sec.
72° C., 10 min.

μl of each final reaction product was finally analyzed on a 1% agarose gel.

From the result of the Symplex on the titrated cell lysates (FIG. 5), it is clear that we can link heavy and light chain variable regions with cells from P3 down to approximately 0.1 cell, and from P2 from app 3.2 cells. The other gates were less efficient with linkage only being possible from approximately 32 cells and more. In conclusion the CD43 high CD138 high (P3) is most useful for Symplex™ at single cell level, while the CD43high CD138 intermediate could be used but is less efficient.

TABLE 2

Mouse Symplex primer set used for the combined RT and multiplex reaction.

| Primer | Conc (nM) | Sequence | Seq. no. |
| --- | --- | --- | --- |
| mHCrev1 | 0.2 | GACSGATGGGCCCTTGGTGG | 1 |
| mKappa1 | 0.2 | GCTGTAGGTGCTGTCTTTGC | 2 |
| mVH set | | | |
| mVH A | 0.04 | TATTCCCATGGCGCGCCSAGGTCCARCTGCARCAGYCTG | 3 |
| mVH B | 0.04 | TATTCCCATGGCGCGCCGARGTGMAGCTKGTKGAGTC | 4 |
| mVH C | 0.04 | TATTCCCATGGCGCGCCSAGGTGCAGCTKMAGGAGTC | 5 |
| mVH 8 | 0.04 | TATTCCCATGGCGCGCCCAGGTTACTCTGAAAGAGTC | 6 |
| mVH 9 | 0.04 | TATTCCCATGGCGCGCCCAGATCCAGTTGGTGCAGTCTG | 7 |
| mVK set | | | |
| mVK D | 0.04 | GGCGCGCCATGGGAATAGCTAGCCGAYATCCAGATGACHCARW | 8 |
| mVK E | 0.04 | GGCGCGCCATGGGAATAGCTAGCCRACATTGTGMTGACHCAGT | 9 |
| mVK F | 0.04 | GGCGCGCCATGGGAATAGCTAGCCSAMATTGTKCTSACCCARTC | 10 |
| mVK 1-2 | 0.04 | GGCGCGCCATGGGAATAGCTAGCCGATRTTGTGATGACBCARR | 11 |

W = A/T, R = A/G, S = G/C, Y = C/T, K = G/T, M = A/C, H = ACT, B = GCT; Conc. - final concentration.

TABLE 3

Primers for mouse Symplex nested PCR

| Primer | Conc. nM | Sequence | Seq. no |
| --- | --- | --- | --- |
| mJH set | | | |
| mJH1 | 200 | GGAGGCGCTCGAGACGGTGACCGTGGTCCC | 12 |
| mJH2 | 200 | GGAGGCGCTCGAGACTGTGAGAGTGGTGCC | 13 |
| mJH3 | 200 | GGAGGCGCTCGAGACAGTGACCAGAGTCCC | 14 |
| mJH4 | 200 | GGAGGCGCTCGAGACGGTGACTGAGGTTCC | 15 |
| mJK set | | | |
| mJK1 | 200 | GATGGTGCAGCCACAGTTCGTTTGATTTCCAGCTTGGTG | 16 |
| mJK2 | 200 | GATGGTGCAGCCACAGTTCGTTTTATTTCCAGCTTGGTC | 30 |
| mJK4 | 200 | GATGGTGCAGCCACAGTTCGTTTTATTTCCAACTTTGTC | 31 |
| mJK5 | 200 | GATGGTGCAGCCACAGTTCGTTTCAGCTCCAGCTTGGTC | 17 |

Example 3

Cloning of Anti-EGFR Antibodies

Immunizations

Female BALB/c, strain A, or C57B16 mice (8-10 weeks old) were used for immunizations by injections with different purified proteins in addition to EGFR overexpressing cells.

Commercially available EGFR proteins (R&D systems cat#1095-ER or Sigma # E3641) were used for some of the immunizations. For other of the immunizations recombinant human EGFR and EGFRvIII produced as fusion proteins were used consisting of the ECD of EGFR or EGFRvIII and human growth hormone (hGH), also including a Tobacco Etch Virus (TEV)-cleavage site in addition to a His-tag. In some cases the ECD of EGFR was isolated by TEV-protease cleavage and subsequent purification on a Nickel column.

The human head-and-neck cancer cell line, HN5 (Easty D M, Easty G C, Carter R L, Monaghan P, Butler L J. Br J. Cancer. 1981 June; 43(6):772-85. Ten human carcinoma cell lines derived from squamous carcinomas of the head and neck.) expressing approximately $10^7$ receptors/cell were used for cell based immunizations. Cells were cultured in DMEM medium supplemented with 10% FBS (Fetal Bovine Serum), 3 mM Glycerol, 5 mM Sodium Pyruvate and 1% Penicillin Streptomycin. Before each immunization the cells were washed in PBS, trypsinized with TrypLE and resuspended in growth medium. Subsequently the cell suspensions was washed twice in PBS by centrifugation at 250×g for 5 min, dislodging and resuspension in 15 ml sterile PBS.

Cells or antigen were diluted in PBS and then mixed 1:1 with Freund's Adjuvant. Adjuvant is used to enhance and modulate the immune response. For the first immunizations Complete Freund's Adjuvant (CFA) was used whereas Incomplete Freund's Adjuvant (IFA) was used for the subsequent immunizations. IFA is an oil-in-water emulsion composed of mineral oils and CFA is IFA to which heat-killed, dried *Mycobacterium* species are added. Both adjuvants have a depot effect. CFA gives rise to long-term persistence of the immune response and is used for the first immunizations to boost the immune response and IFA is used for subsequent immunizations. The emulsions were tested by adding a drop on the surface of a glass with water. If the drop remains as one drop, the emulsion is stable and the injections can be performed. Only stable emulsions were administered to mice.

Depending on the schedule (see Table 4), 25-100 μg antigen or $10^7$ cells were used for each injection. In total, mice received 4 injections. All mice were injected with either 300 μl or 200 μl emulsion. Depending on the schedule, injections were performed subcutaneously (s.c.), intraperitoneally (i.p.) or intravenous (i.v.).

At termination, the mice were sacrificed by cervical dislocation, and the spleens were removed and transferred to a 74 μm cell strainer (Corning #136350-3479). The cells were macerated through the filter, resuspended in cold RPMI 1640 with 10% FBS and centrifuged at 300×g for 5 minutes. The cell pellet was resuspended in RPMI 1640 with 1% FBS, filtered through a 50 μm syringe filter (BD #340603) and collected by centrifugation. The cell pellet was cryopreserved after resuspension in FCS with 10% DMSO and frozen cells stored at −80° C. until FACS sorting.

FACS Sorting of Murine Plasma Cells

Vials with frozen splenocytes were thawed at 37° C. and transferred to 15 ml tube with ice still present. 10 ml Ice-cold RPMI, 10% FBS (foetal bovine serum) was dropwise added to the tube while swirling. After one wash in 10 ml FACS PBS, 5 ml FCS PBS is added before filtering the cells through 50 μm Filcon. Cells were then pelleted and resuspended in 1 ml PBS with 2% FBS (final volume) and stained with anti-CD43-FITC and anti-CD138-PE according to the specific dilution to a final concentration of app. 5 μg/ml. Cells were incubated at 4° C. for 20 min in the dark. Subsequently, cells were washed 2 times with 2 ml FACS buffer. Up to 15 ml FACS PBS were added. Propidium Iodide (PI) was added at 1:100, and cells were subsequently sorted into 96 well PCR-plates, containing PCR reaction buffer (see below), and spun down for 2 min 400×g before the plates were frozen at −80° C. Plasma cells were gated as CD43-positive/CD-138 positive.

Linkage of Cognate $V_H$ and $V_L$ Pairs

The linkage of $V_H$ and $V_L$ coding sequences was performed on the single cells gated as plasma cells, facilitating cognate pairing of the $V_H$ and $V_L$ coding sequences. The procedure utilized a two step PCR procedure based on a one-step multiplex overlap-extension RT-PCR followed by a nested PCR. The primer mixes used in the present example only amplify Kappa light chains. Primers capable of amplifying Lambda light chains could, however, be added to the multiplex primer mix and nested PCR primer mix if desired. If Lambda primers are added, the sorting procedure should be adapted such that Lambda positive cells are not excluded. The principle for linkage of cognate $V_H$ and $V_L$ sequences is illustrated in FIG. 1.

The 96-well PCR plates produced were thawed and the sorted cells served as template for the multiplex overlap-extension RT-PCR. The sorting buffer added to each well before the single-cell sorting contained reaction buffer (OneStep RT-PCR Buffer; Qiagen), primers for RT-PCR (see Table 2 above) and RNase inhibitor (RNasin, Promega). This was supplemented with OneStep RT-PCR Enzyme Mix (25× dilution; Qiagen) and dNTP mix (200 μM each) to obtain the given final concentration in a 20-μl reaction volume. The plates were incubated for 30 min at 55° C. to allow for reverse transcription of the RNA from each cell. Following the RT, the plates were subjected to the following PCR cycle: 10 min at 94° C., 35×(40 sec at 94° C., 40 sec at 60° C., 5 min at 72° C.), 10 min at 72° C.

The PCR reactions were performed in $H_{20}$BIT Thermal cycler with a Peel Seal Basket for 24 96-well plates (ABgene) to facilitate a high-throughput. The PCR plates were stored at −20° C. after cycling.

For the nested PCR step, 96-well PCR plates were prepared with the following mixture in each well (20-μl reactions) to obtain the given final concentration: 1× FastStart buffer (Roche), dNTP mix (200 μM each), nested primer mix (see Table 5), Phusion DNA Polymerase (0.08 U; Finnzymes) and FastStart High Fidelity Enzyme Blend (0.8 U; Roche). As template for the nested PCR, 1111 was transferred from the multiplex overlap-extension PCR reactions. The nested PCR plates were subjected to the following thermocyling: 35×(30 sec at 95° C., 30 sec at 60° C., 90 sec at 72° C.), 10 min at 72° C.

Randomly selected reactions were analyzed on a 1% agarose gel to verify the presence of an overlap-extension fragment of approximately 890 basepairs (bp).

The plates were stored at −20° C. until further processing of the PCR fragments.

The repertoires of linked $V_H$ and $V_L$ coding pairs from the nested PCR were pooled, without mixing pairs from different donors, and were purified by preparative 1% agarose gel electrophoresis. The human kappa constant light chain encoding sequence was spliced by overlap extension to the $V_L$ coding region of the pooled PCR products of linked $V_H$ and $V_L$ coding pairs (FIG. 2). The human kappa constant light chain encoding sequence was amplified from a plasmid containing the coding sequence of a human antibody with a kappa light chain in a reaction containing: Phusion Enzyme (2 U; Finnzymes), 1× Phusion buffer, dNTP mix (200 μM each), hKCforw-v2 primer and Kappa3' primer (Table 6), and plasmid template pLL138 (10 ng/l) in a total volume of 50 μl. The reaction was subjected to the following thermocycling: 25× (30 sec at 95° C., 30 sec at 55° C., 45 sec at 72° C.), 10 min at 72° C. The resulting PCR fragment was purified by preparative 1% agarose gel electrophoresis.

The purified pooled PCR fragments of each repertoire was spliced to the amplified and purified PCR fragment of the human kappa constant encoding region (Appendix 1) by the following splicing by overlap extension PCR (50 μl total volume) containing: human kappa constant encoding region fragment (1.4 ng/μl), purified pooled PCR fragment (1.4 ng/μl), Phusion DNA Polymerase (0.5 U; Finnzymes) and FastStart High Fidelity Enzyme Blend (0.2 U; Roche), 1× FastStart buffer (Roche), dNTP mix (200 μM each), mhKCrev primer and mJH set primers (see Table 6). The reaction was subjected to the following thermocycling: 2 min at 95° C., 25×(30 sec at 95° C., 30 sec at 55° C., 1 min at 72° C.), 10 min at 72° C. The resulting PCR fragment (approx. 1070 bp) was purified by preparative 1% agarose gel electrophoresis.

Insertion of Cognate $V_H$ and $V_L$ Coding Pairs into a Screening Vector

In order to identify antibodies with binding specificity to EGFR, the $V_H$ and $V_L$ coding sequences obtained were expressed as full-length antibodies. This involved insertion of the repertoire of $V_H$ and $V_L$ coding pairs into an expression vector and transfection into a host cell.

A two-step cloning procedure was employed for generation of a repertoire of expression vectors containing the linked $V_H$ and $V_L$ coding pairs. Statistically, if the repertoire of expression vectors contains ten times as many recombinant plasmids as the number of cognate paired $V_H$ and $V_L$ PCR products used for generation of the screening repertoire, there is 99% likelihood that all unique gene pairs are represented. Thus, if 400 overlap-extension V-gene fragments were obtained, a repertoire of at least 4000 clones was generated for screening.

Briefly, the purified PCR product of the repertoires of linked $V_H$ and $V_L$ coding pairs, spliced to the human kappa constant coding region, were cleaved with XhoI and NotI DNA endonucleases at the recognition sites introduced into the termini of PCR products. The cleaved and purified fragments were ligated into an XhoI/NotI digested mammalian IgG expression vector, OO-VP-002 (FIG. 6) by standard ligation procedures. The ligation mix was electroporated into E. coli and added to 2×YT plates containing the appropriate antibiotic and incubated at 37° C. over night. The amplified repertoire of vectors was purified from cells recovered from the plates using standard DNA purification methods (Qiagen). The plasmids were prepared for insertion of promoter-leader fragments by cleavage using AscI and NheI endonucleases. The restriction sites for these enzymes were located between the $V_H$ and $V_L$ coding gene pairs. Following purification of the vector, an AscI-NheI digested bi-directional mammalian promoter-leader fragment was inserted into the AscI and NheI restriction sites by standard ligation procedures. The ligated vector was amplified in E. coli and the plasmid was purified using standard methods. The generated repertoire of screening vectors was transformed into E. coli by conventional procedures. Colonies obtained were consolidated into 384-well master plates and stored. The number of arrayed colonies exceeded the number of input PCR products by at least 3-fold, thus giving 95% percent likelihood for presence of all unique V-gene pairs obtained.

DNA plasmid was prepared from selected clones above and FreeStyle CHO-S cells (Invitrogen) were transfected in 2-ml scale for expression of antibodies (according to the manufacturer's instructions). The supernatants were harvested 96 hours after transfection.

Screening for Binding to EGFR Extracellular Domain

In general, the screening was made as a two step procedure. The antibody-libraries were screened for reactivity to recombinant EGFR protein in ELISA after which FMAT (FLISA) was used as a cell based approach, with the NR6wtEGFR cell line (Batra et al, 1995, Cell Growth Differ, 6(10):1251-9), for detection of EGFR-antibodies binding to cell-surface expressed EGFR. For the 101 and 108/109 libraries (Table 4) the ELISA was performed with recombinant EGFR representing the extracellular domain of the EGFR.

Briefly for the ELISA, Nunc maxisorb plates (cat no 464718) were coated with 1 μg/ml protein (in house produced), diluted in PBS at 4° C. over night. Prior to blocking in 50 ul 2%-Milk-PBS-T the plates were washed once with PBS+0.05% tween 20 (PBS-T). The plates were washed once with PBS-T, 20 μl of 2%-milk-PBS-T and 5 μl supernatants from the FreeStyle CHO-S transfectants (see above) were added and incubated for 1½ hour R.T after which the plates were washed once with PBS-T 20 μl per well. Secondary antibody (HRP-Goat-anti-human IgG, Jackson, cat no 109-035-097) diluted 1:10000 in 2% milk-PBS-T was added to detect the antibodies bound to the wells and incubated for 1 hour at Room Temperature. The plates were washed once in PBS-T before addition of 25 μl substrate (Kem-en-tec Diagnostics, cat no 4390) that was incubated for 5 min. 25 μl 1M sulfuric acid was added after the incubation to stop the reaction. Specific signal was detected on an ELISA reader at 450 nm.

For the cell based FMAT detection of anti-EGFR antibodies, SKBR-3 (ATCC #HTB-30) or NR6wtEGFR cells were kept in growth medium. The cells were counted and diluted to 125,000 cells/ml with the Alexa-647 conjugated goat-anti-human IgG (H-L) antibody (Molecular probes No. A21445, lot no. 34686A) diluted 1:40,000. A total of 20 μl of this suspension was transferred to 384 well clear bottom Nunc plates. Subsequently 10 μl transfection supernatant was added to the cells. The FMAT signal from the reaction was measured after 6-10 hour of incubation.

The data from the screening indicates that 221 (4.8%) of the total clones were positive in the ELISA. 93 (2.0%) of those clones were also positive in FMAT. In total 220 (4.8%) of the clones were positive in the FMAT and among those 127 (220-93) uniquely positive for the cell surface antigen. The 111 library was screened in a similar fashion, but since the immunization procedure was made to generate antibodies specific for the deletion mutant EGFR receptor EGFRvIII, the ELISA screenings included assays to detect both wild-type EGFR and EGFRvIII. Seven clones were identified to be specific for the EGFRvIII in the ELISA and interestingly those clones were negative for staining of wtEGFR expressing cells in the FMAT. 13 clones were identified to be positive for the wtEGFR in FMAT and ELISA but not for the EGFRvIII, which were unique for this library compared to the 101 and 108/109 libraries. All the ELISA positive clones were selected for further analysis.

Sequence Analysis and Clone Selection

The clones identified as EGFR-specific in ELISA were retrieved from the original master plates (384-well format) and consolidated into new plates. DNA was isolated from the clones and submitted for DNA sequencing of the V-genes.

The sequences were aligned and all the unique clones were selected. Multiple alignments of obtained sequences revealed the uniqueness of each particular clone and allowed for identification of unique antibodies. Following sequence analysis of 220 clones, 70 genetically distinct antibody sequence clusters were identified. Each cluster of related sequences have probably been derived through somatic hypermutations of a common precursor clone. Overall, one to two clones from each cluster was chosen for validation of sequence and specificity.

Sequence and Specificity Validation

In order to validate the antibody encoding clones, DNA plasmid was prepared and transfection of FreeStyle CHO-S cells (Invitrogen) in 2-ml scale was performed for expression. The supernatant were harvested 96 hours after transfection. Expression levels were estimated with standard anti-IgG ELISA, and the specificity was determined by EGFR- and EGFRvIII-specific ELISA. 85% of the clones were shown to have the correct specificity and sequence.

Screening for Anti-Proliferative Effects

Cellular damage will inevitably result in loss of the ability of the cell to maintain and provide energy for metabolic cell function and growth. Metabolic activity assays are based on this premise. Usually they measure mitochondrial activity. The Cell Proliferation Reagent WST-1 (Roche Cat. No. 11 644 807 001) is a ready-to-use substrate which measures the metabolic activity of viable cells. It is then assumed that the metabolic activity correlates with the number of viable cells. In this example the WST-1 assay was used to measure the number of metabolically active cells after treatment with cell culture supernatants containing different anti-EGFR antibodies.

Prior to performing the WST-1 assay different volumes of 2-ml supernatants (0, 10, 25, 50 and 150 µl) were transferred to appropriate wells in a 96 well plate.

HN5 cells were then washed with 1×PBS and detached by trypsination with 3 ml trypsin solution. 17 ml of complete media were then added and the cells spun down at 300×g (1200 rcf) for 5 min. The supernatant was removed and cells re-suspended in DMEM+0.5% FBS. Cells were counted and their concentration adjusted and 1500 cells were added to the wells with supernatants so that each well contained 200 µl media in total. The plates were incubated for 4 days in a humidified incubator at 37° C. Then 20 µl WST-1 reagent was added pr. well and the plates incubated for one hour at 37° C. Plates were then transferred to a orbital plate shaker and left another hour. The absorbance was measured at 450 and 620 nm (reference wavelength) on an ELISA reader. The difference in the levels of metabolically active cells (MAC) was calculated as percent of the control supernatants as follows:

$$\% \ MAC = \left(1 - \frac{(OD\ exp. - OD media)}{(OD untreat. - OD media)}\right) \times 100$$

These values were then used as the basis for a supervised hierarchical cluster analysis (clustered based on reactivity in ELISA) performed using the free software Cluster and TreeView.

It is preferable to be able to screen for functional antibodies at an early stage in the antibody selection process. The culture supernatants from 83 2-ml transfections were used to screen for growth inhibitory functions in a proliferation assay performed using HN5 cells in 0.5% FBS. Results were visualized by simple hierarchical cluster analysis. As can be seen in the cluster analysis (FIG. 7) a number of supernatants were found to decrease the number of metabolically active HN5 cells (dark grey) in a concentration dependent manner (Cluster 2). Similarly, some supernatants increased the number of metabolically active HN5 cells (light grey) in a concentration dependent manner (Clusters 1, 3 and 4). An interesting observation was that supernatants, which decreased the number of metabolically active HN5 cells, had reactivity 2 (black arrows) whereas supernatants which increased the number of metabolically active HN5 cells had reactivity 1 (grey arrows). Supernatants with reactivity 2 were positive in both wtEGFR and EGFRvIII ELISAs, while supernatants with reactivity 1 only had reactivity towards wtEGFR. Thus, such analyses may provide relationships between antibody reactivity in ELISA and functionality in cellular assays.

Clone Repair

When using a multiplex PCR approach, a certain degree of intra- and inter-V-gene family cross-priming is expected due to primer degeneracy and the high degree of homology. The cross-priming introduces amino acids that are not naturally occurring in the immunoglobulin framework with several potential consequences, e.g. structural changes and increased immunogenicity, all resulting in a decreased therapeutic activity.

In order to eliminate these drawbacks and to ensure that selected clones mirror the natural humoral immune response, such cross-priming mutations were corrected in a process called clone repair.

In the first step of the clone repair procedure, the $V_H$ sequence was PCR amplified with a primer set containing the sequence corresponding to the $V_H$-gene the clone of interest originated from, thereby correcting any mutations introduced by cross-priming. The PCR fragment was digested with XhoI and AscI and ligated back into the XhoI/AscI digested mammalian expression vector (FIG. 6) using conventional ligation procedures. The ligated vector was amplified in E. coli and the plasmid was purified by standard methods. The $V_H$ sequence was sequenced to verify the correction and the vector was digested with NheI/NotI to prepare it for insertion of the light chain.

In the second step the complete light chain was PCR amplified with a primer set containing the sequence corresponding to the $V_L$-gene the clone of interest originated from, thereby correcting any mutations introduced by cross-priming. The PCR fragment was digested with NheI/NotI and ligated into the $V_H$ containing vector prepared above. The ligation product was amplified in E. coli and the plasmid was purified by standard methods. Subsequently, the light chain was sequenced to verify the correction.

In the case where the Kappa constant region of a selected clone contains mutations, introduced during the amplification of the genes, it is replaced by an unmutated constant region. This is done in an overlap PCR where the repaired $V_L$-gene (amplified without the constant region) was fused to a constant region with correct sequence (obtained in a separate PCR). The whole sequence is amplified and cloned into the $V_H$ containing vector as described above and the repaired light chain is sequenced to verify the correction.

TABLE 4

Immunization schedules used to generate starting material for anti-EGFR cloning.

| Mouse group | Strain | Injection 1 | Injection 2 | Injection 3 | Injection 4 | Termination |
|---|---|---|---|---|---|---|
| 101 | Balb/c | Day 1 25 μg rhEGFR (R&D systems 1095-ER) CFA s.c. | Day 35 25 μg rhGH-EGFR (Symphogen) IFA s.c | Day 56 25 μg rhEGFR* (Symphogen) IFA s.c | Day 70 25 μg rhEGFR* (Symphogen) IFA s.c | Day 73 |
| 108 | Balb/c | Day 1 1 × 10$^7$ HN5 cells CFA i.p. | Day 28 25 μg rhEGFR* (Symphogen) IFA s.c. | Day 42 1 × 10$^7$ HN5 cells IFA i.p. | Day 56 25 μg rhEGFR*, (Symphogen) IFA s.c. | Day 59 |
| 109 | Balb/c | Day 1 1 × 10$^7$ HN5 cells CFA i.p. | Day 28 25 μg rhEGFR* (Symphogen) IFA s.c. | Day 42 1 × 10$^7$ HN5 cells IFA i.p. | Day 56 25 μg rhEGFR* (Symphogen) PBS i.v. | Day 59 |
| 111 | Balb/c | Day 1 25 μg rhEGFR* (Symphogen) CFA s.c. | Day 28 25 μg rhEGFR + rhEGFRvIII** (Symphogen) IFA s.c. | Day 42 25 μg rhEGFR + rhEGFRvIII** (Symphogen) IFA s.c. | Day 56 25 μg rhEGFR + rhEGFRvIII** (Symphogen) IFA s.c. | Day 59 |
| 118 | Balb/c | Day 1 1 × 10$^7$ HN5 cells CFA i.p. | Day 29 100 μg rhGH-EGFR (Symphogen) IFA s.c. | Day 44 1 × 10$^7$ HN5 cells IFA i.p. | Day 58 25 μg rhEGFR, (Sigma E3641) IFA s.c. | Day 61 |
| 119 | C57B | Day 1 1 × 10$^7$ HN5 cells CFA i.p. | Day 29 100 μg rhGH-EGFR (Symphogen) IFA s.c. | Day 44 1 × 10$^7$ HN5 cells IFA i.p. | Day 58 25 μg rhEGFR, (Sigma E3641) IFA s.c. | Day 61 |

TABLE 5

Nested primer set

| Primer | Conc. (nM) | Sequence | Seq. no |
|---|---|---|---|
| mHCrev1- | 0.2 | GGACAGGGMTCCAKAGTTCCADKT | 18 |
| hmJK set | | | |
| hmJK1-v2 | 0.2 | GACAGATGGTGCAGCCACAGTTCGTTTGATTTCCAGCT | 19 |
| hmJK2-v2 | 0.2 | GACAGATGGTGCAGCCACAGTTCGTTTTATTTCCAGCT | 20 |
| hmJK4-v2 | 0.2 | GACAGATGGTGCAGCCACAGTTCGTTTTATTTCCAACT | 21 |
| hmJK5-v2 | 0.2 | GACAGATGGTGCAGCCACAGTTCGTTTCAGCTCCAGC | 22 |

K = G/T, M = A/C, D = AGT; Conc.-final concentration.

TABLE 6

Kappa constant splicing primer set

| Primer | Conc. | Sequence | Seq. no. |
|---|---|---|---|
| Human kappa constant amplification | | | |
| hKCforw- | 0.2 | GAACTGTGGCTGCACCATCTGTC | 23 |
| Kappa3' | 0.2 | ACCGCCTCCACCGGCGGCCGCTTATTAACACTCTCCCCTGTTG | 24 |
| Splicing by overlap extension | | | |
| mhKCrev | 0.2 | ACCGCCTCCACCGGCGGCCGCTTATTAACACTCTCCCCTGTTGAAGCT | 25 |
| mJH set | | | |
| mJH1 | 0.2 | GGAGGCGCTCGAGACGGTGACCGTGGTCCC | 12 |
| mJH2 | 0.2 | GGAGGCGCTCGAGACTGTGAGAGTGGTGCC | 13 |

TABLE 6-continued

Kappa constant splicing primer set

| Primer | Conc. | Sequence | Seq. no. |
|---|---|---|---|
| mJH3 | 0.2 | GGAGGCGCTCGAGACAGTGACCAGAGTCCC | 14 |
| mJH4 | 0.2 | GGAGGCGCTCGAGACGGTGACTGAGGTTCC | 15 |

APPENDIX 1

Antibody Constant Region Sequences

>Human IGKC region
(Seq. no. 26)
ttcatcttcccgccatctgatgagcagttgaaatctggaactgcctctgt
tgtgtgcctgctgaataacttctatcccagagaggccaaagtacagtgga
aggtggataacgccctccaatcgggtaactcccaggagagtgtcacagag
caggacagcaaggacagcacctacagcctcagcagcaccctgacgctgag
caaagcagactacgagaaacacaaagtctacgcctgcgaagtcacccatc
agggcctgagctcgcccgtcacaaagagcttcaacaggggagagtgttaa
taagcggccgccggtggaggcggt >Human IGKC region
(Seq. no. 27)
TVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKS
FNRGEC

| Exon1 | 1 ... 298 |
| Intron | 299 ... 689 |
| Exon2 | 690 ... 734 |
| Intron | 735 ... 852 |
| Exon3 | 853 ... 1182 |
| Intron | 1183 ... 1279 |
| Exon4 | 1280 ... 1602 |

>human IGHG1 constant domain genomic sequence
(Seq. no. 28)
agtgcctccaccaagggcccatcggtcttccccctggcaccctcctccaa
gagcacctctgggggcacagcggccctgggctgcctggtcaaggactact
tccccgaaccggtgacggtgtcgtggaactcaggcgccctgaccagcggc
gtgcacaccttcccggctgtcctacagtcctcaggactctactccctcag
cagcgtggtgaccgtgccctccagcagcttgggcacccagacctacatct
gcaacgtgaatcacaagcccagcaacaccaaggtggacaagagagttggt
gagaggccagcacagggagggagggtgtctgctggaagccaggctcagcg
ctcctgcctggacgcatccggctatgcagtcccagtccaggcagcaag
gcaggccccgtctgcctcttcacccggaggcctctgcccgcccactcat
gctcagggagagggtcttctggcttttccccaggctctgggcaggcaca
ggctaggtgcccctaacccaggccctgcacacaaaggggcaggtgctggg
ctcagacctgccaagagccatatccgggaggaccctgccctgacctaag
cccaccccaaaggccaaactctccactccctcagctcggacaccttctct
cctcccagattccagtaactcccaatcttctctctgcagagcccaaatct
tgtgacaaaactcacacatgcccaccgtgcccaggtaagccagcccaggc
ctcgccctccagctcaaggcgggacaggtgccctagagtagcctgcatcc
agggacaggccccagccgggtgctgacacgtccacctccatctcttcctc
agcacctgaactcctggggggaccgtcagtcttcctcttccccccaaaac
ccaaggacaccctcatgatctcccggacccctgaggtcacatgcgtggtg
gtggacgtgagccacgaagaccctgaggtcaagttcaactggtacgtgga
cggcgtggaggtgcataatgccaagacaaagccgcgggaggagcagtaca
acagcacgtaccgtgtggtcagcgtcctcaccgtcctgcaccaggactgg
ctgaatggcaaggagtacaagtgcaaggtctccaacaaagccctcccagc
ccccatcgagaaaaccatctccaaagccaaaggtgggacccgtggggtgc
gagggccacatggacagaggccggctcggcccaccctctgccctgagagt
gaccgctgtaccaacctctgtccctacagggcagccccgagaaccacagg
tgtacaccctgcccccatcccgggaggagatgaccaagaaccaggtcagc
ctgacctgcctggtcaaaggcttctatcccagcgacatcgccgtggagtg
ggagagcaatgggcagccggagaacaactacaagaccacgcctcccgtgc
tggactccgacggctccttcttcctctatagcaagctcaccgtggacaag
agcaggtggcagcaggggaacgtcttctcatgctccgtgatgcatgaggc
tctgcacaaccactacacgcagaagagcctctccctgtccccgggtaaat
ga >IGHG1
(Seq. no. 29)
SASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKRVE
PKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNG
KEYKCKVSNKALPAPIEKTISKAKGQPREPQVYTLPPSREEMTKNQVSLT
CLVKGFYPSDIAVEWESNGQPENNYKTTPPVLDSDGSFFLYSKLTVDKSR
WQQGNVFSCSVMHEALHNHYTQKSLSLSPGK

What is claimed is:

1. A method of producing a library of cognate pairs comprising linked immunoglobulin variable region encoding sequences, said method comprising:
   (a) immunizing a rodent with a target antigen and providing a lymphocyte-comprising cell fraction from said rodent;
   (b) isolating from said lymphocyte-comprising cell fraction cells expressing CD43 and CD138 antigen or MHCII and B220 antigen;
   (c) distributing the isolated cells from step b) individually into a plurality of vessels to obtain a population of isolated single cells, wherein each cell expresses CD43 and CD138 antigen or MHCII and B220 antigen; and
   (d) amplifying, in a multiplex molecular amplification procedure, nucleotide sequences of interest using templates derived from said isolated single cells; and effecting linkage of the amplified nucleotide sequences of interest to generate a library of cognate pairs of a light chain variable region encoding sequence associated with a heavy chain variable region encoding sequence.

2. The method according to claim 1, wherein the individual isolated single cells are expanded to populations of isogenic cells, prior to performing the amplification and linkage of 1(d).

3. The method according to claim 1, wherein the lymphocyte-comprising cell fraction comprises splenocytes, whole blood, bone marrow, mononuclear cells, or white blood cells.

4. The method according to claim 1, wherein the lymphocyte-comprising cell fraction is enriched for plasma cells or plasmablasts.

5. The method of claim 1, further comprising assessing prior to step (b) that the population of lymphocyte-comprising cells comprises cells expressing CD43 and CD138 antigen or MHCII and B220 antigen.

6. The method of claim 1, further comprising enriching said lymphocyte-comprising cell fraction for a lymphocyte population expressing CD43 and CD138 antigen or MHCII and B220 prior to step (b).

7. The method of claim 1, wherein the isolated cells are CD138 High/CD43 High or CD138 Intermediate/CD43 High relative to the lymphocyte-comprfsing cell fraction.

8. The method of claim 7, wherein the isolated cells are CD138 High/CD43 High relative to the lymphocyte-comprising cell fraction.

9. The method of claim 1, wherein the isolation comprises an automated sorting procedure.

10. The method of claim 6, wherein the enrichment comprises an automated sorting procedure.

11. The method of claim 9, wherein the automated sorting procedure is MACS or FACS.

12. The method of claim 10, wherein the automated sorting procedure is MACS or FACS.

13. The method of claim 1, wherein the rodent is transgenic and expresses human immunoglobulins.

14. The method of claim 1, wherein said multiplex molecular amplification procedure is a multiplex RT-PCR amplification.

15. The method according to claim 14, wherein said multiplex RT-PCR amplification is a two step process comprising a separate reverse transcription (RT) step prior to the multiplex PCR amplification.

16. The method according to claim 14, wherein said multiplex RT-PCR amplification is performed in a single step comprising initially adding all the components necessary to perform both reverse transcription (RT) and multiplex PCR amplification into a single vessel.

17. The method of claim 1, wherein said linkage of the nucleotide sequences of interest is performed in the same vessel as the multiplex molecular amplification.

18. The method according to claim 14, wherein said linkage of the nucleotide sequences of interest is effected in association with the multiplex RT-PCR amplification, utilizing a multiplex overlap-extension primer mix.

19. The method of claim 1, wherein said linkage of the nucleotide sequences of interest is effected by ligation.

20. The method of claim 1, wherein an additional molecular amplification, utilizing a primer mix adapted for amplifying the linked nucleic acid sequences of interest, is performed.

21. The method according to claim 18, wherein the multiplex overlap-extension primer mix comprises primer sets wherein at least one primer set member of each primer set comprises an overlap-extension tail capable of hybridizing to the overlap-extension tail of a primer set member of a second primer set.

22. The method according to claim 18, wherein the multiplex overlap-extension primer mix comprises:
(a) at least one mKappar 1 or hmJK primer complementary to the sense strand of an immunoglobulin light chain region encoding sequence;
(b) at least one mVK primer complementary to the antisense strand of an immunoglobulin light chain variable region encoding sequence or light chain variable region leader sequence, and capable of forming a primer set with the primer(s) in (a);
(c) at least one mCHrev1, mHCrev 1-ext, or mJH primer complementary to the sense strand of an immunoglobulin heavy chain domain encoding sequence; and
(d) at least one mVH primer complementary to the antisense strand of an immunoglobulin heavy chain variable region encoding sequence or heavy chain variable region leader sequence, and capable of forming a primer set with the primer(s) in (c).

23. The method according to claim 21, wherein the multiplex overlap-extension primer mix comprises:
(a) at least one mKapparl or hmJK primer complementary to the sense strand of an immunoglobulin light chain region encoding sequence;
(b) at least one mVK primer complementary to the antisense strand of an immunoglobulin light chain variable region encoding sequence or light chain variable region leader sequence, and capable of forming a primer set with the primer(s) in (a);
(c) at least one mCHrev 1, mHCrev 1-ext, or mJH primer complementary to the sense strand of an immunoglobulin heavy chain domain encoding sequence; and
(d) at least one mVH primer complementary to the antisense strand of an immunoglobulin heavy chain variable region encoding sequence or heavy chain variable region leader sequence, and capable of forming a primer set with the primer(s) in (c).

24. The method according to claim 1, further comprising inserting the linked nucleotide sequences or a library of cognate pairs into a vector.

25. The method according to claim 24, wherein said vector is selected among cloning vectors, shuttle vectors, display vectors or expression vectors.

26. The method according to claim 24, wherein the linked nucleotide sequences or individual members of the library of cognate pairs comprise an immunoglobulin heavy chain variable region encoding sequence associated with light chain variable region encoding sequence and said sequences are inserted in-frame into a vector already containing sequences encoding one or more immunoglobulin constant domains or fragments thereof.

27. The method according to claim 24, further comprising creating a sub-library by selecting a subset of cognate pairs of linked variable region sequences that encode binding proteins with a desired target specificity, thereby generating a library of target-specific cognate pairs of variable region encoding sequences.

28. The method according to claim 27, further comprising transferring said library of target-specific cognate pairs of variable region encoding sequences to a mammalian expression vector.

29. The method according to claim 28, wherein the mammalian expression vector encodes one or more constant region domains selected from human immunoglobulin classes IgA1, IgA2, IgD, IgE, IgG1, IgG2, IgG3, IgG4, IgM, kappa light chain or lambda light chain.

30. The method according to claim 24, farther comprising introducing a vector comprising a segment of linked nucleotide sequences into a host cell, cultivating said host cells under conditions adapted for expression, and obtaining the protein product expressed from the vector inserted into said host cell.

31. The method according to claim 30, wherein said protein product is an antibody comprising a cognate pair of a light chain variable region associated with a heavy chain variable region.

32. The method of claim 1, wherein a subset of cognate pairs of linked variable region encoding sequences encode immunoglobulins that bind the target antigen.

33. A method of producing a library of cognate pairs comprising linked immunoglobulin variable region encoding sequences, said method comprising:

(a) immunizing a rodent with a target antigen and providing a lymphocyte-comprising cell fraction from said rodent;
(b) isolating from said lymphocyte-comprising cell fraction cells that express CD43 and CD138 antigen;
(c) distributing the isolated cells from step b) individually into a plurality of vessels to obtain a population of isolated single cells, wherein each cell expresses CD43 and CD138 antigen; and
(d) amplifying, in a multiplex molecular amplification procedure, nucleotide sequences of interest using templates derived from said isolated single cells; and effecting linkage of the amplified nucleotide sequences of interest to generate a library of cognate pairs of a light chain variable region encoding sequence associated with a heavy chain variable region encoding sequence.

34. The method of claim 33, wherein a subset of cognate pairs of linked variable region encoding sequences encode immunoglobulins that bind the target antigen.

35. A method of producing a library of cognate pairs comprising linked immunoglobulin variable region encoding sequences, said method comprising:

(a) immunizing a rodent with a target antigen and providing a lymphocyte-comprising cell fraction from said rodent;
(b) enriching said lymphocyte-comprising cell fraction for a lymphocyte population expressing CD43 and CD138 antigen or MHCII and B220 antigen;
(c) distributing cells from the enriched cell fraction obtained in step b) individually into a plurality of vessels to obtain a population of isolated single cells, wherein each cell expresses CD43 and CD138 antigen or MHCII and B220 antigen; and
(d) amplifying, in a multiplex molecular amplification procedure, nucleotide sequences of interest using templates derived from said isolated single cells; and effecting linkage of the amplified nucleotide sequences of interest to generate a library of cognate pairs of a light chain variable region encoding sequence associated with a heavy chain variable region encoding sequence.

36. The method of claim 35, wherein a subset of cognate pairs of linked variable region encoding sequences encode immunoglobulins that bind the target antigen.

* * * * *

SEQUENCE LISTING

<160> NUMBER OF SEQ ID NOS: 33

<210> SEQ ID NO 1
<211> LENGTH: 20
<212> TYPE: DNA
<213> ORGANISM: artificial
<220> FEATURE:
<223> OTHER INFORMATION: PCR primer

<400> SEQUENCE: 1
gacsgatggg cccttggtgg     20

<210> SEQ ID NO 2
<211> LENGTH: 20
<212> TYPE: DNA
<213> ORGANISM: artificial
<220> FEATURE:
<223> OTHER INFORMATION: PCR primer

<400> SEQUENCE: 2
gctgtaggtg ctgtctttgc     20

<210> SEQ ID NO 3
<211> LENGTH: 39
<212> TYPE: DNA
<213> ORGANISM: artificial
<220> FEATURE:
<223> OTHER INFORMATION: PCR primer

<400> SEQUENCE: 3
tattcccatg gcgcgccsag gtccarctgc arcagyctg     39

<210> SEQ ID NO 4
<211> LENGTH: 37
<212> TYPE: DNA
<213> ORGANISM: artificial
<220> FEATURE:
<223> OTHER INFORMATION: PCR primer

<400> SEQUENCE: 4
tattcccatg gcgcgccgar gtgmagctkg tkgagtc     37

<210> SEQ ID NO 5
<211> LENGTH: 37
<212> TYPE: DNA
<213> ORGANISM: artificial
<220> FEATURE:
<223> OTHER INFORMATION: PCR primer

<400> SEQUENCE: 5
tattcccatg gcgcgccsag gtgcagctkm aggagtc     37

<210> SEQ ID NO 6
<211> LENGTH: 37
<212> TYPE: DNA
<213> ORGANISM: artificial
<220> FEATURE:
<223> OTHER INFORMATION: PCR primer

<400> SEQUENCE: 6
tattcccatg gcgcgcccag gttactctga aagagtc     37

<210> SEQ ID NO 7
<211> LENGTH: 39
<212> TYPE: DNA

<213> ORGANISM: artificial
<220> FEATURE:
<223> OTHER INFORMATION: PCR primer

<400> SEQUENCE: 7
tattcccatg gcgcgcccag atccagttgg tgcagtctg        39

<210> SEQ ID NO 8
<211> LENGTH: 45
<212> TYPE: DNA
<213> ORGANISM: artificial
<220> FEATURE:
<223> OTHER INFORMATION: PCR primer

<400> SEQUENCE: 8
ggcgcgccat gggaatagct agccgayatc cagatgachc arwct        45

<210> SEQ ID NO 9
<211> LENGTH: 44
<212> TYPE: DNA
<213> ORGANISM: artificial
<220> FEATURE:
<223> OTHER INFORMATION: PCR primer

<400> SEQUENCE: 9
ggcgcgccat gggaatagct agccracatt gtgmtgachc agtc        44

<210> SEQ ID NO 10
<211> LENGTH: 46
<212> TYPE: DNA
<213> ORGANISM: artificial
<220> FEATURE:
<223> OTHER INFORMATION: PCR primer

<400> SEQUENCE: 10
ggcgcgccat gggaatagct agccsamatt gtkctsaccc artctc        46

<210> SEQ ID NO 11
<211> LENGTH: 45
<212> TYPE: DNA
<213> ORGANISM: artificial
<220> FEATURE:
<223> OTHER INFORMATION: PCR primer

<400> SEQUENCE: 11
ggcgcgccat gggaatagct agccgatrtt gtgatgacbc arrct        45

<210> SEQ ID NO 12
<211> LENGTH: 30
<212> TYPE: DNA
<213> ORGANISM: artificial
<220> FEATURE:
<223> OTHER INFORMATION: PCT primer

<400> SEQUENCE: 12
ggaggcgctc gagacggtga ccgtggtccc        30

<210> SEQ ID NO 13
<211> LENGTH: 30
<212> TYPE: DNA
<213> ORGANISM: artificial
<220> FEATURE:
<223> OTHER INFORMATION: PCR primer

<400> SEQUENCE: 13
ggaggcgctc gagactgtga gagtggtgcc        30

```
<210> SEQ ID NO 14
<211> LENGTH: 30
<212> TYPE: DNA
<213> ORGANISM: artificial
<220> FEATURE:
<223> OTHER INFORMATION: PCR primer

<400> SEQUENCE: 14
ggaggcgctc gagacagtga ccagagtccc                                30

<210> SEQ ID NO 15
<211> LENGTH: 30
<212> TYPE: DNA
<213> ORGANISM: artificial
<220> FEATURE:
<223> OTHER INFORMATION: PCT primer

<400> SEQUENCE: 15
ggaggcgctc gagacggtga ctgaggttcc                                30

<210> SEQ ID NO 16
<211> LENGTH: 39
<212> TYPE: DNA
<213> ORGANISM: artificial
<220> FEATURE:
<223> OTHER INFORMATION: PCR primer

<400> SEQUENCE: 16
gatggtgcag ccacagttcg tttgatttcc agcttggtg                      39

<210> SEQ ID NO 17
<211> LENGTH: 39
<212> TYPE: DNA
<213> ORGANISM: artificial
<220> FEATURE:
<223> OTHER INFORMATION: PCT primer

<400> SEQUENCE: 17
gatggtgcag ccacagttcg tttcagctcc agcttggtc                      39

<210> SEQ ID NO 18
<211> LENGTH: 24
<212> TYPE: DNA
<213> ORGANISM: artificial
<220> FEATURE:
<223> OTHER INFORMATION: PCT primer

<400> SEQUENCE: 18
ggacagggmt ccakagttcc adkt                                      24

<210> SEQ ID NO 19
<211> LENGTH: 43
<212> TYPE: DNA
<213> ORGANISM: artificial
<220> FEATURE:
<223> OTHER INFORMATION: PCR primer

<400> SEQUENCE: 19
gacagatggt gcagccacag ttcgtttgat ttccagcttg gtg                 43

<210> SEQ ID NO 20
<211> LENGTH: 43
<212> TYPE: DNA
<213> ORGANISM: artificial
<220> FEATURE:
<223> OTHER INFORMATION: PCR primer
```

```
<400> SEQUENCE: 20
gacagatggt gcagccacag ttcgttttat ttccagcttg gtc        43

<210> SEQ ID NO 21
<211> LENGTH: 43
<212> TYPE: DNA
<213> ORGANISM: artificial
<220> FEATURE:
<223> OTHER INFORMATION: PCR primer

<400> SEQUENCE: 21
gacagatggt gcagccacag ttcgttttat ttccaacttt gtc        43

<210> SEQ ID NO 22
<211> LENGTH: 43
<212> TYPE: DNA
<213> ORGANISM: artificial
<220> FEATURE:
<223> OTHER INFORMATION: PCR primer

<400> SEQUENCE: 22
gacagatggt gcagccacag ttcgtttcag ctccagcttg gtc        43

<210> SEQ ID NO 23
<211> LENGTH: 23
<212> TYPE: DNA
<213> ORGANISM: artificial
<220> FEATURE:
<223> OTHER INFORMATION: PCR primer

<400> SEQUENCE: 23
gaactgtggc tgcaccatct gtc        23

<210> SEQ ID NO 24
<211> LENGTH: 43
<212> TYPE: DNA
<213> ORGANISM: artificial
<220> FEATURE:
<223> OTHER INFORMATION: PCR primer

<400> SEQUENCE: 24
accgcctcca ccggcggccg cttattaaca ctctcccctg ttg        43

<210> SEQ ID NO 25
<211> LENGTH: 51
<212> TYPE: DNA
<213> ORGANISM: artificial
<220> FEATURE:
<223> OTHER INFORMATION: PCR primer

<400> SEQUENCE: 25
accgcctcca ccggcggccg cttattaaca ctctcccctg ttgaagctct t        51

<210> SEQ ID NO 26
<211> LENGTH: 324
<212> TYPE: DNA
<213> ORGANISM: artificial
<220> FEATURE:
<223> OTHER INFORMATION: PCR primer

<400> SEQUENCE: 26
ttcatcttcc cgccatctga tgagcagttg aaatctggaa ctgcctctgt tgtgtgcctg        60
ctgaataact tctatcccag agaggccaaa gtacagtgga aggtggataa cgccctccaa       120
tcgggtaact cccaggagag tgtcacagag caggacagca aggacagcac ctacagcctc       180
```

| | |
|---|---:|
| agcagcaccc tgacgctgag caaagcagac tacgagaaac acaaagtcta cgcctgcgaa | 240 |
| gtcacccatc agggcctgag ctcgcccgtc acaaagagct tcaacagggg agagtgttaa | 300 |
| taagcggccg ccggtggagg cggt | 324 |

<210> SEQ ID NO 27
<211> LENGTH: 106
<212> TYPE: PRT
<213> ORGANISM: Homo sapiens

<400> SEQUENCE: 27

```
Thr Val Ala Ala Pro Ser Val Phe Ile Phe Pro Pro Ser Asp Glu Gln
1               5                   10                  15
Leu Lys Ser Gly Thr Ala Ser Val Val Cys Leu Leu Asn Asn Phe Tyr
            20                  25                  30
Pro Arg Glu Ala Lys Val Gln Trp Lys Val Asp Asn Ala Leu Gln Ser
        35                  40                  45
Gly Asn Ser Gln Glu Ser Val Thr Glu Gln Asp Ser Lys Asp Ser Thr
    50                  55                  60
Tyr Ser Leu Ser Ser Thr Leu Thr Leu Ser Lys Ala Asp Tyr Glu Lys
65                  70                  75                  80
His Lys Val Tyr Ala Cys Glu Val Thr His Gln Gly Leu Ser Ser Pro
                85                  90                  95
Val Thr Lys Ser Phe Asn Arg Gly Glu Cys
            100                 105
```

<210> SEQ ID NO 28
<211> LENGTH: 1602
<212> TYPE: DNA
<213> ORGANISM: artificial
<220> FEATURE:
<223> OTHER INFORMATION: PCR primer

<400> SEQUENCE: 28

| | |
|---|---:|
| agtgcctcca ccaagggccc atcggtcttc cccctggcac cctcctccaa gagcacctct | 60 |
| gggggcacag cggccctggg ctgcctggtc aaggactact tccccgaacc ggtgacggtg | 120 |
| tcgtggaact caggcgccct gaccagcggc gtgcacacct tcccggctgt cctacagtcc | 180 |
| tcaggactct actccctcag cagcgtggtg accgtgccct ccagcagctt gggcacccag | 240 |
| acctacatct gcaacgtgaa tcacaagccc agcaacacca aggtggacaa gagagttggt | 300 |
| gagaggccag cacagggagg gagggtgtct gctggaagcc aggctcagcg ctcctgcctg | 360 |
| gacgcatccc ggctatgcag tcccagtcca gggcagcaag caggccccg tctgcctctt | 420 |
| cacccggagg cctctgcccg ccccactcat gctcagggag agggtcttct ggcttttcc | 480 |
| ccaggctctg gcaggcaca ggctaggtgc ccctaaccca ggccctgcac acaaaggggc | 540 |
| aggtgctggg ctcagacctg ccaagagcca tatccgggag gaccctgccc ctgacctaag | 600 |
| cccacccaa aggccaaact ctccactccc tcagctcgga caccttctct cctcccagat | 660 |
| tccagtaact cccaatcttc tctctgcaga gcccaaatct tgtgacaaaa ctcacacatg | 720 |
| cccaccgtgc ccaggtaagc cagcccaggc ctcgccctcc agctcaaggc gggacaggtg | 780 |
| ccctagagta gcctgcatcc agggacaggc cccagccggg tgctgacacg tccacctcca | 840 |
| tctcttcctc agcacctgaa ctcctggggg gaccgtcagt cttcctcttc cccccaaaac | 900 |
| ccaaggacac cctcatgatc tcccggaccc ctgaggtcac atgcgtggtg gtggacgtga | 960 |
| gccacgaaga ccctgaggtc aagttcaact ggtacgtgga cggcgtggag gtgcataatg | 1020 |
| ccaagacaaa gccgcgggag gagcagtaca acagcacgta ccgtgtggtc agcgtcctca | 1080 |

```
ccgtcctgca ccaggactgg ctgaatggca aggagtacaa gtgcaaggtc tccaacaaag    1140
ccctcccagc ccccatcgag aaaaccatct ccaaagccaa aggtgggacc cgtggggtgc    1200
gagggccaca tggacagagg ccggctcggc ccaccctctg ccctgagagt gaccgctgta    1260
ccaacctctg tccctacagg gcagccccga gaaccacagg tgtacaccct gcccccatcc    1320
cgggaggaga tgaccaagaa ccaggtcagc ctgacctgcc tggtcaaagg cttctatccc    1380
agcgacatcg ccgtggagtg ggagagcaat gggcagccgg agaacaacta caagaccacg    1440
cctcccgtgc tggactccga cggctccttc ttcctctata gcaagctcac cgtggacaag    1500
agcaggtggc agcaggggaa cgtcttctca tgctccgtga tgcatgaggc tctgcacaac    1560
cactacacgc agaagagcct ctccctgtcc ccgggtaaat ga                       1602
```

<210> SEQ ID NO 29
<211> LENGTH: 331
<212> TYPE: PRT
<213> ORGANISM: Homo sapiens

<400> SEQUENCE: 29

```
Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Arg Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285
```

```
Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 30
<211> LENGTH: 39
<212> TYPE: DNA
<213> ORGANISM: artificial
<220> FEATURE:
<223> OTHER INFORMATION: PCR primer

<400> SEQUENCE: 30
gatggtgcag ccacagttcg ttttatttcc agcttggtc                              39

<210> SEQ ID NO 31
<211> LENGTH: 39
<212> TYPE: DNA
<213> ORGANISM: artificial
<220> FEATURE:
<223> OTHER INFORMATION: PCR primer

<400> SEQUENCE: 31
gatggtgcag ccacagttcg ttttatttcc aactttgtc                              39

<210> SEQ ID NO 32
<211> LENGTH: 8
<212> TYPE: DNA
<213> ORGANISM: artificial
<220> FEATURE:
<223> OTHER INFORMATION: References seq

<400> SEQUENCE: 32 agtcagtc                                                                 8

<210> SEQ ID NO 33
<211> LENGTH: 11
<212> TYPE: DNA
<213> ORGANISM: artificial
<220> FEATURE:
<223> OTHER INFORMATION: Reference Seq

<400> SEQUENCE: 33
taatcaatcg g                                                            11
```